United States Patent
Pryor et al.

(10) Patent No.: US 8,111,239 B2
(45) Date of Patent: Feb. 7, 2012

(54) MAN MACHINE INTERFACES AND APPLICATIONS

(75) Inventors: Timothy R. Pryor, Tecumseh (CA); Peter Smith, Ann Arbor, MI (US)

(73) Assignee: Motion Games, LLC, Austin, TX (US)

(*) Notice: Subject to any disclaimer, the term of this patent is extended or adjusted under 35 U.S.C. 154(b) by 803 days.

(21) Appl. No.: 11/429,305

(22) Filed: May 8, 2006

(65) Prior Publication Data
US 2006/0202953 A1 Sep. 14, 2006

Related U.S. Application Data

(62) Division of application No. 10/622,812, filed on Jul. 21, 2003, now Pat. No. 7,042,440, which is a division of application No. 09/138,285, filed on Aug. 21, 1998, now Pat. No. 6,720,949.

(60) Provisional application No. 60/056,639, filed on Aug. 22, 1997, provisional application No. 60/059,561, filed on Sep. 19, 1997.

(51) Int. Cl.
*G09G 5/00* (2006.01)
(52) U.S. Cl. ............... 345/156; 345/158; 348/77
(58) Field of Classification Search .......... 345/156–158, 345/168; 348/77
See application file for complete search history.

(56) References Cited

U.S. PATENT DOCUMENTS

| | | | |
|---|---|---|---|
| 3,846,826 A | 11/1974 | Mueller | |
| 4,014,000 A | 3/1977 | Uno et al. | |
| 4,146,924 A | 3/1979 | Birk et al. | |
| 4,199,137 A | 4/1980 | Giguere | |
| 4,219,847 A | 8/1980 | Pinkney et al. | |
| 4,305,131 A | 12/1981 | Best | |
| 4,375,674 A | 3/1983 | Thornton | |
| 4,396,945 A | 8/1983 | DiMatteo et al. | |
| 4,416,924 A | 11/1983 | Peterson et al. | |
| 4,435,835 A | 3/1984 | Sakow et al. | |
| 4,475,122 A | 10/1984 | Green | |
| 4,484,179 A | 11/1984 | Kasday | |

(Continued)

FOREIGN PATENT DOCUMENTS
JP 63167923 7/1988

OTHER PUBLICATIONS

Bales et al, "Marking Parts to Aid Robot Vision", NASA Technical Paper 1819, Apr. 1981.

*Primary Examiner* — Kevin M Nguyen
*Assistant Examiner* — Kenneth B Lee, Jr.
(74) *Attorney, Agent, or Firm* — Warner Norcross & Judd LLP

(57) ABSTRACT

Affordable methods and apparatus are disclosed for inputting position, attitude (orientation) or other object characteristic data to computers for the purpose of Computer Aided Design, Painting, Medicine, Teaching, Gaming, Toys, Simulations, Aids to the disabled, and internet or other experiences. Preferred embodiments of the invention utilize electro-optical sensors, and particularly TV Cameras, providing optically inputted data from specialized datum's on objects and/or natural features of objects. Objects can be both static and in motion, from which individual datum positions and movements can be derived, also with respect to other objects both fixed and moving. Real-time photogrammetry is preferably used to determine relationships of portions of one or more datums with respect to a plurality of cameras or a single camera processed by a conventional PC.

22 Claims, 33 Drawing Sheets

U.S. PATENT DOCUMENTS

| | | | |
|---|---|---|---|
| 4,542,375 | A | 9/1985 | Alles et al. |
| 4,602,280 | A | 7/1986 | Maloomian |
| 4,613,942 | A | 9/1986 | Chen |
| 4,629,319 | A | 12/1986 | Clarke et al. |
| 4,631,676 | A | 12/1986 | Pugh |
| 4,631,847 | A | 12/1986 | Colin |
| 4,654,872 | A | 3/1987 | Hisano et al. |
| 4,654,949 | A | 4/1987 | Pryor |
| 4,672,564 | A | 6/1987 | Egli et al. |
| 4,686,374 | A | 8/1987 | Liptay-Wagner et al. |
| 4,687,200 | A | 8/1987 | Shirai |
| 4,843,568 | A | 6/1989 | Krueger et al. |
| 4,988,981 | A * | 1/1991 | Zimmerman et al. ........ 345/158 |
| 5,072,294 | A | 12/1991 | Engle |
| 5,148,591 | A | 9/1992 | Pryor |
| 5,168,531 | A | 12/1992 | Sigel |
| 5,297,061 | A | 3/1994 | Dementhon et al. |
| 5,325,472 | A | 6/1994 | Horiuchi et al. |
| 5,388,059 | A | 2/1995 | DeMenthon |
| 5,454,043 | A | 9/1995 | Freeman |
| 5,459,793 | A | 10/1995 | Naoi et al. |
| 5,506,682 | A | 4/1996 | Pryor |
| 5,521,616 | A | 5/1996 | Capper et al. |
| 5,566,283 | A | 10/1996 | Modegi et al. |
| 5,581,276 | A | 12/1996 | Cipolla et al. |
| 5,594,469 | A * | 1/1997 | Freeman et al. ............... 345/158 |
| 5,616,078 | A * | 4/1997 | Oh ..................................... 463/8 |
| 5,617,312 | A | 4/1997 | Iura et al. |
| 5,624,117 | A * | 4/1997 | Ohkubo et al. ........... 273/148 B |
| 5,772,522 | A | 6/1998 | Nesbit et al. |
| 5,870,771 | A | 2/1999 | Oberg |
| 5,878,174 | A | 3/1999 | Stewart et al. |
| 5,889,505 | A | 3/1999 | Toyama et al. |
| 5,913,727 | A | 6/1999 | Ahdoot |
| 5,926,168 | A * | 7/1999 | Fan ............................... 345/158 |
| 5,966,310 | A | 10/1999 | Maeda et al. |
| 5,982,352 | A | 11/1999 | Pryor |
| 6,005,548 | A | 12/1999 | Latypov et al. |
| 6,030,290 | A | 2/2000 | Powell |
| 6,043,805 | A | 3/2000 | Hsieh |
| 6,049,327 | A | 4/2000 | Walker et al. |
| 6,057,856 | A | 5/2000 | Miyashita et al. |
| 6,084,979 | A | 7/2000 | Kanade et al. |
| 6,097,369 | A | 8/2000 | Wambach |
| 6,147,678 | A | 11/2000 | Kumar et al. |
| 6,198,485 | B1 | 3/2001 | Mack et al. |
| 6,198,487 | B1 | 3/2001 | Fortenbery et al. |
| 6,342,917 | B1 | 1/2002 | Amenta |
| 6,430,997 | B1 | 8/2002 | French et al. |
| 6,453,180 | B1 | 9/2002 | Endoh et al. |
| 6,597,817 | B1 | 7/2003 | Silverbrook |
| 6,727,887 | B1 | 4/2004 | Levine et al. |
| 6,954,906 | B1 | 10/2005 | Kamachi et al. |

* cited by examiner

MAPPING ONE RGB COMPONENT OF A COLOR
HERE, THE RED COMPONENT IS USED. THE SAME
PROCESS CAN BE USED FOR THE GREEN AND BLUE
COMPONENTS AS WELL.

Ar - IS THE RED COMPONENT OF THE AQUA COLOR

Or - IS THE RED COMPONENT OF THE ORANGE COLOR

Pr - IS THE RED COMPONENT OF THE PIXEL COLOR

Cr - IS THE RED COMPONENT OF THE COLOR ADJUSTED
     TO BE BETWEEN A AND O

MAN MACHINE INTERFACES AND APPLICATIONS

CROSS REFERENCE TO RELATED APPLICATIONS

This application is a divisional application of Ser. No. 10/622,812 filed Jul. 21, 2003 and now U.S. Pat. No. 7,042,440; which is a divisional application of Ser. No. 09/138,285, filed Aug. 21, 1998 and now U.S. Pat. No. 6,720,949; which application claims benefit of provisional application Ser. No. 60/056,639, filed Aug. 22, 1997, and provisional application Ser. No. 60/059,561, filed Sep. 19, 1997—(all of which are hereby incorporated by reference).

BACKGROUND OF THE INVENTION

1. Field of the Invention

The invention relates to simple input devices for computers, well suited for use with 3-D graphically intensive activities, and operating by optically sensing object or human positions and /or orientations. The invention in many preferred embodiments, uses real time stereo photogrammetry using single or multiple TV cameras whose output is analyzed and used as input to a personal computer.

2. Description of Related Art

The closest known references to the stereo photogrammetric imaging of datum's employed by several preferred embodiments of the invention are thought to exist in the fields of flight simulation, robotics, animation and biomechanical studies. Some early prior art references in these fields are Pugh U.S. Pat. No. 4,631,676;
Birk U.S. Pat. No. 4,416,924;
Pinckney U.S. Pat. No. 4,219,847;
U.S. Pat. No. 4,672,564 by Egli et al, filed Nov. 15, 1984;
Pryor U.S. Pat. No. 5,506,682 Robot Vision Using Targets;
Pryor, Method for Automatically Handling, Assembling & Working on Objects, U.S. Pat. No. 4,654,949; and
Pryor, U.S. Pat. No. 5,148,591, Vision Target Based Assembly.

In what is called "virtual reality", a number of other devices have appeared for human instruction to a computer. Examples are head trackers, magnetic pickups on the human and the like, which have their counterpart in the invention herein.

References from this field having similar goals to some aspects of the invention herein are:

U.S. Pat. No. 5,297,061 by Dementhon et al
U.S. Pat. No. 5,388,059 also by Dementhon, et al
U.S. Pat. No. 5,168,531 Real-time recognition of pointing information from video, by Sigel
U.S. Pat. No. 5,617,312 Computer system that enters control information by means of video camera by Iura et al, filed Nov. 18, 1994
U.S. Pat. No. 5,616,078: Motion-controlled video entertainment system, by Oh; Ketsu,
U.S. Pat. No. 5,594,469: Hand gesture machine control system, by Feeman, et al.
U.S. Pat. No. 5,454,043: Dynamic and static hand gesture recognition through low-level image analysis by Freeman;
U.S. Pat. No. 5,581,276: 3D human interface apparatus using motion recognition based on dynamic image processing, by Cipolla et al.
U.S. Pat. No. 4,843,568: Real time perception of and response to the actions of an unencumbered participant/user by Krueger, et al Iura and Sigel disclose means for using a video camera to look at a operators body or finger and input control information to a computer. Their disclosure is generally limited to two dimensional inputs in an x-y plane, such as would be traveled by a mouse used conventionally.

Dementhon discloses the use objects equipped with 4 LEDs detected with a single video camera to provide a 6 degree of freedom solution of object position and orientation. He downplays the use of retroreflector targets for this task.

Cipolla et al discusses processing and recognition of movement sequence gesture inputs detected with a single video camera whereby objects or parts of humans equipped with four reflective targets or leds are moved thru space, and a sequence of images of the objects taken and processed. The targets can be colored to aid discrimination.

Pryor, one of the inventors, in several previous applications has described single and dual (stereo) camera systems utilizing natural features of objects or special targets including retroreflectors for determination of position and orientation of objects in real time suitable for computer input, in up to 6 degrees of freedom.

Pinckney has described a single camera method for using and detecting 4 reflective targets to determine position and orientation of an object in 6 degrees of freedom. A paper by Dr. H. F. L. Pinckney entitled Theory and Development of an on line 30 Hz video photogrammetry system for real-time 3 dimensional control presented at the Symposium of Commission V Photogrammetry for Industry, Stockholm, August 1978, together with many of the references referred to therein gives many of the underlying equations of solution of photogrammetry particularly with a single camera. Another reference relating to use of two or more cameras, is Development of Stereo Vision for Industrial Inspection, Dr. S. F. El-Hakim, Proceedings of the Instrument Society of America (ISA) Symposium, Calgary Alta, Apr. 3-5 1989. This paper too has several useful references to the photogrammetry art.

Generally speaking, while several prior art references have provided pieces of the puzzle, none has disclosed a workable system capable of widespread use, the variety and scope of embodiments herein, nor the breath and novelty of applications made possible with electro-optical determination of object position and/or orientation.

In this invention, many embodiments may operate with natural features, colored targets, self-illuminated targets such as LEDS, or with retroreflective targets. Generally the latter two give the best results from the point of view of speed and reliability of detection—of major importance to widespread dissemination of the technology.

However, of these two, only the retroreflector is both low cost, and totally unobtrusive to the user. Despite certain problems using same, it is the preferred type of target for general use, at least for detection in more than 3 degrees of freedom. Even in only two degrees, where standard "blob" type image processing might reasonably be used to find ones finger for example, (e.g., U.S. Pat. No. 5,168,531 by Sigel ), use of simple glass bead based, or molded plastic corner cube based retroreflectors allows much higher frequency response (e.g. 30 Hz, 60 Hz, or even higher detection rates) from the multiple incidence angles needed in normal environments, also with lower cost computers under a wider variety of conditions—and is more reliable as well.(at least with today's PC processing power).

SUMMARY OF THE INVENTION

Numerous 3D input apparatus exist today. As direct computer input for screen manipulation, the most common is the "Mouse" that is manipulated in x and y, and through various artifices in the computer program driving the display, provides some control in z-axis. In 3 dimensions (3-D) however, this is indirect, time consuming, artificial, and requires considerable training to do well. Similar comments relate to joysticks, which in their original function were designed for input of two angles.

In the computer game world as well; the mouse, joy stick and other 2D devices prevail today.

The disclosed invention is optically based, and generally uses unobtrusive specialized datum's on, or incorporated within, an object whose 3D position and/or orientation is desired to be inputted to a computer. Typically such datums are viewed with a single TV camera, or two TV cameras forming a stereo pair. A preferred location for the camera(s) is proximate the computer display, looking outward therefrom, or to the top or side of the human work or play space.

While many aspects of the invention can be used without specialized datum's (e.g. a retro-reflective tape on ones finger, versus use of the natural finger image itself), these specialized datum's have been found to work more reliably, and at lowest cost using technology which can be capable of wide dissemination in the next few years. This is very important commercially. Even where only two-dimensional position is desired, such as x, y location of a finger tip, this is still the case.

For degrees of freedom beyond 3, we feel such specialized datum based technology is the only practical method today. Retroreflective glass bead tape, or beading, such as composed of Scotchlite 7615 by 3M co., provides a point, line, or other desirably shaped datum which can be easily attached to any object desired, and which has high brightness and contrast to surroundings such as parts of a human, clothes, a room etc, when illuminated with incident light along the optical axis of the viewing optics such as that of a TV camera. This in turn allows cameras to be used in normal environments, and having fast integration times capable of capturing common motions desired, and allows datums to be distinguished easily which greatly reduces computer processing time and cost.

Retroreflective or other datums are often distinguished by color or shape as well as brightness. Other target datums suitable can be distinguished just on color or shape or pattern, but do not have the brightness advantage offered by the retro. Suitable Retroreflectors can alternatively be glass, plastic or retroreflective glass bead paints, and can be other forms of retroreflectors than beads, such as corner cubes. But the beaded type is most useful. Shapes of datums found to be useful have been for example dots, rings, lines, edge outlines, triangles, and combinations of the foregoing.

It is a goal of this invention to provide a means for data entry that has the following key attributes among others:

Full 3D (up to 6 degrees of freedom, e.g. x, y, z, roll, pitch, yaw) real time dynamic input using artifacts, aliases, portions of the human body, or combinations thereof;

Very low cost, due also to ability to share cost with other computer input functions such as document reading, picture telephony, etc.;

Generic versatility—can be used for many purposes, and saves as well on learning new and different systems for those purposes;

Unobtrusive to the user;

Fast response, suitable for high speed gaming as well as desk use;

Compatible as input to large screen displays—including wall projections;

Unique ability to create physically real "Alias" or "surrogate" objects;

Unique ability to provide realistic tactile feel of objects in hand or against other objects, without adding cost;

A unique ability to enable "Physical" and "Natural" experience. It makes using computers fun, and allows the very young to participate. And it radically improves the ability to use 3D graphics and CAD systems with little or no training;

An ability to aid the old and handicapped in new and useful ways;

An ability to provide meaningful teaching and other experiences capable of reaching wide audiences at low cost; and An ability to give life to a child's imagination thru the medium of known objects and software, with out requiring high cost toys, and providing unique learning experiences.

What is also unique about the invention here disclosed is that it unites all of the worlds above, and more besides, providing the ability to have a common system that serves all purposes well-at lowest possible cost and complexity.

The invention has a unique ability to combine what amounts to 3D icons (physical artifacts) with static or dynamic gestures or movement sequences. This opens up, among other things, a whole new way for people, particularly children, beginners and those with poor motor or other skills to interact with the computer. By manipulating a set of simple tools and objects that have targets appropriately attached, a novice computer user can control complex 2D and 3D computer programs with the expertise of a child playing with toys!

The invention also acts as an important teaching aide, especially for small children and the disabled, who have undeveloped motor skills. Such persons can, with the invention, become computer literate far faster than those using conventional input devices such as a mouse. The ability of the invention to use any desired portion of a human body, or an object in his command provides a massive capability for control, which can be changed at will. In addition, the invention allows one to avoid carpal tunnel syndrome and other effects of using keyboards and mice. One only needs move through the air so to speak, or with ergonomically advantageous artifacts.

The system can be calibrated for each individual to magnify even the smallest motion to compensate for handicaps or enhance user comfort or other benefits.(e.g trying to work in a cramped space on an airplane). If desired, unwanted motions can be filtered or removed using the invention. (in this case a higher number of camera images than would normally be necessary is typically taken, and effects in some frames averaged, filtered or removed altogether).

The invention also provides for high resolution of object position and orientation at high speed and at very low or nearly insignificant cost. And it provides for smooth input functions without the jerkiness of mechanical devices such as a sticking mouse of the conventional variety.

In addition, the invention can be used to aid learning in very young children and infants by relating gestures of hands and other bodily portions or objects (such as rattles or toys held by the child), to music and/or visual experiences via computer generated graphics or real imagery called from a memory such as DVD disks or the like.

The invention is particularly valuable for expanding the value of life-size, near life size, or at least large screen (e.g. greater than 42 inches diagonal) TV displays. Since the projection can now be of this size at affordable cost, the invention allows an also affordable means of relating in a lifelike way to the objects on the screen—to play with them, to modify them, and other wise interrelate using ones natural actions and the naturally appearing screen size—which can also be in 3D using stereo display techniques of whatever desired type.

DESCRIPTION OF FIGURES

FIG. 1 illustrates basic sensing useful in practicing the invention.

FIG. 2 illustrates Computer aided design system (CAD) related embodiments.

FIG. 8 illustrates embodiments, some of which are a simulation analog of the design embodiments above, used for Medical or dental teaching and other applications.

FIG. 10 illustrates a natural manner of computer interaction for aiding the movement of persons hands while using the invention in multiple degree of freedom movement with ones arms resting on a armrest of a chair, car, or the like.

DETAILED DESCRIPTION OF THE INVENTION

FIG. 1a

Figure 1A:
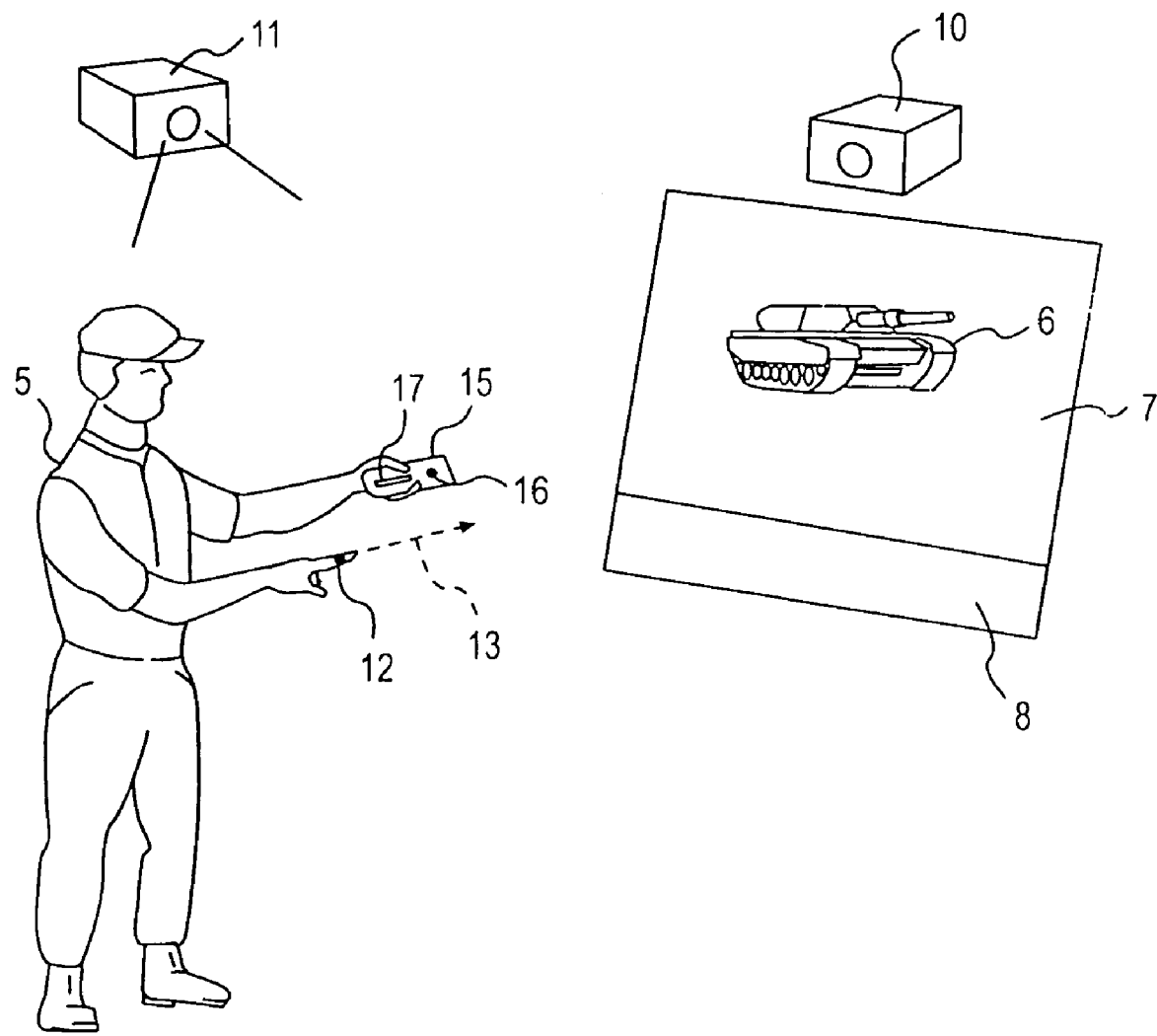
FIG. 1a illustrates a basic two dimensional embodiment of the invention utilizing one or more retroreflective datums on an object, further including means to share function with normal imaging for internet teleconferencing or other activities.

FIG. 1a illustrates a simple single camera based embodiment of the invention. In this case, a user 5, desires to point at an object 6 represented electronically on the screen 7 and cause the pointing action to register in the software contained in computer 8 with respect to that object (a virtual object), in order to cause a signal to be generated to the display 7 to cause the object to activate or allow it to be moved, (e.g. with a subsequent finger motion or otherwise). He accomplishes this using a single TV camera 10 located typically on top of the screen as shown or alternatively to the side (such as 11) to determine the position of his fingertip 12 in space, and/or the pointing direction of his finger 13.

It has been proposed by Sigel and others to utilize the natural image of the finger for this purpose and certain US patents address this in the group referenced above. Copending applications by one of the inventors (Tim Pryor) also describe finger related activity.

As disclosed in said co-pending application, it is however, often desirable to use retro-reflective material on the finger, disclosed herein as either temporarily attached to the finger as in jewelry or painted on the finger using retro-reflective coating "nail polish" or adhered to the finger such as with adhesive tape having a retro-reflective coating. Such coatings are typically those of Scotch-lite 7615 and its equivalent that have high specific reflectivity, contrasting well to their surroundings to allow easy identification. The brightness of the reflection allows dynamic target acquisition and tracking at lowest cost.

The camera system employed for the purposes of low cost desirable for home use is typically that used for Internet video conferencing and the like today. These cameras are CCD's and more recently CMOS, cameras having low cost (25-100 dollars) yet relatively high pixel counts and densities. It is considered that within a few years these will be standard on all computers, for all-intents and purposes, "free" to the applications here proposed, and interfaced via "fire wire" (IEEE 1394) or USB (universal serial bus).

The use of retroreflective and/or highly distinctive targets (e.g. bright orange triangles) allows reliable acquisition of the target in a general scene, and does not restrict the device to pointing on a desktop application under controlled lighting as shown in Sigel or others. Active (self luminous) targets such as LEDS also allow such acquisition, but are more costly, cumbersome and obtrusive and generally less preferable.

If we consider camera system 10 sitting on top of the screen 7 and looking at the user or more particularly, the user's hand, in a normal case of Internet telephony there is a relatively large field of view so that the user's face can also be seen. This same field of view can be used for this invention but it describes a relatively large volume. For higher precision, add-on lenses or zoom lenses on the camera may be used to increase the resolution.

Or it is possible according to the invention to have a plurality of cameras, one used for the Internet and the other used for the input application here described. Indeed with the ever dropping prices, the price of the actual camera including the plastic lens on the CMOS chip is so low, it is possible perhaps even to have multiple cameras with fixed magnifications, each having a separate chip!

These can easily be daisy chained with either fire wire or USB such that they can either be selected at will electronically in fact by the different magnifications or pointing directions desired.

Let us now return now to the question of determining location or orientation of a human portion such as typically a hand, or finger—in this case, a finger. In order to make this invention operate in the lowest possible cost it is desirable that the lighting available be low cost as well. Indeed if the camera units are shared with telephony using the natural lighting of the object, then the cost of specialized lighting required for the retro-reflectors adds cost to the system. The power for the lighting, such as LEDs can generally be conveyed over the USB or 1394 bus however.

The user can also point or signal with an object such as 15 having datum 16 on it, such as a retroreflective dot 16 or line target 17.

It is possible to expand the sensing of 2D positions described above into 3, 4, 5 and 6 dimensions.(x, y plus z, pitch, yaw, roll). Two sensing possibilities of the many possible, are described in various embodiments herein.

1. The first, illustrated in FIG. 1a and b is to utilize a single camera, but multiple discrete features or other targets on the object which can provide a multidegree of freedom solution. In one example, the target spacing on the object is known a priori and entered into the computer manually or automatically from software containing data about the object, or can be determined through a taught determining step.
2. The second is a dual camera solution shown in FIG. 1c and d that does not require a priori knowledge of targets and in fact can find the 3D location of one target by itself, useful for determining finger positions for example. For 6-degree freedom of information, at least three point, targets are required, although line targets, and combinations of lines and points can also be used.

Figure 1B:
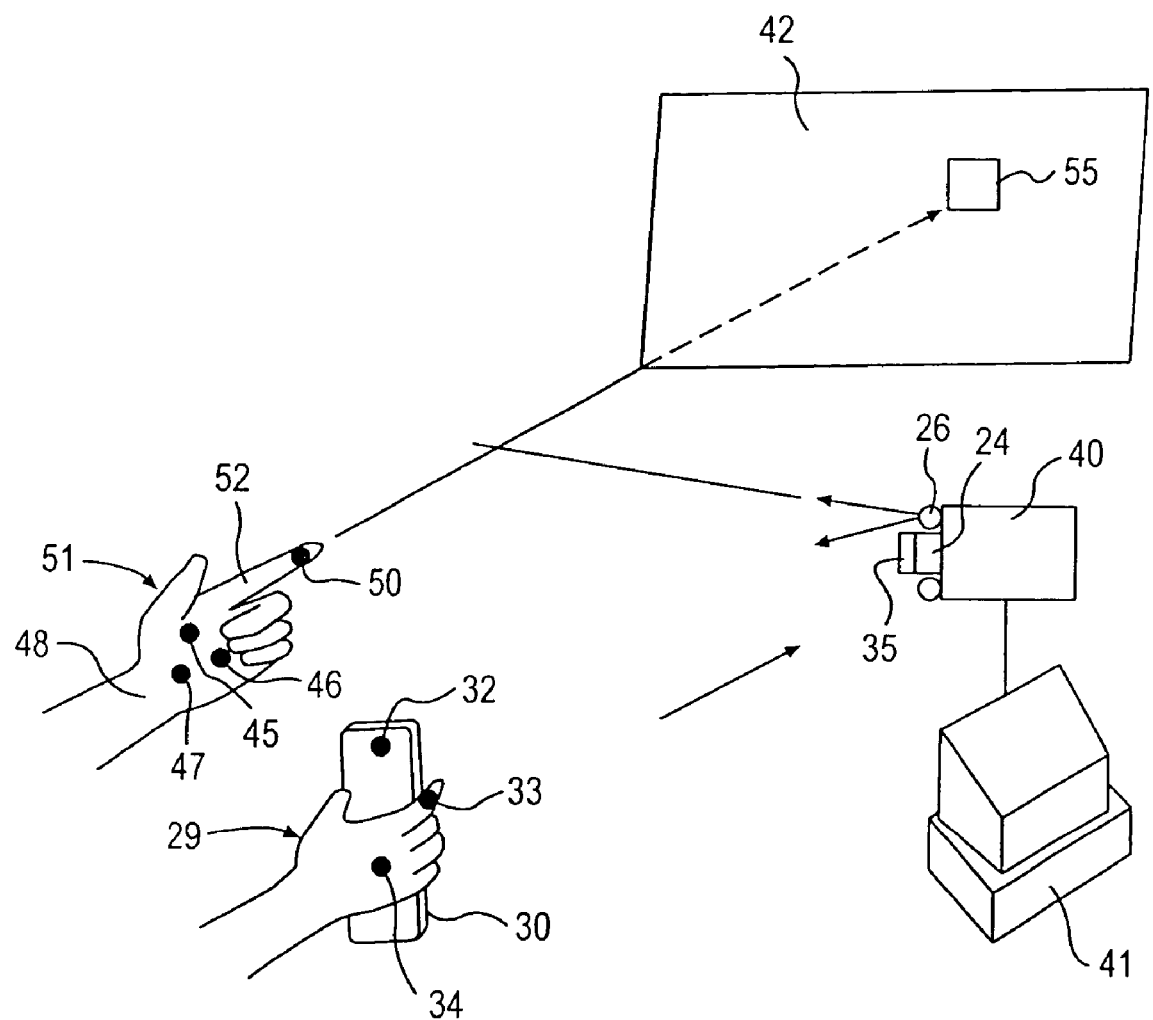
FIG. 1b illustrates a 3 Dimensional embodiment using single camera stereo with 3 or more datums on an object or wrist of the user.

FIG. 1b illustrates a 3-D (3 Dimensional) sensing embodiment using single camera stereo with 3 or more datums on a sensed object, or in another example, the wrist of the user.

As shown the user holds in his right hand 29, object 30 which has at least 3 visible datums 32, 33, and 34 which are viewed by TV camera 40 whose signal is processed by computer 41 which also controls projection display 42. TV camera 40 also views 3 other datums 45, 46 and 47, on the wrist 48 of the users left hand, in order to determine its orientation or rough direction of pointing of the left hand 51, or its position relative to object 30, or any other data (e.g. relation to the screen position or other location related to the mounting position of the TV camera, or to the users head if viewed, or what ever. The position and orientation of the object and hand can be determined from the 3 point positions in the camera image using known photogrammetric equations (see Pinckney, reference U.S. Pat. No. 4,219,847 and other references in papers referenced).

Alternatively to the 3 discrete point target, a colored triangular target for example can be used in which the intersections of lines fitted to its sides define the target datums, as discussed below.

It is also possible to use the camera 40 to see other things of interest as well. For the direction of pointing of the user at an object 55 represented on display 42 is determine for example datum 50 on finger 52 of users left hand 51 (whose wrist position and attitude can be also determined).

Alternatively, the finger can be detected just from its general gray level image, and can be easily identified in relation to the targeted wrist location (especially if the user, as shown, has clenched his other fingers such that the finger 52 is the only one extended on that hand).

The computer can process the gray level image using known techniques, for example blob and other algorithms packaged with the MATROX brand GENESIS image processing board for the PC, and determine the pointing direction of the finger using the knowledge of the wrist gained from the datums. This allows the left hand finger 50 to alternatively point at a point (or touch a point) to be determined on the object 30 held in the right hand as well.

FIG. 1c

Figure 1C:
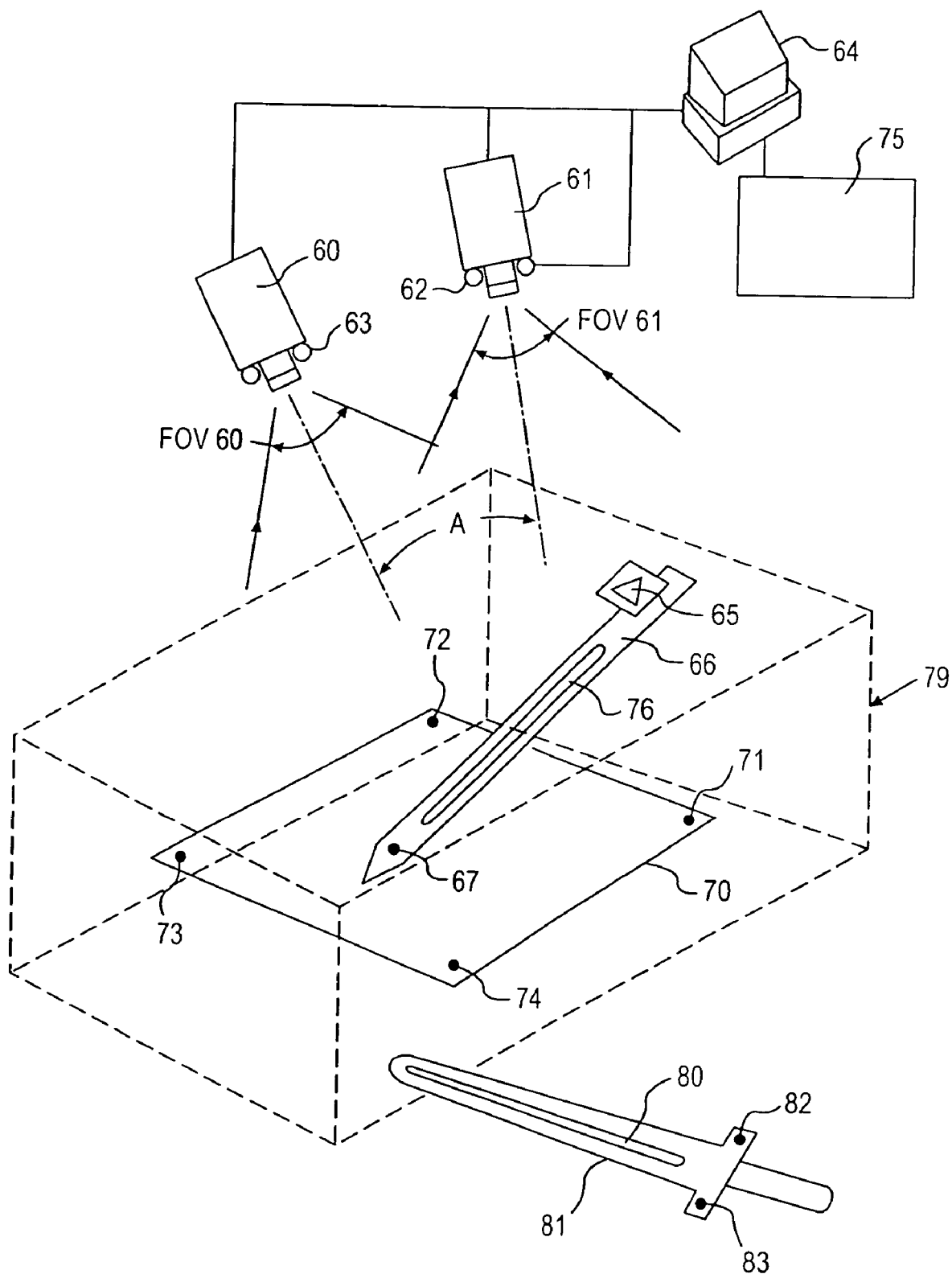
FIG. 1c illustrates another version of the embodiment of FIG. 1a, in which two camera "binocular" stereo cameras are used to image an artificial target on the end of a pencil. Additionally illustrated is a 2 camera stereo and a line target plus natural hole feature on an object.

FIG. 1c illustrates another version of the embodiments of FIG. 1a and b, in which two camera "binocular" stereo cameras 60 and 61 processed by computer 64 are used to image artificial target (in this case a triangle, see also FIG. 2), 65, on the end of pencil 66, and optionally to improve pointing resolution, target 67 on the tip end of the pencil, typically a known small distance from the tip. (the user and his hand holding the pencil is not shown for clarity. This imaging allows one to track the pencil tip position in order to determine where on the paper (or TV screen, in the case of a touch screen ) the pencil is contacting. (see also FIG. 2, and FIG. 12).

For best results it is often desirable to have independently controllable near coaxial light sources 62 and 63 are shown controlled by computer 64 to provide illumination of retroreflective targets for each camera independently. This is because at different approach angles the retroreflector reflects differently, and since the cameras are often angularly spaced (e.g. by non-zero angle A), they do not see a target the same.

Numerous other camera arrangements, processing, computation, and other issues are discussed in general relative to accurate determination of object positions using two or more camera stereo vision systems in the S. F. El Hakim paper referenced above and the additional references referred to therein.

The computer can also acquire the stereo image of the paper and the targets in its four corners, 71-74. Solution of the photogrammetric equation allows the position of the paper in space relative to the cameras to be determined, and thence the position of the pencil, and particularly its tip, to the paper, which is passed to display means 75 or another computer program. Even with out the target on the end, the pointing direction can be determined from target 65 and knowing the length of the pencil the tip position calculated.

A line target 76 can also be useful on the pencil, or a plurality of line targets spaced circumferentially, can also be of use in defining the pencil pointing direction from the stereo image pair.

A working volume of the measurement system is shown, in dotted lines 79—that is the region on and above the desk top in this case where the sensor system can operate effectively. Typically this is more than satisfactory for the work at hand. It is noted that due to possible compound inclination of the cameras, and other geometric considerations, the effective working volume for any given accuracy or resolution criteria, does not necessarily have parallel sides.

It is noted that the dual ( Stereo pair )camera system of FIG. 1 has been extensively tested and can provide highly accurate position and orientation information in up to 6 degrees of freedom. One particular version using commercial CCD Black and white cameras and a MATROX "GENESIS" framegrabber and image processing board, and suitable stereo photogrammetry software running in an Intel Pentium 300 MHZ based computer, has characteristics well suited to input from a large desktop CAD station for example. This provides 30 Hz updates of all 6 axes (x y z roll pitch and yaw )data over a working volume of 0.5 meter×0.5 meter in x and y (the desktop, where cameras are directly overhead pointing down at the desk) and 0.35 meters in z above the desk, all to an accuracy of 0.1 mm or better, when used with clearly visible round retroreflective (scotchlite 7615 based) datums approx. 5-15 mm in diameter on an object for example. This is accurate enough for precision tasks such as designing objects in 3D cad systems, a major goal of the invention.

The cameras in this example are mounted overhead. If mounted to the side or front, or at an angle such as 45 degrees to the desktop, the z axis becomes the direction outward from the cameras.

FIG. 1c additionally illustrates 2 camera stereo arrangement, used in this case to determine the position and orientation of an object having a line target, and a datum on a portion of the user. Here, camera s 60 and 61 are positioned to view a retro-reflective line target 80 in this case running part of the length of a toy sword blade 81. The line target in this case is made as part of the plastic sword, and is formed of molded in corner cube reflectors similar to those in a tail light reflector on a car. It may also made to be one unique color relative to the rest of the sword, and the combination of the two gives an unmistakable indication.

There are typically no other bright lines in any typical image when viewed retroreflectively. This also illustrates how target shape (i.e. a line) can be used to discriminate against unwanted other glints and reflections which might comprise a few bright pixels worth in the image. It is noted that a line type of target can be cylindrical in shape if wrapped around a cylindrical object, which can be viewed then from multiple angles.

Matching of the two camera images and solution of the photogrammetric equations gives the line target pointing direction. If an additional point is used, such as 82 the full 6 degree of freedom solution of the sword is available. Also shown here is yet another point, 83, which serves two purposes, in that it allows an improved photogrammetric solution, and it serves as a redundant target in case 82 cant be seen, due to obscuration, obliteration, or what have you.

Figure 15A:
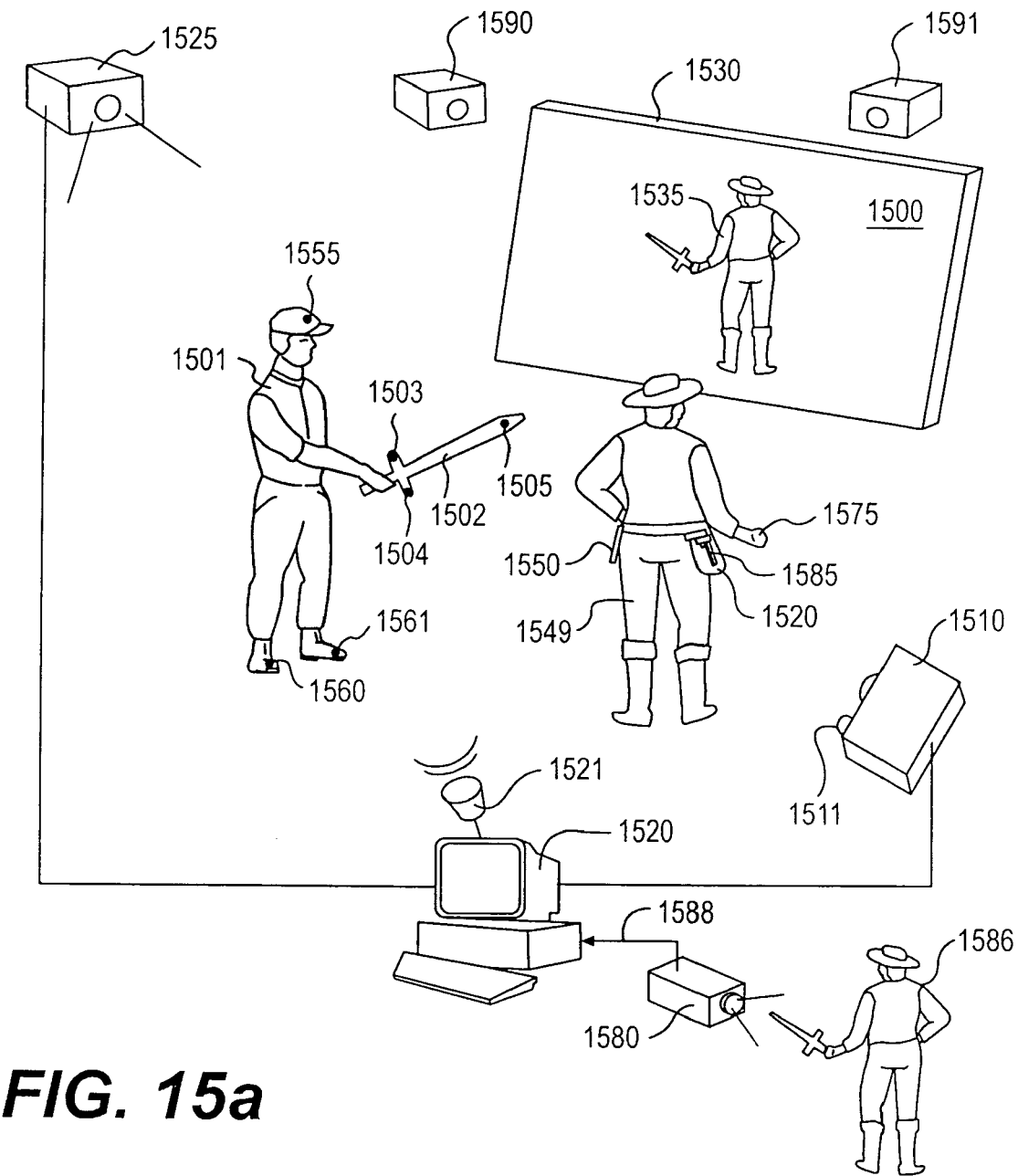
FIG. 15 illustrates a sword play and pistol video game play of the invention using life size projection screens, with side mounted stereo camera and head tracking audio system (and/or TV camera/light source tracker).

This data is calculated in computer 64, and used to modify a display on screen 75 as desired, and further described in FIG. 15.

In one embodiment a MATROX GENESIS frame processor card on an IBM 300 mhz PC was used to read both cameras, and process the information at the camera frame rate of 30 HZ. Such line targets are very useful on sleeves of clothing, seams of gloves for pointing, rims of hats, and other decorative and practical purposes for example for example outlining the edges of objects or portions thereof, such as holes and openings.

Typically the cameras 60 and 61 have magnifications and fields of view which are equal, and overlap in the volume of measurement desired. The axes of the cameras can be parallel, but for operation at ranges of a few meters or less, are often inclined at an acute angle A with respect to each other, so as to increase the overlap of their field of view—particularly if larger baseline distances d are used for increased accuracy (albeit with less z range capability.). For example for a cad drawing application, A can be 30-45 degrees, with a base line of 0.5 to 1 meter. Where as for a video game such as FIG. 5, where z range could be 5 meters or more, the angle A and the base line would be less, to allow a larger range of action.

Data Base

The datums on an object can be known a priori relative to other points on the object, and to other datums, by selling or other wise providing the object designed with such knowledge to a user and including with it a CD ROM disc or other computer interfacable storage medium having this data. Alternatively, the user or someone, can teach the computer system this information. This is particularly useful when the datums are applied by the user on arbitrary objects.

FIG. 1d

Figure 12:
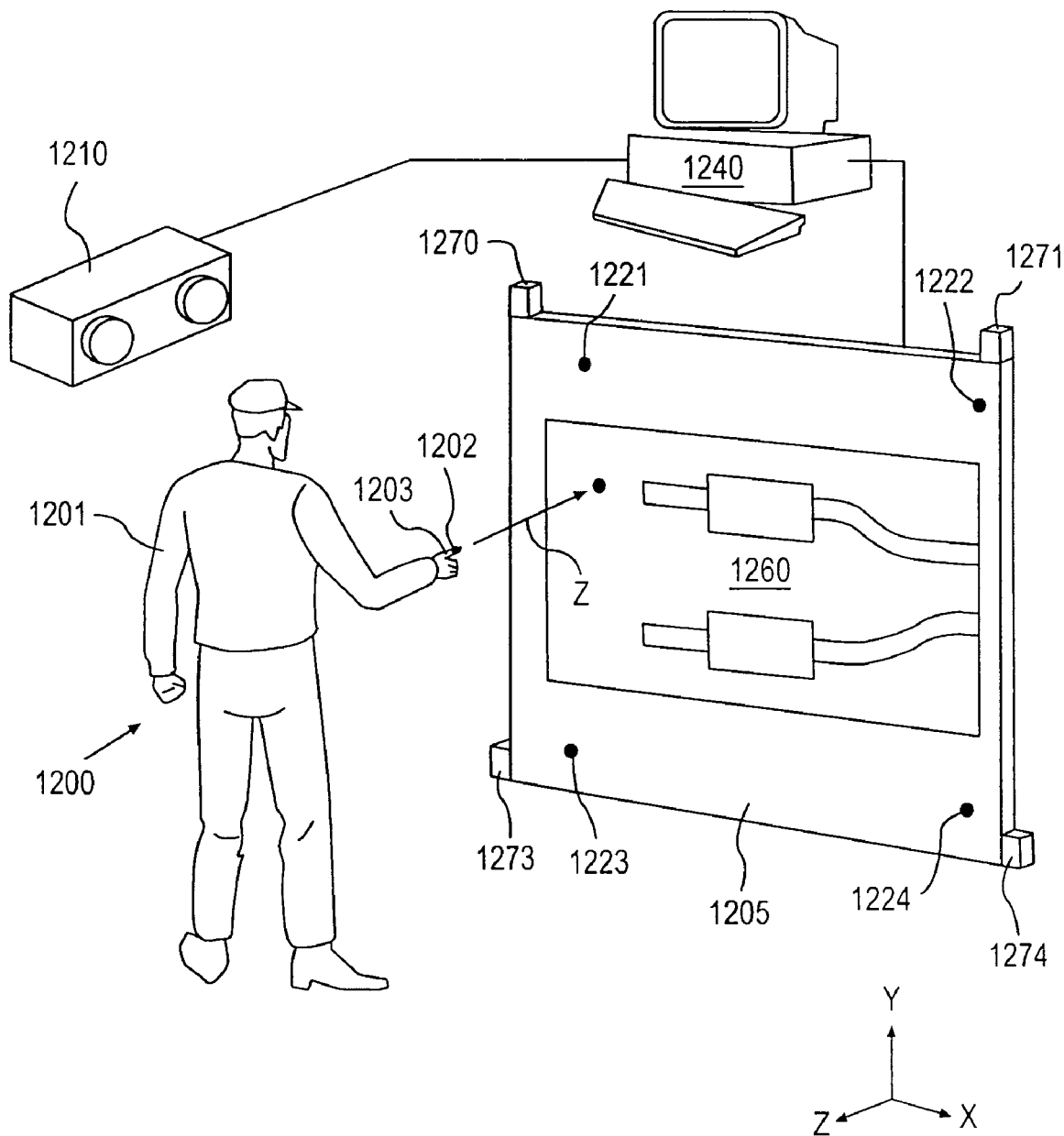
FIG. 12 illustrates a touch screen employing target inputs from fingers or other objects in contact or virtual contact with the screen, either of the conventional CRT variety, an LCD screen, or a projection screen-including aerial projection in space. Calibration or other functions via targets projected on the screen is also disclosed.

Illustrated here are steps used in the invention relating to detection of a single point to make a command, in this case, the position (or change of position, i.e. movement) of a finger tip in FIG. 12 having retroreflective target attached 1202 detected by stereo pair of TV cameras 1210, using detection algorithm which in its simplest case is based on thresholding the image to see only the bright target indication from the finger (and optionally, any object associated therewith such as a screen to be touched for example).

If this is insufficient to unambiguously defined the datum on the finger, added algorithms may be employed which are themselves known in the art (many of which are commonly packaged with image analysis frame grabber boards such as the MATROX GENESIS. The processes can include, for example:
- a brightness detection step relative to surroundings, or to immediate surroundings (contrast);
- a shape detection step, in which a search for a shape is made, such as a circle, ring, triangle, etc.;
- a color detection step, where a search for a specific color is made;
- a movement step, wherein only target candidates which have moved from a location in a previous TV image are viewed.

Each step, may process only those passing the previous step, or each may be performed independently, and the results compared later. The orders of these steps can be changed but each adds to further identify the valid indication of the finger target.

Next the position of the targeted finger is determined by comparing the difference in location of the finger target in the two camera images of the stereo pair. There is no matching problem in this case, as a single target is used, which appears as only one found point in each image.

After the Image of finger (or other tool) tip is found, its location is computed relative to the screen or paper, and this data is inputted to the computer controlling the display to modify same, for example the position of a drawing line, an icon, or to determine a vector of movement on the screen.

Motion Detection.

The computer 8 can be used to analyze incoming TV image based signals and determine which points are moving in the image This is helpful to eliminate background data which is stationary, since often times only moving items such as a hand or object are of interest. In addition, the direction of movement is in many cases the answer desired or even the fact that a movement occurred at all.

A simple way to determine this is to subtract an image of retroreflective targets of high contrast from a first image—and just determine which parts are different—essentially representing movement of the points. Small changes in lighting or other effects are not registered. There are clearly more sophisticated algorithms as well.

Motion pre processing is useful when target contrast is not very high, as it allows one to get rid of extraneous regions and concentrate all target identification and measurement processing on the real target items.

Such processing is also useful when two camera stereo is used, as only moving points are considered in image matching—a problem when there are lots of points in the field.

Can it be assumed that the object is moving? The answer is yes if it's a game or many other activities. However there may be a speed of movement of issue. Probably frame to frame is the criteria, in a game, namely 30 Hz for a typical camera. However, in some cases movement might be defined as something much slower—e.g. 3 Hz. for a CAD system input using deliberate motion of a designer.

Once the moving datum is identified, then the range can be determined and if the object is then tracked even if not moving from that point onward, the range measurement gives a good way to lock onto the object using more than just 2 dimensions.

One might actually use an artificial movement of the target if one doesn't naturally exist. This could be done by causing it to vibrate If a one or more LEDs is used as a target, they can be made to blink, which also shows up in an image subtraction (image with led on, vs. image with led off). The same is true of a target which changed color, showing up in subtraction of color images.

Image subtraction or other computer processing operations can also be useful in another sense. One can also subtract background, energizing the retroreflective illumination light with no retroreflective targets present, and then with them. One idea is simply to take a picture of a room or other work space, and then bring in the targeted object. That would seem pretty simple to subtract or whatever. And the net result is that any bright features in the space which are not of concern, such as bright door knobs, glasses, etc are eliminated from consideration.

This can also be done with colored targets, doing a color based image subtract-especially useful when one knows the desired colors a prori (as one would, or could, via a teach mode).

Figure 1D:
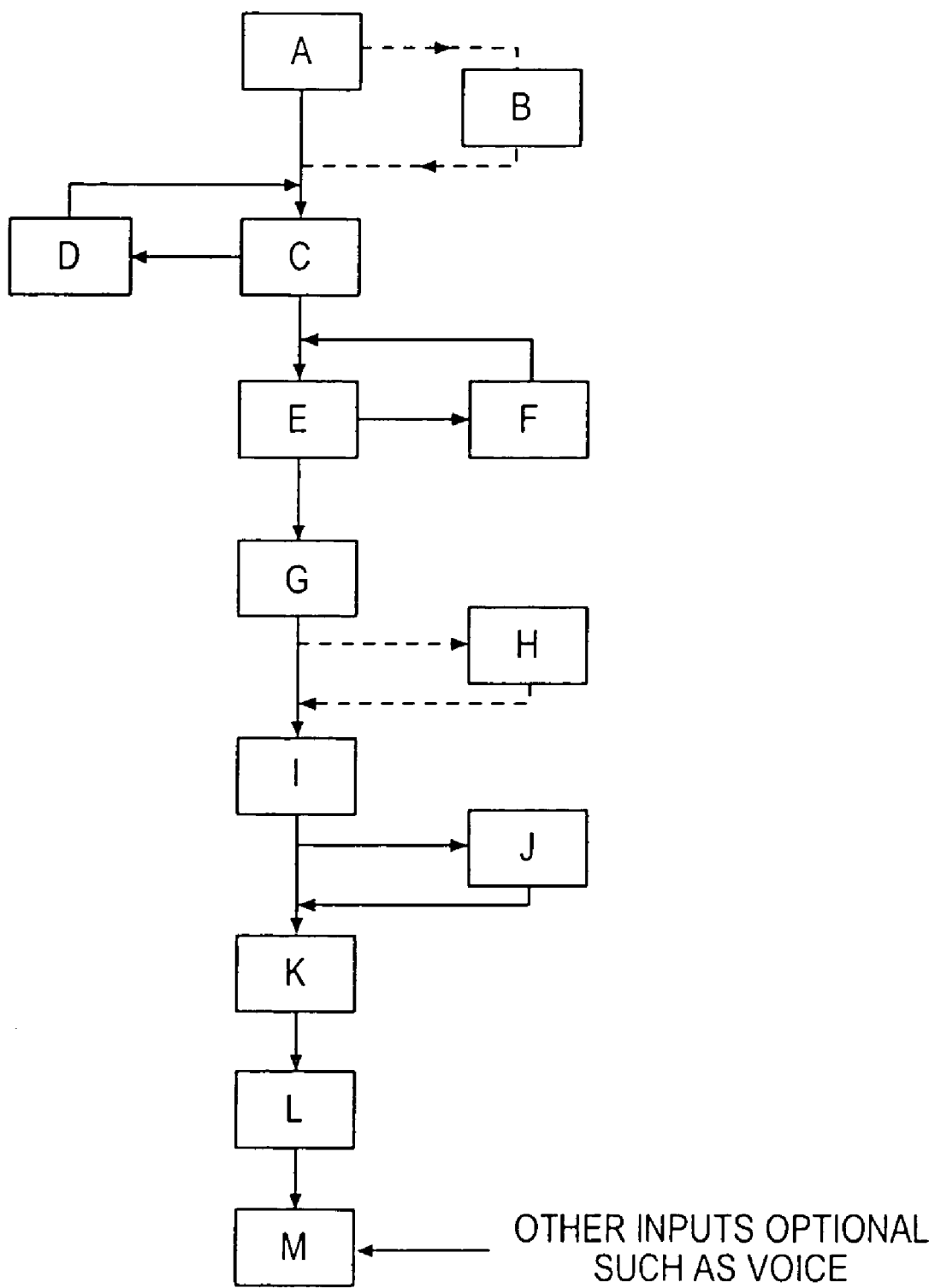
FIG. 1d illustrates a control flow chart of the invention.
Figure 1E:
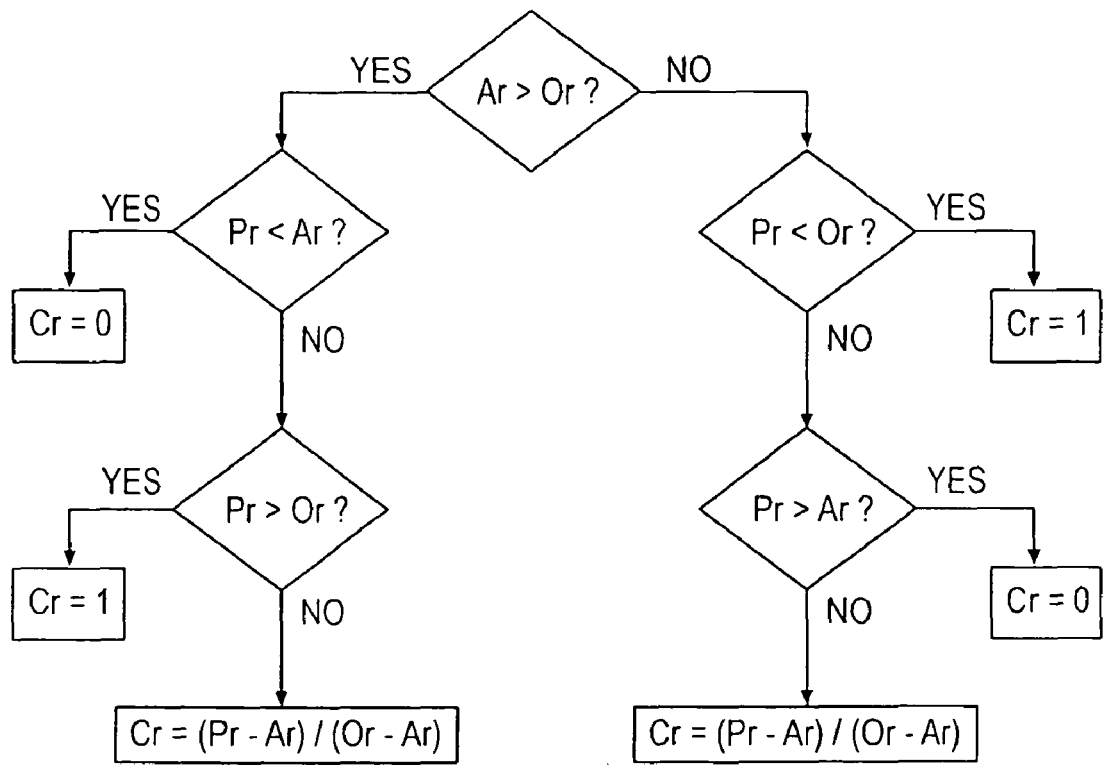
FIG. 1e is a flow chart of a color target processing embodiment.

A flow chart is shown in FIG. 1d illustrating the steps as follows:
A. Acquire images of stereo pair;
B. Optionally preprocess images to determine if motion is present. If so, pass to next step otherwise do not or do anyway (as desired);
C. Threshold images;
D. If light insufficient, change light or other light gathering parameter such as integration time;
E. Identify target(S);
F. If not identifiable, add other processing steps such as a screen for target color, shape, or size;
G. Determine centroid or other characteristic of target point (in this case a retro dot on finger);
H. Perform auxiliary matching step if required;
I. Compare location in stereo pair to determine range z and x y location of target(s);
J. Auxiliary step of determining location of targets on screen if screen position not known to computer program. Determine via targets on screen housing or projected on to screen for example;
K. Determine location of target relative to screen;
L. Determine point in display program indicated;
M. Modify display and program as desired.

The simple version of the invention here disclosed answers several problems experienced in previous attempts to implement such inputs to computers.
1. Computationally intensive;
2. Latency (frequency response, time to get position or orientation answer);
3. Noise (unreliability caused by ambient electronic, processing, or other conditions);
4. Lighting (unreliability caused by ambient illumination, processing, or other conditions);
5. Initialization;
6. Background problems, where the situation background cannot be staged, as in a cad system input on a desk.

It particularly achieves this simply and at low cost because of the function of the retroreflector targets used, which help answer all 6 needs above. When combined with color and/or shape detection, the system can be highly reliable fast and low cost. In some more controlled cases, having slower movements and more uniform backgrounds for example, retro material is not needed.

FIG. 1e

The following is a multi-degree of freedom image processing description of a triangular shaped color target (disclosed itself in several embodiments of the invention herein) which can be found optically using one or more cameras to obtain the 3 dimensional location and orientation of the target using a computer based method described below. It uses color processing to advantage, as well as a large number of pixels for highest resolution, and is best for targets that are defined by a large number of pixels in the image plane, typically because the target is large, or the cameras are close to the target, or the camera field is composed of a very large number of pixels.

The method is simple but unique in that it can be applied 1) in a variety of degrees to increase the accuracy (albeit at the expense of speed), 2) with 1 or more cameras (more cameras increase accuracy), 3) it can utilize the combination of the targets colors and triangles, (1 or more) to identify the tool or object. It utilizes the edges of the triangles to obtain accurate subpixel accuracy. A triangle edge can even have a gentle curve and the method will still function well. Other geometric shapes can also be processed similarly in some cases.

The method is based on accurately finding the 3 vertices (F0,G0,F1,G1,F2,G2) of each triangle in the camera field by accurately defining the edges and then computing the intersection of these edge curves. This is generally more accurate, than finding 3 or 4 points from spot centroids. However, the choice of which to use, often comes down to which is more pleasing to the consumer, or more rugged and reliable in use.

The preferred implementation uses 1 or more color cameras to capture a target composed of a brightly colored right triangle on a rectangle of different brightly colored background material. The background color and the triangle color must be two colors that are easily distinguished from the rest of the image. For purposes of exposition we will describe the background color as a bright orange and the triangle as aqua.

By using the differences between the background color and the triangle color, the vertices of the triangle can be found very accurately. If there are more than one triangle on a target, a weighted average of location and orientation information can be used to increase accuracy.

The method starts searching for a pixel with the color of the background or of the triangle beginning with the pixel location of the center of the triangle from the last frame. Once a pixel with the triangle "aqua" color is found, the program marches in four opposite directions until each march detects a color change indicative of an edge dividing the triangle and the "orange" background. Next, the method extends the edges to define three edge lines of the triangle with a least squares method. The intersection points of the resulting three lines are found, and serve as rough estimates of the triangle vertices. These can serve as input for applications that don't require high accuracy.

If better accuracy is desired, these provisional lines are then used as a starting point for the subpixel refinement process. Each of these 3 lines is checked to see if it is mainly horizontal. If a line is mainly horizontal, then a new line will be determined by fitting a best fit of a curve through the pixel in each column that straddles the provisional line. If a line is mainly vertical, then the same process proceeds on rows of pixels.

The color of each pixel crossed by a line is translated into a corresponding numeric value. A completely aqua pixel is would receive the value 0, while a completely orange pixel would receive the value 1. All other colors produce a number between 0 and 1, based on their relative amounts of aqua and orange. This numeric value, V, assigned to a pixel is a weighted average of the color components (such as the R, G, B values) of the pixel. If the components of the calibrated aqua are AR, AG, AB and those of orange are OR, OG, OB, and the pixel components are PR, PG, PB, then the numeric value V is:

$$V=WR*CR+WG*CG+WB*CB$$

Figure 2A:
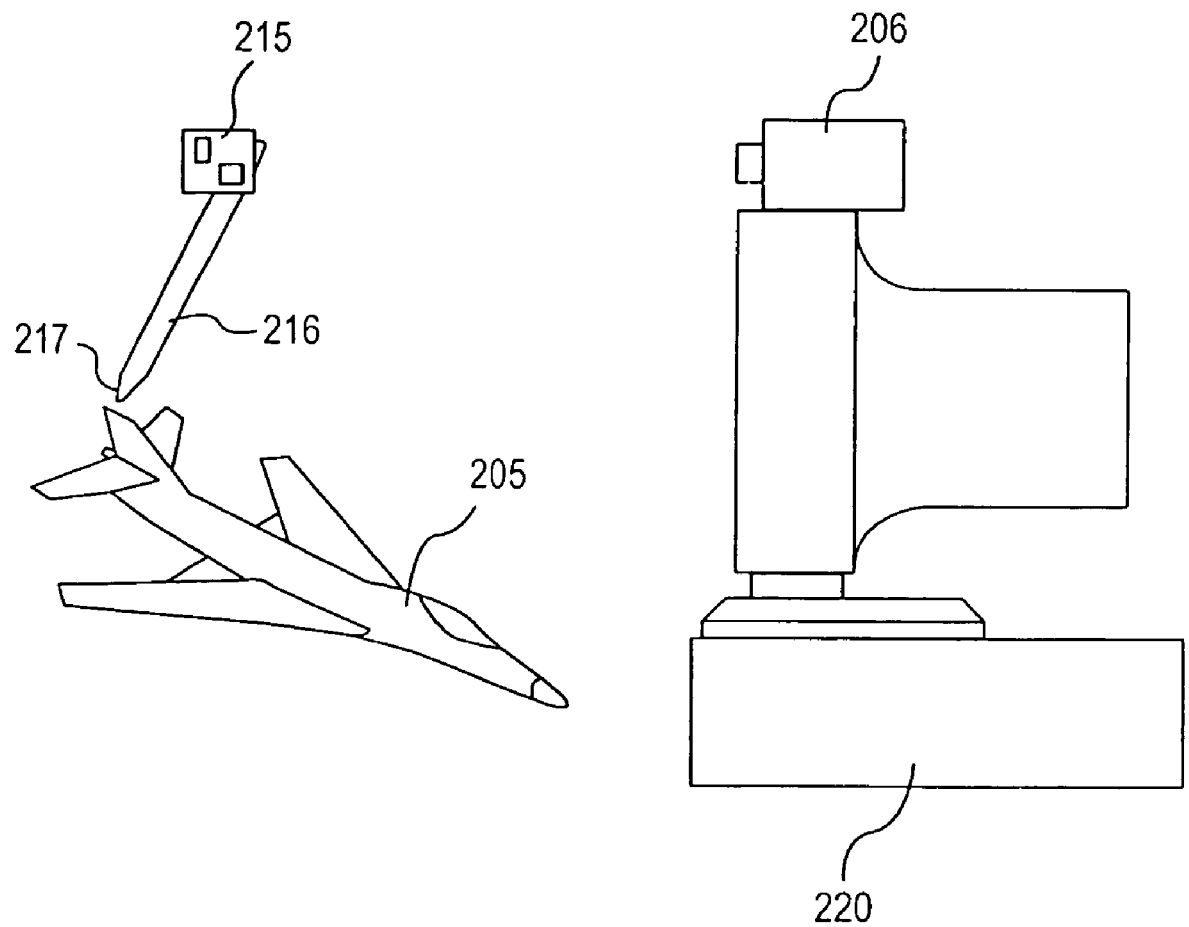
FIG. 2a Describes a illustrates a first CAD embodiment according to the invention, and a version for 3-D digitizing and other purposes.

With WR, WG, WB being weighting constants between 0 and 1 and CR is defined as:

A flow chart is shown in FIG. 2a.

The same process can be used to define CG and CB.

This value V is compared with the ideal value U which is equal to the percentage of orangeness calculated assuming the angle of the provisional line is the same as that of the ideal line. For example, a pixel which is crossed by the line in the exact middle would have a U of 0.5, since it is 50% aqua and 50% orange. A fit of U-V in the column (or row) in the vicinity of the crossing of the provisional line gives a new estimate of the location of the true edge crossing. Finally, the set of these crossing points can be fit with a line or gentle curve for each of the three edges and the 3 vertices can be computed from the intersections of these lines or curves.

We can now use these three accurate vertices in the camera plane (F0,G0,F1,G1,F2,G2) together with lens formula (here we will use the simple lens formula for brevity) to relate the x and y of the target to F and G $$F=\lambda X/Z;\ G=\lambda Y/Z$$

$\lambda$ is the focal length and z is the perpendicular distance from the lens to a location on the target. A triangle on the target is initially defined as lying in a plane parallel to the lens plane. The preferred configuration has one right triangle whose right angle is defined at x0, y0, z0 with one edge (of length A) extending along the direction of the F axis of the camera and with the other edge (of length B) extending along the direction of the G axis of the camera. The actual target orientation is related to this orientation with the use of Euler Angles $\phi$, $\theta$, $\psi$. Together with the lens equations and the Euler equations, the 6 derived data values of the 3 vertices (F0, G0, F1, G1, F2, G2) can be used to define 6 values of location and orientation of the target. The location and orientation of a point of interest on any tool or object rigidly attached to this target can be easily computed from calibration data and ordinary translation and rotation transformations. Refinements to handle lens distortions can be handled by forming a correction function with calibration data that modifies the locations of the F and G data.

The Euler formulation is nonlinear. We linearize the equations by assuming initially that the angles have not changed much since the last video frame. Thus we replace $\phi$ with $\phi(old)+U1$., $\theta$ with $\theta(old)+U2$, $\psi$ with $\psi(old)+U3$, and z0 with z0(old)+U4 or:

$$\phi=\phi+U1$$

$$\theta=\theta+U2$$

$$\psi=\psi+U3$$

$$z0=z0+U4$$

Substituting these into the Euler equations and applying the lens formulas leads to a matrix equation $$S\ U=R$$

that can be solved for the U values with a standard methods such as Gauss Jordan routine. The angles and z0 can be updated iteratively until convergence is achieved. The coefficients of the matrix are defined as:

$$s11 = -A\ (\cos((\psi)(F1/\lambda\ \cos(\psi)+\sin(\psi))-\sin(\phi)\ \cos(\theta)\\(F1/\lambda\ \sin(\psi)-\cos(\psi)))$$

$$s12 = A\ \sin(\theta)\ \cos((\phi)(F1/\lambda\ \sin(\psi)-\cos(\psi))$$

$$s13 = A\ (\sin(\phi)(F1/\lambda\ \sin(\psi)-\cos(\psi)-\cos((\psi)\cos(\theta)\\(F1/\lambda\ \cos(\psi)-\sin(\psi)))$$

$$s14 = (F0-F1)/\lambda$$

$$s21 = A(G1/\lambda(-\cos((\phi)*\cos(\psi)+\sin((\phi)\sin(\psi)\cos(\theta))+\\\sin(\theta)\sin((\phi))$$

$$s22 = A\ \cos((\phi)(G1/\lambda\ \sin(\theta)\sin(\psi)-\cos(\theta))$$

$$s23 = G1/\lambda A\ (\sin(\psi)\sin((\phi)-\cos(\psi)\cos(\theta)\cos((\phi))$$

$$s24 = (G0-G1)/\lambda$$

$$s31 = 0$$

$$s32 = -B\ \cos(\theta)(F2/\lambda\ \sin(\psi)-\cos(\psi))$$

$$s33 = -B\ \sin(\theta)(F2/\lambda\ \cos(\psi)+\sin(\psi))$$

$$s34 = (F0-F2)/\lambda$$

$$s41 = 0$$

$$s42 = -B(G2/\lambda\ \sin(\psi)\cos(\theta)+\sin(\theta))$$

$$s43 = -B\ G2/\lambda\ \sin(\theta)\cos(\psi)$$

$$s44 = (G0-G2)/\lambda$$

and the right hand side vector is defined as:

$$r1 = (F1-F0)z0/\lambda + A(F1/\lambda\ (\cos(\psi)\sin(\phi)+\cos(\theta)\ \cos((\phi)\\\sin(\psi))+\sin(\psi)\sin(\psi)-\cos(\theta)\cos((\phi)\cos(\psi))$$

$$r2 = (G1-G0)z0/\lambda + A(G1/\lambda\ (\cos(\psi)\sin(\phi)+\cos(\theta)\cos((\phi)\\\sin(\psi))+\sin(\theta)\cos((\phi))$$

$$r3 = (F2-F0)z0/\lambda + B\ \sin(\theta)(F2/\lambda\ \sin(\psi)-\cos(\psi))$$

$$r4 = (G2-G0)z0/\lambda + B(G2/\lambda\ \sin(\theta)\sin(\psi)-\cos(\theta))$$

After convergence the remaining parameters x0 and y0 are defined from the equations:

$$x0 = F0\ z0/\lambda$$

$$Y0 = G0\ z0/\lambda$$

The transition of pronounced colors can yield considerably more information than a black white transition, and is useful for the purpose of accurately calculating position and orientation of an object. As color cameras and high capacity processors become inexpensive, the added information provided can be accessed at virtually no added cost. And very importantly, in many cases color transitions are more pleasing to look at for the user than stark black and white. In addition the color can be varied within the target to create additional opportunities for statistically enhancing the resolution with which the target can be found.

Problems in 3Dimensional Input to Computers

Today, input to a computer for Three Dimensional (3D) information is often painstakingly done with a 2 Dimensional device such as a mouse or similar device. This artifice, both for the human, and for the program and its interaction with the human is un-natural, and CAD designers working with 3D design systems require many years of experience to master the skills needed for efficient design using same.

A similar situation exists with the very popular computer video games, which are becoming ever more 3 Dimensional in content and graphic imagery, but with similar limitations. These games too heretofore have not been natural for the player(s).

"Virtual reality" too requires 3D inputs for head tracking, movement of body parts and the like. This has lead to the development of a further area of sensor capability which has resulted in some solutions which are either cumbersome for the user, expensive, or both.

The limits of computer input in 3D have also restricted the use of natural type situations for teaching, simulation in medicine, and the like. It further limits young children, older citizens, and disabled persons from benefiting from computer aided living and work.

Another aspect is digitization of object shapes. There are times that one would like to take a plastic model or a real world part as a starting point for a 3D design. Prior art devices that capture 3D shapes are however, expensive and cumbersome and cannot, like the invention, share their function for replacement of the mouse or 2D graphic tablet.

We propose one single inexpensive device that can give all of this control and also act as a drawing pad, or input a 3D sculptured forms or even allow the user to use real clay that as she sculptures it the computer records the new shape.

The invention as here disclosed relates physical activities and physical objects directly to computer instructions. A novice user can design a house with a collection of targeted model or "toy" doors, windows, walls etc. By touching the appropriate toy component and then moving and rotating the user's hand she can place the component at the appropriate position. The user can either get his or her visual cue by looking at the position of the toy on the desk or by watching the corresponding scaled view on the computer display. Many other embodiments are also possible.

FIG. 2a

This figure illustrates an embodiment wherein the invention is used to "work" on an object, as opposed to pointing or otherwise indicating 30 commands or actions. It is a computer aided design system (CAD) embodiment according to the invention which illustrates several basic principles of optically aided computer inputs using single or dual/multi-camera (Stereo) photogrammetry. Illustrated are new forms of inputs to effect both the design and simulated assembly of objects.

3D Computer Aided Design (CAD) was one of the first areas to bump up against the need for new 3D input and control capability. A mouse or in the alternative, as 2D graphic tablet, together with software that displays several different views of the design are the current standard method. The drawback is that you are forced to move along 2D planes defined by display views or what are known as construction views of the design object.

This situation is especially frustrating when you start creating a design from scratch. The more sculptured the design, the more difficult this becomes. The current CAD experience feels more like an astronaut in a space suit with bulky fingertips and limited visibility trying to do delicate surgery.

A large number of specialized input devices have been designed to handle some of these problems but have had limited success. Just remember your own frustrations with the standard mouse. Imagine attempting to precisely and rapidly define and control complex 3D shapes all day, every day. This limits the usefulness of such design tools to only a relatively rare group, and not the population as a whole.

Ideally we want to return to the world we experience everyday where we simply reach our hand to select what we want to work with, turn it to examine it more closely, move and rotate it to a proper position to attach it to another object, find the right location and orientation to apply a bend of the proper amount and orientation to allow it to fit around another design object, capture 3D real work models, or stretch and sculpture designs.

One of the most wonderful properties of this invention is that it gives the user the ability to control not only 3D location with the motion of his hand but he also has 4 other pieces of data (3 orientation angles and time) that can be applied to control parameters. For example if we wanted to blend 2 designs (say a Ferrari and a Corvette) to create a new design, this process could be controlled simply by
1) moving the users hand from left to right to define the location of the cross section to be blended,
2) tilt the hand forward to defined the percentage "P" used to blend the 2 cross sections, and
3) hit the letter R on the keyboard to record items 1 and 2. From the each of the 2 cross sectional curves define a set of (x, y) coordinates and create a blended cross sectional coordinate set as follows:

$$X(\text{blend})=P*X(\text{Ferrari})+(1-P)*X(\text{Corvette})$$

$$Y(\text{blend})+P*Y(\text{Ferrari})+(1-P)*Y(\text{Corvette})$$

Note here and elsewhere, keystrokes can be replace if desired by voice commands, assuming suitable voice recognition capability in the computer.

In the apparatus of FIG. 1, we desire to use a touching and indicating device 216 with action tip 217 and multidegree of freedom enabling target 215 that the user holds in her hand. Single targets, or multiple targets can be used with a camera system such as 206 so as to provide up to 6 axis information of pointing device position and orientation vis a vis the camera reference frame, and by matrix transform, to any other coordinate system such as that of a TV display, 220.

In using the invention in the form, a user can send an interrupt signal from an "interrupt member" (such as pressing a keyboard key) to capture a single target location and orientation or a stream of target locations (ended with another interrupt). A computer program in computer determines the location and orientation of the target. The location and orientation of the "action tip": 217 of the pointing device can be computed with simple offset calculations from the location and orientation of the target or target set.

The set of tip 217 locations defines the 3D shape of the real world object 205. Different targeted tools with long or curved extensions to their action tips can be used to reach around the real world object while maintaining an attached target in the target volume so the cameras can record its location/orientation.

By lifting the tip of the pointing device off the surface of the object, the user can send location and orientation information to operate a computer program that will deform or modify the shape of the computer model displayed. Note that the user can deform a computer model even if there is no real world object under the tip. The tip location and orientation can always be passed to the computer program that is deforming the computer model.

The same device can be used to replace graphic tablets, mice, or white boards, or to be used in conjunction with a display screen, turning into a form of touch screen (as previously, and further discussed herein). In one mode Interrupt members can be activated (i.e. a button or keyboard key etc. can be pressed) like mouse buttons. These together with the target ID can initiate a computer program to act like a pen or an eraser or a specific paintbrush or spray can with width or other properties. The other target properties (z, or orientation angles) can be assigned to the computer program's pen, brush or eraser letting the user dynamically change these properties.

Target(s) can be attached to a users hand or painted on her nails using retroreflective nail polish paint for example allowing the user to quickly move their hand from the keyboard to allow camera or cameras and computer like that of FIG. 1 to determine the position and orientation in 2D or 3D of a computer generated object on the display, and to set the view direction or zoom, or input a set of computer parameters or computer instructions. This can all be done with the same device that we described in the above figures.

A major advantage is that this is done without having to grab a mouse or other device. Finger tips can be tracked in order to determine a relative movement such as a grasping motion of the fingers, further described in FIG. 6. Similarly the relation of say one finger, to the nail of the other hand can be seen.

Suitable indication can be the nail or natural image of the finger itself if suitable processing time and data processing power is available. However, as pointed our above, results today are expeditiously and economically best achieved by using easily identified, and preferably bright indicia such as retroreflective items, brightly colored or patterned items, unusually shaped items or a combination thereof.

One can also modify or virtually modify the thing digitized with the tools disclosed. The computer can both process the optical input and run the computer application software or a group of computers can process the optical data to obtain the location and orientation of the targets over time and pass that information to the application software in a separate computer.

The object 205 is shown being digitized with the simple pointer 216, though it could be different tools that could be used. For example, additional tools which could be used to identify the location and orientation of a 3D object are : a long stemmed pointer to work behind an object, pointers designed to reach into tight spaces, or around features, pointers to naturally slide over round surfaces, or planar corners. Each time the "activation member" is triggered, the camera system can capture the location and orientation of the target as well as its ID (alternatively one could enter the ID conventionally via a keyboard, voice or whatever. The ID is used to lookup in the associated database the location of the "work tip". The 3D coordinates can then be passed to the application software to later build the 3D data necessary to create a computer model of the object. When working on the back of the object furthest from the cameras, the object may obscure the camera view of the target on the simple tool. Thus the user may switch to the long stem tool or the curved stem tool that are used to get around the blocking geometry of the object. Other pointers can be used to reach into long crevices.

Let's examine the term "activation member". This can be any signal to the computer system that it should initiate a new operation such as collect one or more data points, or store the information, or lookup information in the associated databases, etc. Examples of the activation member are a button or foot pedal electronically linked to the computer, a computer keyboard whose key is depressed, or a trigger turning on a light or set of lights on a target, or a sound or voice activation.

Another method of acquiring a 3D shape is to slide a targeted tool over the object acquiring a continuous stream of 3D coordinates that can be treated as a 3D curve. These curves can later be processed to define the best 3D model to fit these curves. Each curve can be identified as either being an edge curve or a curve on the general body surface by hitting the previously defined keyboard key or other activation member.

This method is extremely powerful for capturing clay modeling as the artist is performing his art. In other words, each sweep of his fingers can be followed by recording the path of a target attached to his fingers. The target ID is used to lookup in the associated database the artists finger width and the typical deformation that his fingers experience on a sweep. He can change targets as the artwork nears completion to compensate for a lighter touch with less deformation.

FIG. 2b

Figure 2B:
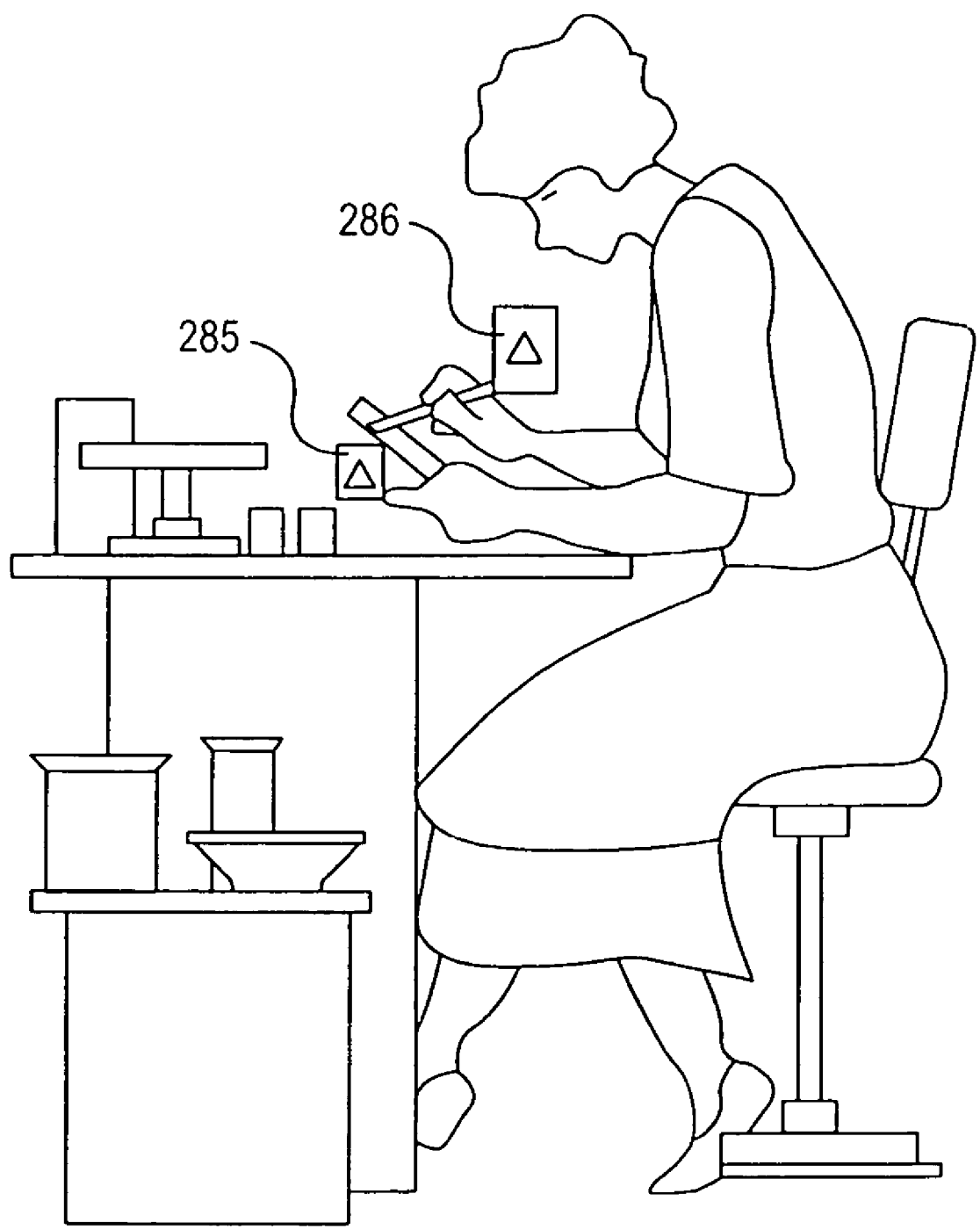
FIG. 2b describes another Computer Design embodiment with tactile feedback for "whittling " and other purposes.

FIG. 2b illustrates how targeted tools can be used in a CAD system or other computer program. A targeted work tool can be a toy model of the real world tool 280 (a toy drill for example) or the tool itself 281 (a small paint brush) helping the user immediately visualize the properties of the tool in the computer program. Note that any targeted tool can be "aliased" by another tool. For instance, the tip of the brush could be redefined inside the computer program to act like the tip of a drill. The location and orientation of the drill tip as well as the drill parameters such as its width can be derived from the target and together with its path and interrupt member information. The user can operate his CAD system as though he were operating a set of workshop or artist tools rather than traversing a set of menus.

The work tool and an object to be worked on can be targeted, and sensed either simultaneously or one after the other. Their relative locations and orientations can be derived allowing the user, for example, to "whittle" her computer model of the object 285 that she has in one hand with the tool 286 that is in the other hand.

Also a set of objects that are part of a house design process such as a door, a window, a bolt or a hinge could be defined quickly without having the user traverse a set of menus.

This device can perform an extremely broad range of input tasks for manipulation of 2D or 3D applications.

The devices that are used today for such activity are typically a mouse or a graphic tablet. Both of these devices really tend to work only in two dimensions. Everyone has had the experience with the mouse where it slips or skips over the mouse pad making it difficult to accurately position the cursor. The graphic tablet is somewhat easier to manipulate but it is bulky, covering up the desktop surface.

The disclosed invention can replace either of these devices. It never gets stuck since it moves in air. We can attach a target to the top of one of our hands or paint our fingernails and have them act as a target. Alternatively, for example we can pickup a pointing device such as a pencil with a target attached to the top of it. By merely moving our hand from side to side in front of the camera system we can emulate a mouse. As we move our hand forward and backward a software driver in our invention would emulate a mouse moving forward or backward, making input using known interface protocol straightforward. As we move our hand up and down off the table (something that neither the graphic tablet nor the mouse can do) our software driver can recognize a fully three-dimensional movement.

Much of the difficulty with computer-aided design software comes from ones inability heretofore to move naturally around our computer object. We see a three-dimensional design projected onto the two-dimensional computer display and we attempt to move around our three-dimensional design using two-dimensional input devices such as a mouse or computer graphic tablet. Design would be so much easier if we could simply move our hand in a three-dimensional region to both rotate and locate design information.

One Example of a Design Session Using this Invention

To more concretely describe this invention we will discuss one of many possible implementations:

painted fingernails on ones hand in that will act as the targets;

the computer keyboard will indicated which commands I am performing.

Targets can also be attached to objects, tools, and hands. Commands can be entered by voice, buttons, other member manipulations, or even by the path of a target itself.

An example of a sequence of actions is now described. The specific keys picked for this example are not a restriction of this invention. In a further embodiment other means of triggering events are disclosed than key board strokes.

An example of a sequence of actions is now described. The specific keys picked for this example are not a restriction of this invention. In a further embodiment other means of triggering events are disclosed than keyboard strokes.

Example of CAD Usage with Targeted Tools and Objects Together with Voice Recognition Activated Member Say "start" to begin using the invention.

Say "rotate View" and rotate the targeted hand inside the target volume until the view on the computer display is in the direction that you choose. In the same sense that a small motion of the mouse is scaled up or down to the useful motion in the design software, a small motion or rotation of the targeted hand can be scaled. Consider the target to be composed of three separate retroreflective fingernail targets. By rotating the plane formed by the three fingernails five degrees to the left we could make the display view on the screen rotate by say 45 degrees. We could also use the distance between ones fingers to increase or decrease the sensitivity to the hand rotation. This, if ones three fingers were close together a 5-degree turn of ones hand might correspond to a 5-degree turn on the screen, while if ones fingers were widely spread apart a 5-degree turn might correspond to 90-degree turn on the screen. Say "freeze view" to fix the new view.

Move the hand inside the target volume until a 3D cursor falls on top of at the display of a computer model and then say "select model".

Say "rotate model" and a rotation of the user's hand will cause the selected computer model to be rotated. Say "freeze model" to fix the rotation.

Say "Select grab point" to select a location to move the selected model by.

Say "move model" to move the selected model to a new location. Now the user can move this model in his design merely by moving his hand. When the proper location and orientation are achieved say "freeze model" to fix the object's position. This makes CAD assembly easy.

Say "start curve" and move the targeted hand through target volume in order to define a curve that can be used either as a design edge or as a path for the objects to follow. By moving the fingers apart in the user can control various curve parameters. Say "end curve" to complete the curve definition.

Pick up a model door that is part of a set of design objects each of which has its own unique target and target ID. Move the targeted object in the target volume until the corresponding design object in the software system is oriented and located properly in the design. Then say "add object". The location and orientation of the model door together with the spoken instruction will instruct the CAD program to create a door in the computer model. Moving the targeted fingers of apart can vary parameters that define the door such as height or width).

Pick up a targeted model window and say "add Object". The location and orientation of the model window together with the key hit will instruct the CAD program to create a window in the computer model.

Say "define Parameters" to define the type of window and window properties. The 3 location parameters, 3 orientation parameters, and the path motion, can be assigned by the database associated with the object to control and vary parameters that define the window in the computer software. Say "freeze parameters" to fix the definition.

Example: Designing a Car with Targeted Tools and Objects, Together with the Keyboard as the Member Giving Commands Now we apply this to the design of an automobile. The steps are as follows:

1. Pick up a model of a Corvette with a target attached to it and place it in the target volume.
2. Hit the A key (or provide another suitable signal to the computer, keys being representative of one type prevalent today) to the target parameters to define the object's parameters of interest such as model, year, and make.
3. Pick up a targeted pointer associated with the CAD commands to locating a car part to work on. The use of this specialized pointer target ID together with hitting the L key to define a view of the car where the orientation of the target defines the view orientation and the location of the camera. If the target defines a camera position inside the car the design information behind the camera will not be displayed. The motion of the special printer after the hit could indicate other commands without the use of a keyboard hit. For instance, a forward or backward tilt could increase or decrease the zoom magnification of the display. A large tilt to the left could select the object under the cursor and a large tilt to the right could deselect the object under the cursor. In a CAD system this selection could mean display that part for examination while in an inventory system it could mean display that part for examination while in an inventory system it could mean deliver this part.

Consider that part was hood selected for redesign in a CAD system. The user pick ups a targeted curvy wire. The invention will recognize the target ID as that of a curve line cross section command and when the user hits any key (or gives a voice command or other suitable signal) the location and orientation of the target is determined and the computer program will cause a cross section curve of the hood to be acquired at the corresponding location and orientation. The CAD system will then expect a series of keystrokes and target paths to define a new cross section leading to a modified hood design.

Hit the M key and draw a small curve segment to modify the previously drawn curve.

Hit the M key again to fix the modification.

Hit the F key to file down the hood where it seems to be too high. This is accomplished by moving the targeted fingers back and forth below some specified height above a surface (for example one-inch height above the desktop). The lower the fingers and move the target or targeted hand forward or backward. This can be linked to the surface definition in the CAD system causing the surface to be reduced as though a file or sander were being used. The lower the fingers the more material is removed on each pass. Likewise moving the fingers above one inch can be used to add material to the hood. Spreading the targeted fingers can increase the width of the sanding process.

A user can acquire 3D model (plastic, clay, etc.) by hitting the C key and either rub targeted fingers or a hand-held targeted sculpture tool over the model. From the path of the targeted fingers or tool we can compute the surface by applying the offset characteristics of the targeted too. If the 3D object is made of a deformable material such as clay, the CAD system can reflect the effect of the fingers or tool passing over the model on each passes. If we want we can add some clay on top of the model to build up material where we need it. Thus we can tie art forms such as clay modeling directly into CAD or other computer systems.

We can use targeted tools such as drills, knives, trowels, and scalpels to modify the clay model and its thus associated CAD model. The target ID will allow the computer to check the associated database to determine where the tip is relative to the target and define how the path of the target would result in the tool affecting the CAD model. Notice that we can use these tools in the same manner even if there's no clay model or other real world model to work on. Also notice that these tools could be simple targeted sticks but the CAD model would still be affected in the same way.

FIG. 3

Figure 3A:
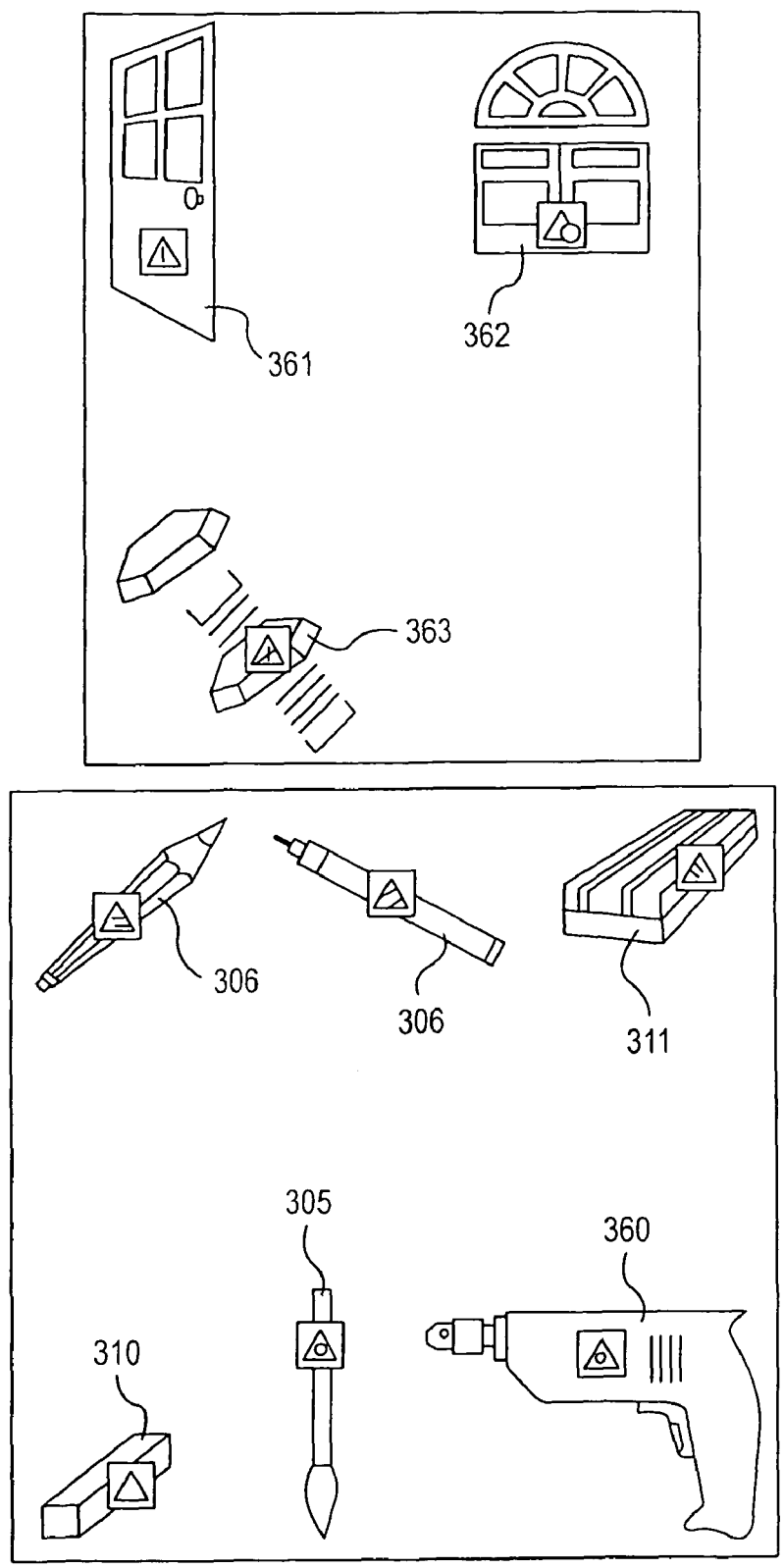
FIG. 3 illustrates additional embodiments working virtual objects, and additional alias objects according to the invention.
Figure 3B:
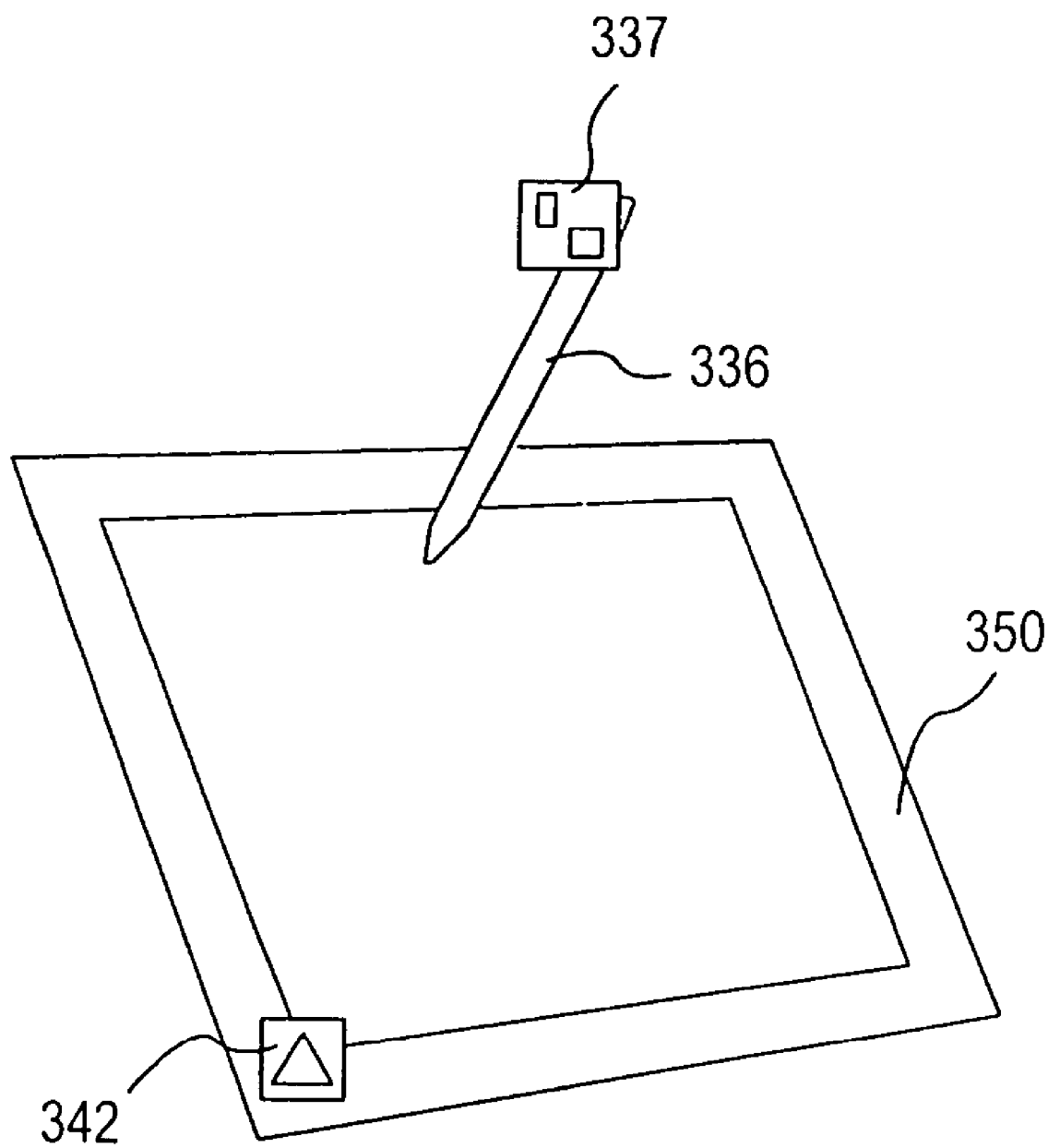

FIG. 3 illustrates additional embodiments working virtual objects, and additional alias objects according to the invention. For example a first object can be a pencil, with the Second object a piece of paper. It also illustrates how we can use of computer image determined tool position and orientation(targeted or otherwise) to give the user tactile and visual feedback as to how the motion, location, and orientation of the tool will affect the application computer program.

The user of the computer application program may have several tools that she feels comfortable with on her desk. An artist for instance might have a small paintbrush, a large paintbrush, a pen, an eraser, and a pencil. Each of these would have a unique target attached to it. The artist would then pick up the tool that she would normally use and draw over the surface of a sheet of paper or over the surface of display screen or projection of computer display. The application software would not only trace the path of the tip of the targeted work tool, but also treat the tool as though it were a pen or paintbrush etc. The exact characteristics of the pen would be found in the associated database using the target ID has a lookup key. Extra parameters such as the width of the line, its color, or whether it's a dashed line could be determined by keyboard input or by applying the height, or target orientation parameters.

If the artist did not own a tool that he needed he could "alias" this tool as follows. Suppose that the artist is missing a small paintbrush. He can pick up a pen move it into the target volume and signal the target acquisition software such as typing on the computer's keyboard the letter Q followed by the ID number of the small paintbrush. From this point on the computer will use the database us initiated with the small paintbrush instead of that of the pen.

Specifically we are illustrating several concepts:

This invention gives the user the natural tactile and visual feedback that she is used to and her art. Thus an artist would use targeted versions of the very tools such as pens 306, paintbrushes 305, and erasers 310 that she uses without a computer.

By drawing with a targeted tool (e.g. 336, having target 337) on a paper pad (e.g. 350 shown in FIG. 3b, with target 342) or canvas, the user again continues to experience the traditional non-computer art form as a computer interface. (targets in multiple corners of the paper can also be used for added resolution of paper location with respect to the tool) The user would see her art drawn on the paper while creating a computer version with all of the editing and reproduction capabilities implied by computers. The targeted tool's motion relative to the targeted paper is what determines the line in the graphics system. Thus the user could even put the pad in her lap and change her position in a chair and properly input the graphic information as she draws on the paper as long as the targets continue to be in the view of the camera system.

By drawing directly on a computer display, such as shown in FIG. 12, or transparent cover over a computer display, the user can make the targeted manipulate the computer display and immediately get feedback on how the graphics are effected. Again the art form will seem to match the traditional non-computer experience.

Parameters such as line width, or line type, etc. can be controlled by the target parameters that are not used to determine the path of the line (usually this would be the target height and orientation).

This invention allows the user to "alias" any object with any other object.

This invention allows users to control computer programs by moving targeted objects around inside the target volume rather than having to learn different menu systems for you each software package. Thus a child could quickly learn how to create 3D CAD designs by moving targeted toy doors 361, windows 362, drills 360, and pencils. With the use of macros found in most systems today, a user would create a hole in an object the same way on different CAD systems by moving say a tool such as a drill starting at the proper location and orientation and proceed to the proper depth.

An example of a Quant that could be used to define command in a CAD or drawing system to create a rectangle might be proceeded as follows:

Hit the Q key on the keyboard to start recording a Quant.

Sweep the target to the right punctuated with a short stationary pause. During the pause analyze the vector direction for the start of the path segment initiated with the Q key and ending with the pause. The first and last point of this segment define a vector direction that is mainly to the right with no significant up/down or in/out component. Identify this a direction 1.

Sweep the target upward punctuated with a short stationary pause. During the pause analyze the vector direction for the start of the path segment initiated with the last pause and ending with the next pause. The first and last point of this segment define a vector direction that is mainly upward with no significant left/right or in/out component. Identify this a direction 2.

Sweep the target to the left punctuated with a short stationary pause. During the pause analyze the vector direction for the start of the path segment initiated with the last pause and ending with the next pause. The first a last point of this segment define a vector direction that is mainly to the left with no significant up/down or in/out component. Identify this a direction 3.

Sweep the target down punctuated with a short stationary pause. During the pause analyze the vector direction for the start of the path segment initiated with the last pause and ending with the next pause. The first and last point of this segment define a vector direction that is mainly down with no significant left/right or in/out component. Identify this a direction 4.

End the Quant acquisition with a key press "a" that gives additional information to identify how the Quant is to be used.

In this example the Quant might be stored as a compact set of 7 numbers and letters (4, 1, 2, 3, 4, a, 27) where 4 is the number of path segments, 1-4 are number that identify path segment directions (i.e. right, up, left, down), "a" is the member interrupt (the key press a), and 27 is the target ID. FIG. 7a illustrates a flow chart as to how target paths and Quants can be defined.

FIG. 4

Figure 4:
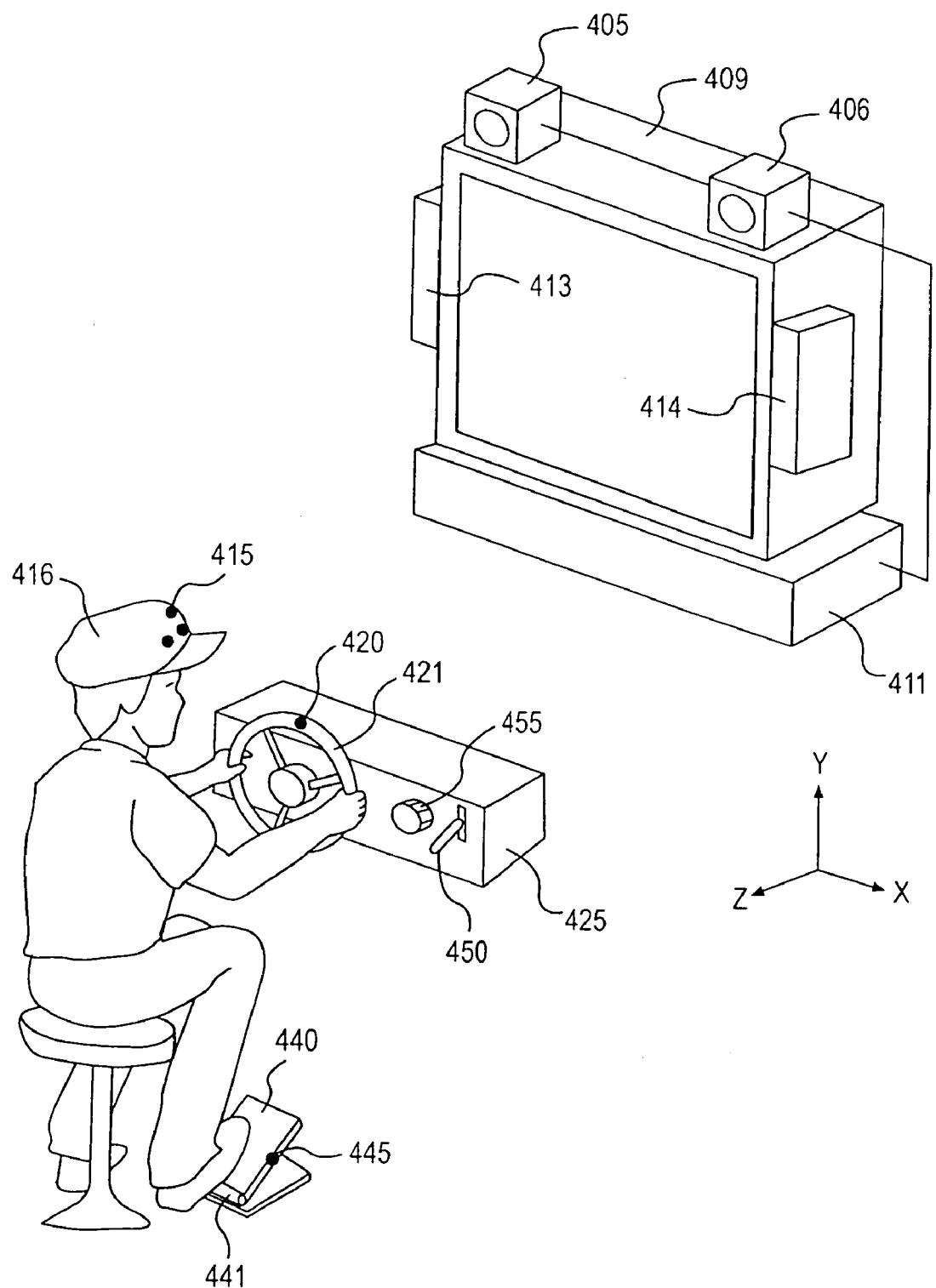
FIG. 4 illustrates a car driving game embodiment of the invention, which in addition illustrates the use of target-based artifacts and simplified head tracking with viewpoint rotation. The car dash is for example a plastic model purchased or constructed to simulate a real car dash, or can even be a make-believe dash (i.e. in which the dash is made from for example a board, and the steering wheel from a dish), and the car is simulated in its actions via computer imagery and sounds.

FIG. 4 illustrates a car driving game embodiment of the invention, which in addition illustrates the use of target-based artifacts and simplified head tracking with viewpoint rotation.

The car dash is for example a plastic model purchased or constructed to simulate a real car dash, or can even be a make-believe dash (i.e. in which the dash is made from for example a board, and the steering wheel from a wheel from a wagon or other toy,—or even a dish), and the car is simulated in its actions via computer imagery and sounds.

Cameras 405 and 406 forming a stereo pair, and light sources as required (not shown) are desirably mounted on rear projection TV 409, and are used together with computer 411 to determine the location and orientation of the head of a child or other game player. The computer, provides from software a view on the screen of TV 409 (and optionally sound, on speakers 413 and 414) that the player would see as he turns his head—e.g. right, left, (and optionally, up, down—not so important in a car game driven on horizontal plane, but important in other games which can be played with the same equipment but different programs). This viewpoint rotation is provided using the cameras to determine the orientation of the head from one or more targets 415 attached to the players head or in this case, a hat 416.

In addition, there desirably is also target 420 on the steering wheel which can be seen by stereo pair of cameras 405 and 406. As the wheel is turned, the target moves in a rotary motion which can be transduced accordingly, or as a compound x and y motion by the camera processor system means in computer 411. It is noted that The target 420 can alternately be attached to any object that we chose to act as a steering wheel 421 such as the wheel of a child's play dashboard toy 425.

A prefabricated plywood or plastic molded for dash board can be supplied having other controls incorporated, e.g. gas pedal 440 hinged at bottom with hinge 441, and preferably providing an elastic tactile feedback, has target 445 viewed by cameras 405 and 406 such that y axis position and/or z axis (range) changes as the player pushes down on the pedal. This change is sensed, and determined by TV based stereo photogrammetry using the cameras and computer, which data is then converted by computer 412 into information which can be used to modify the display or audio signals providing simulations of the cars acceleration or speed depicted with visual and auditory cues.

Similarly, a brake pedal or any other control action can be provided, for example moving a dashboard lever such as 450 sideways (moving in this case a target on its rear facing the camera not shown for clarity, in x axis motion), or turning a dashboard knob such as 455(rotating a target, not shown, on its rear facing the camera).

Alternatively to purchasing or fabricating a realistic dashboard simulation toy, the child can use his imagination with the same game software. Ordinary household objects such as salt shakers with attached targets can serve as the gas pedal, gearshift, or other controls. A dish with a target, for example can created by the invention to represent a steering wheel, without any other equipment used. This makes fun toys and games available at low cost once computers and camera systems become standard due to their applicability to a wide variety of applications, at ever lower hardware cost due to declining chip prices.

One camera system (single or stereo pair or other ) can be used to follow all of the targets at once or several camera systems can follow separate targets.

To summarize this figure we have shown the following ideas:
1) This invention can turn toys or household objects into computer controls or game controls. This is most easily accomplished by attaching one or more special targets to them, though natural features of some objects can be used.

2) This invention allows us to set up control panels or instrument panels as required without the complex mechanical and electrical connections, and transducers that are typically required. This lowers the cost and complexity dramatically.
3) The invention allows simplified head tracking with viewpoint rotation.

Some further detail on the embodiment of FIG. 4, wherein a boy is seated in front of a low cost plastic or plywood dashboard to which a targeted steering wheel and gas and brake pedal is attached (also gear shifts, and other accessories as desired). A target on the boys hat is observed, as are the targets on the individual items of the dash, in this case by stereo pair of cameras located atop the TV display screen, which is of large enough size to seem real—for example, the dash board width is preferable. Retro-reflective tape targets of scotch light 7615 material are used, illuminated by light sources in close adjacency to each camera.

Optionally a TV image of the boy's face can also be taken to show him at the wheel, leaning out the window (likely imaginary)etc.

As noted previously, the boy can move his head from left to right and the computer change the display so he sees a different view of his car on the track, and up and down, to move from driver view of the road, to overhead view of the course, say.

Stereo cameras may be advantageously located on a television receiver looking outward at the back of an instrument panel, having targeted levers and switches and steering wheel, etc. whose movement and position is determined along with that of the player, if desired. The panel can be made out of low cost wood or plastic pieces. The player can wear a hat with targets viewed—same field of view as ins. Panel—this allows all data in one view. As he moves his head to lean out the car window so to speak, the image on screen moves view (typically in an exaggerated manner, like a small angular head movement, might rotate the view 45 degrees in the horizontal or vertical direction on the screen).

This invention allows one to change the game from cars to planes just by changing the low cost plastic or wood molded toy instrument panel with its dummy levers, switches, sliders, wheels, etc. These actuating devices are as noted desirably for easiest results, targeted for example by high visibility and of accurately determinable position, retroreflector or led targets. The display used can be that of the TV, or separately incorporated (and preferably removable for use in other applications), as with an LCD (liquid crystal display) on the instrument panel. Multi-person play is possible, and can be connected remotely.

Of significance, is that all datum's useable in this toy car driving simulation game, including several different driver body point inputs, head position and orientation, steering wheel position, plus driver gray level image and perhaps other functions as well, can all be observed with the same camera or multi-camera stereo camera set. This is a huge saving in cost of various equipment otherwise used with high priced arcade systems to deliver a fraction of the sensory input capability. The stereo TV image can also TV images which can be displayed in stereo at another site if desired too.

Where only a single camera is used to see a single point, depth information in z (from panel to camera, here on the TV set as shown in FIG. 4) is not generally possible. Thus steering wheel rotation is visible as an x-y movement in the image field of the camera, but the gas pedal lever must be for example hinged so as to cause a significant x and/or y change not just a predominantly z change.

A change in x and/or y can be taught to the system to represent the range of gas pedal positions, by first engaging in a teach mode where one can as shown in FIG. 4 input a voice command to say to the system that a given position is gas pedal up, gas pedal down (max throttle) and any position in between. The corresponding image positions of the target on the gas pedal lever member re recorded in a table and looked up ( or alternatively converted to an equation) when the game is in actual operation so that the gas pedal input command can be used to cause imagery on the screen (and audio of the engine, say)to give an apparent speedup or slowing down of the vehicle. Similarly the wheel can be turned right to left, with similar results, and the brake pedal lever and any other control desired can also be so engaged. (as noted below, in some cases such control is not just limited to toys and simulations and can also be used for real vehicles).

The position, velocity, and rate of change of targeted member positions can also be determined, to indicate other desirable information to the computer analyzing the TV images.

Where stereo image pairs are used, the largest freedom for action results as z dimension can also be encoded. However many control functions are unidirectional, and thus can be dealt with as noted above using a single camera 2D image analysis.

On a broader scale, this aspect of the invention allows one to create 3D physical manifestations of instruments in a simulation form, much as National Instruments firm has pioneered two dimensional TV screen only displays. In addition such an "instrument panel" can also be used to interact with conventional programs—even word processing, spreadsheets and the like where a lever moved by the user might shift a display window on the screen for example. A selector switch on the panel can shift to different screens altogether, and so forth.

FIG. 4 has also illustrated the use of the invention to create a simple general-purpose visual and tactile interface to computer programs.

FIG. 5

Figure 5A:
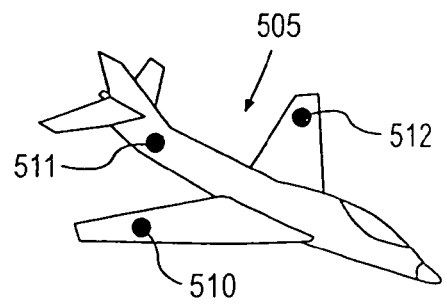
FIG. 5a depicts a targeted airplane and FIG. 5b illustrates a one or two person airplane game using the targeted airplane of FIG. 5a according to the invention, to further include inputs for triggering and scene change via movement sequences or gestures of a player. Also illustrated in FIG. 5c is a hand puppet game embodiment of the invention played if desired over remote means such as the Internet.

FIG. 5a illustrates a one-person game where a targeted airplane model 505 can be used to define the course of an airplane in a game. The orientation of the plane, determined from targets 510, 511, and 512 (on the wings and fuselage respectively) by camera(s) 530 is used by program resident in computer 535 to determine its position and orientation, and changes therein due to movement in the game. The model can be purchased pre targeted (where natural features such as colored circles or special retroreflectors might be used for example). The planes position and/orientation or change therein is used as an input to a visual display on the computer display and audio program to provide realistic feeling of flight—or alternatively to allow the computer to stage a duel, wherein an the opposing fighter is created in the computer and displayed either alone, or along with the fighter represented by the player. It is particularly enhanced when a large screen display is used, for example >42 inches diagonal.

Figure 5B:
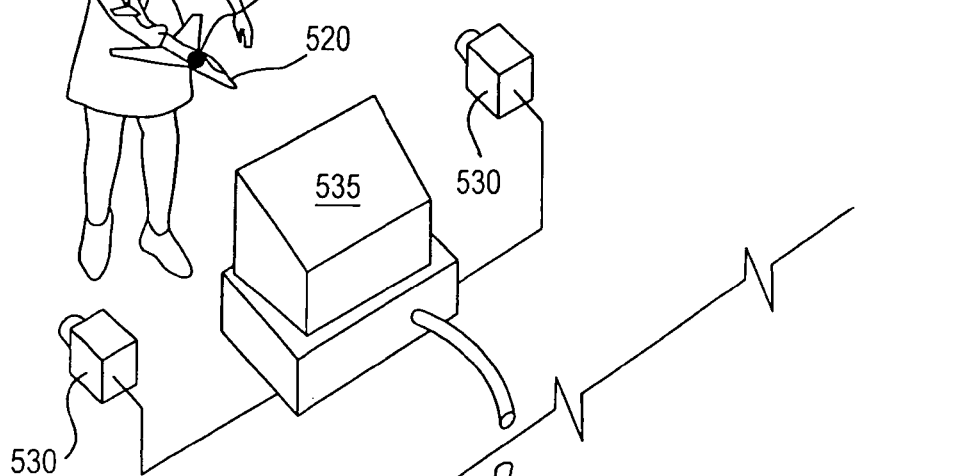
Figure 5B:
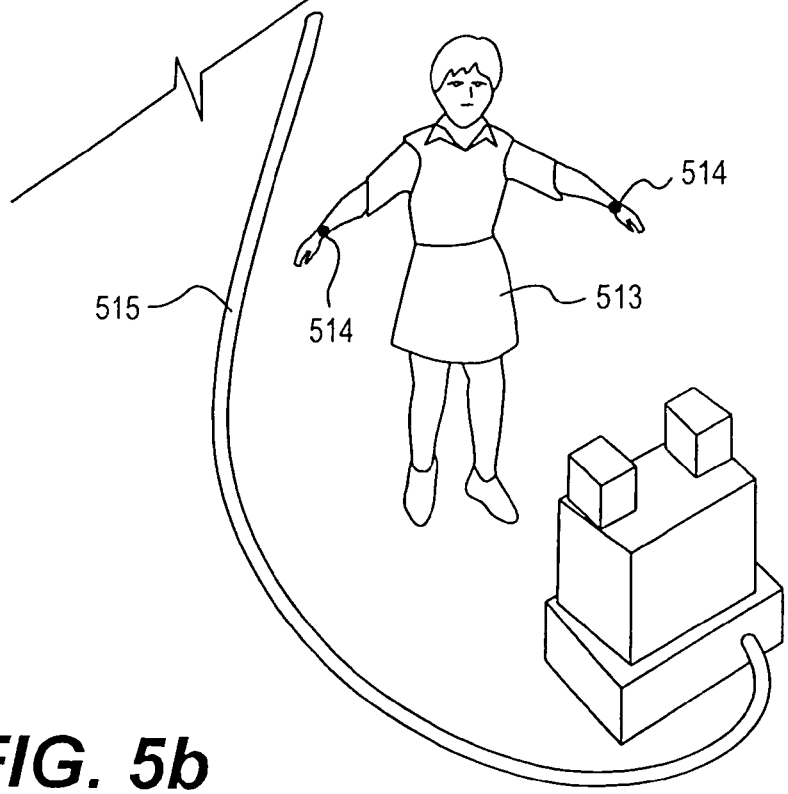

A two person version in shown in FIG. 5b where the two computers can be linked over the internet or via a cable across the room. In the two-person game airplane 510 is targeted 511 and the motion is sent over a communication link 515 to a second computer where another player had her airplane 520 with its target. The two results can be displayed on each computer display allowing the users to interactively modify their position and orientation. An interrupt member can trigger the game to fire a weapon or reconfigure the vehicle. A set of targets 514 can even be attached (e.g. with Velcro, to his hands or wrists, and body or head) to the player 513 allowing her to "become" the airplane as he moves around in the front of the cameras. This is similar to a child today, pretending to be an airplane, with arms outstretched. It is thus a very natural type of play, but with exciting additions of sounds and 3D graphics to correspond to the moves made.

For example, if the child's arms tilt, to simulate a bank of the plane, a plane representation such as an F16 on the screen can also bank.

If the child moves quickly, the sounds of the jet engine can roar.

If the child moves his fingers, for example, the guns can fire.

And so forth. In each case a position or movement of the child, is sensed by the camera, compared by the computer program to programmed or taught movement or position, and the result used to activate the desired video and/or audio response—and to transmit to a remote location if desired the positions and movements either raw, or in processed mode (i.e. a command saying "bank left" could just be transmitted, rather than target positions corresponding thereto).

Figure 5C:
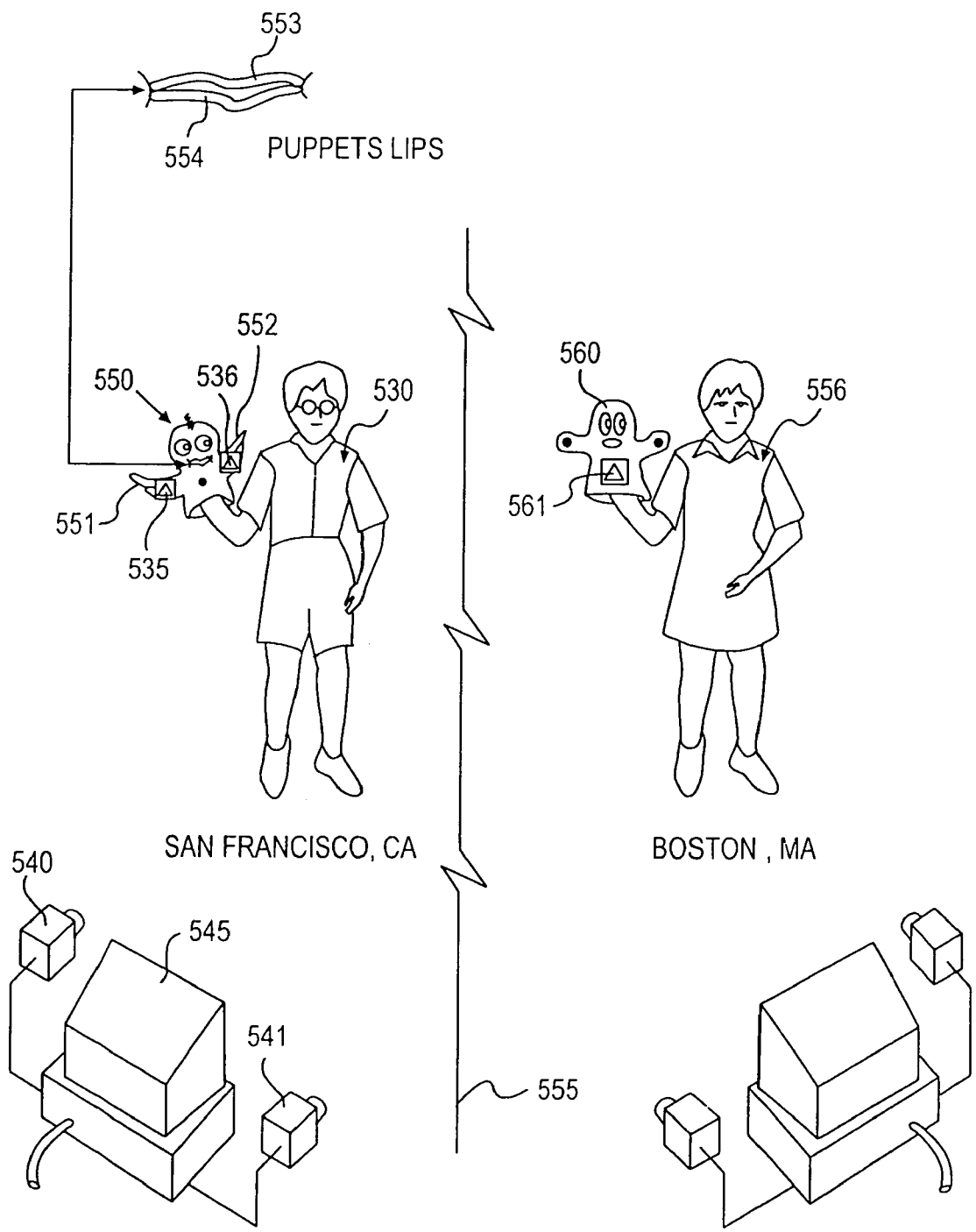

Also illustrated in FIG. 5c is a one or multi-person "Big Bird" or other hand puppet game embodiment of the invention played if desired over remote means such as the Internet. It is similar to the stuffed animal application described above, except that the players are not in the same room. And, in the case of the Internet, play is bandwidth limited, at least today.

Child 530 plays with doll or hand puppet 550, for example Sesame Streets' "Big Bird", can be targeted using targets 535 and 540 on its hands 551 and 552 and curvilinear line type target 553 and 554 outlining its upper and lower lips (beak). Target motion sensed by stereo pair of cameras 540 and 541 is transformed by computer 545 into signals to be sent over the internet 555 or through another communication link to allow a second child 556 to interact, moving his doll 560 with say at least one target 561.

In the simplest case, Each user controls one character. The results of both actions can be viewed on each computer display.

It is noted that a simple program change, can convert from an airplane fighter game, to something else—for example pretending to be a model on a runway, (where walking perfectly might be the goal), or dolls that could be moved in a TV screen representation doll house—itself selectable as the White House, Buckingham Palace or what ever.

We have depicted a one or two person airplane game according to the invention, to further include inputs for triggering and scene change via movement sequences or gestures of a player. Further described are other movements such as gripping or touch indicating which can be useful as input to a computer system.

The invention comprehends a full suite of up to 6 degrees of freedom gesture type inputs, both static, dynamic, and sequences of dynamic movements.

FIG. 6

Figure 6:
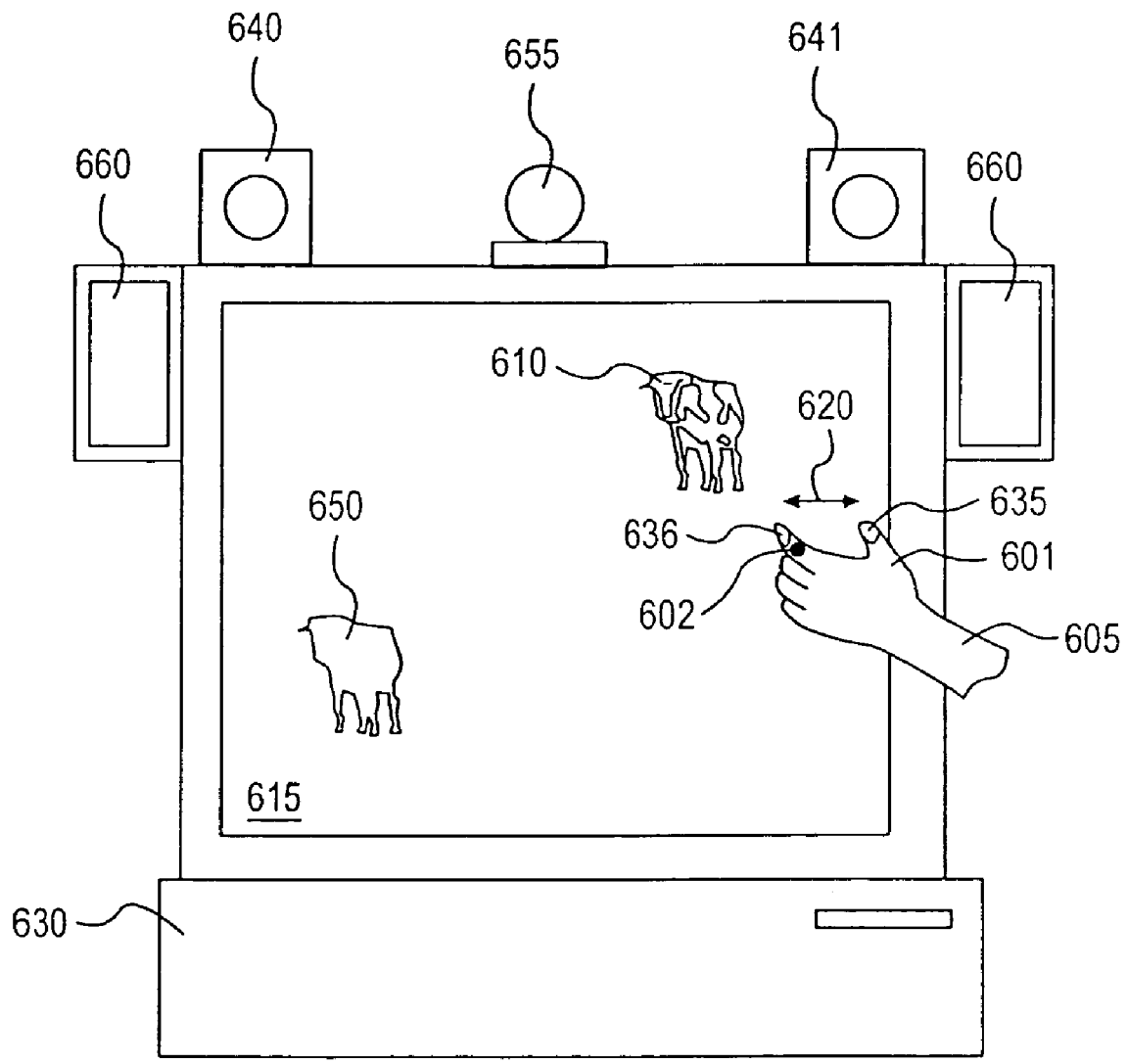
FIG. 6 illustrates other movements such as gripping or touch which can be sensed by the invention indicating which can be useful as input to a computer system, for the purpose of signaling that a certain action is occurring.

FIG. 6 illustrates other movements such as gripping or touch indicating which can be useful as input to a computer system. Parts of the user, such as the hands can describe motion or position signatures and sequences of considerable utility.

Some natural actions of this type (learned in the course of life):Grip, pinch, grasp, stretch, bend, twist, rotate, screw, point, hammer, throw.

Some specially learned or created actions of this type: define parameter, (for example, fingers wide apart, or spaced narrow) flipped up targets etc on fingers—rings, simple actuated object with levers to move targets.

This really is a method of signaling action to computer using Detected position of one finger, two fingers of one hand, one finger of each hand, two hands, or relative motion/position of any of the above with respect to the human or the computer camera system or the screen (itself generally fixed with respect to the camera system).

These actions can cause objects depicted on a screen to be acted on, by sensing using the invention. For example, consider the thumb 601 and first finger 602 of lets say the users left hand 605 are near an object such as a 3D graphic rendition of a cow 610 displayed on the screen, 615, in this case hung from a wall, or with an image projected from behind thereon. As the fingers are converged in a pinching motion depicted as dotted lines 620, the program of computer 630 recognizes this motion of fingernails 635 and 636 seen by cameras 640 and 641 connected to the computer which processes their image, as a pinch/grasp motion and can either cause the image of the cow to be compressed graphically, or if the hand is pulled away with in a certain time, it is a interpreted to be a grasp, and the cow object is moved to a new location on the screen where the user deposits it, for example at position 650 (dotted lines). Or it could be placed "in the trash".

A microphone 655 can be used to input voice commands into the computer 630 which can then using known technology (dragon software, IBM via voice, etc) be used to process the command. A typical command might be grip, move, etc, if these weren't obvious from the detected motion itself.

In a similar manner, speakers 660 controlled by the computer can give back data to the user such as a beep when the object has been grasped. Where possible for natural effect, it is desirable that where sound and action coincide—that is a squishing sound when something is squished, for example.

If two hands are used, one can pinch the cow image at each end, and "elongate it" in one direction, or bend it in a curve, both motions of which can be sensed by the invention in 3 dimensions—even though the image itself is actually represented on the screen in two dimensions as a rendered graphic responding to the input desired. (via action of the program).

The Scale of grip of fingers depends on range from screen (and object thereon being gripped) desirably has a variable scale factor dependent on detected range from the sensor (unless one is to always touch the screen or come very near it to make the move).

Pinching or Gripping is very useful in combination with voice for word processing and spreadsheets. One can move blocks of data from one place to another in a document, or from one document to the next. One can very nicely use it for graphics and other construction by gripping objects, and pasting them together, and then rotating them or whatever with the finger motions used sensed by the invention.

Figure 7:
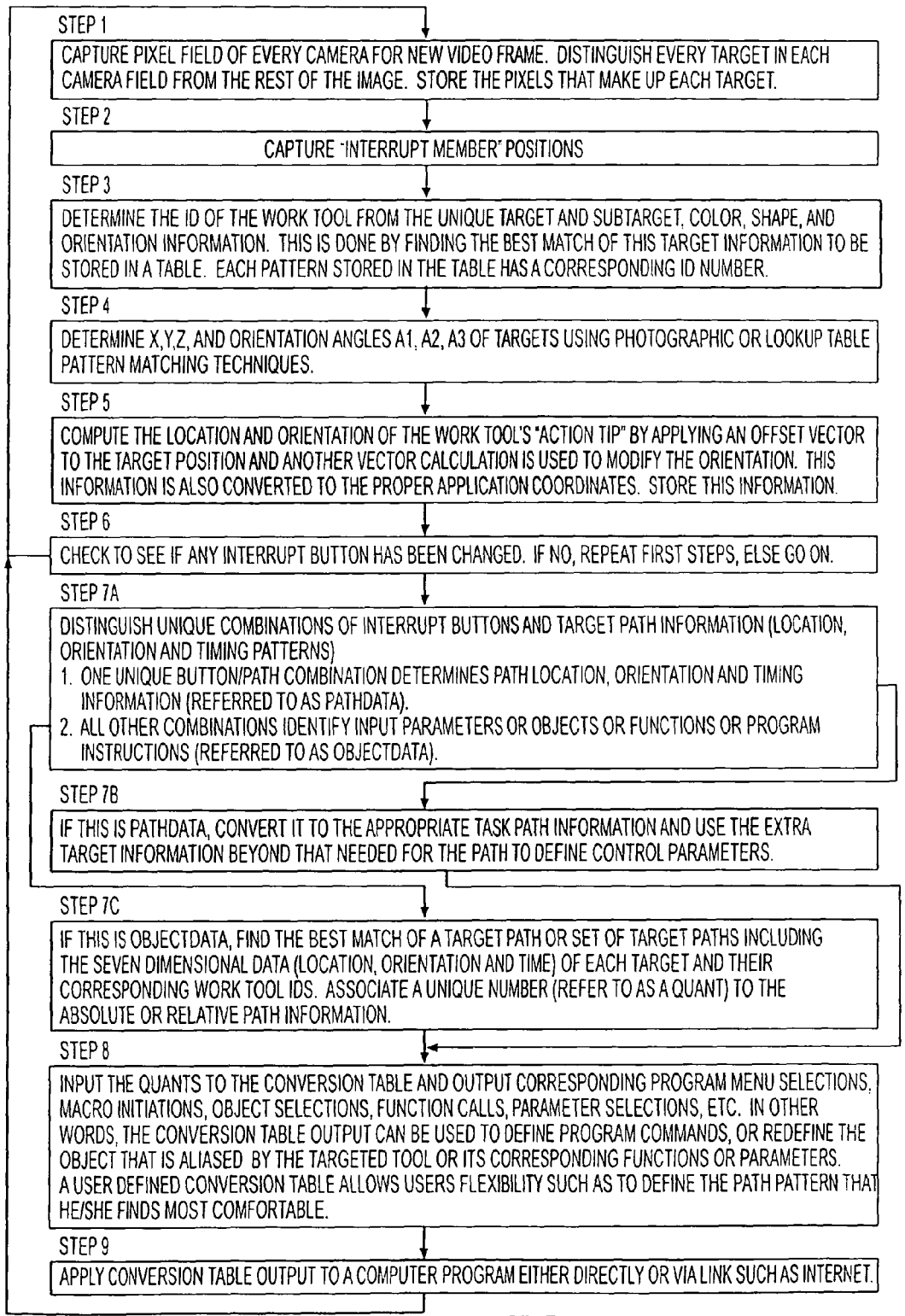
FIG. 7 illustrates further detail as to the computer architecture of movement sequences and gestures, and their use in computer instruction via video inputs. Also illustrated are means to determine position and orientation parameters with minimum information at any point in time.

Similarly to the pinching or grasping motion just described, some other examples which can also be sensed and acted on with the invention, using either the natural image of the fingers or hands, or of specialized datums thereon, are:

Point
Move
Slide
grip
Pull apart, stretch, elongate
Push together, squeeze
Twist, screw, turn
Hammer
Bend
Throw FIG. 7 (Block diagram)

FIG. 7 illustrates the use of this invention to implement an optical based computer input for specifying software program commands, parameters, define new objects or new actions in an application computer program, temporarily redefine some or all of the database associated with the target or call specific computer programs, functions, or subroutines.

A sequence of simple path segments of the targets obtained by this invention separated by "Quant punctuation" together with its interrupt member settings and its target ID can define a unique data set. We refer to this data set as a "Quant" referring to the discrete states (much like quantum states of the atom). The end of each path segment is denoted with a "Quant punctuation" such as radical change in path direction or target orientation or speed or the change in a specific interrupt member or even a combination of the above. The path segments are used to define a reduced or quantized set of target path information.

A Quant has an associated ID (identification number) which can be used as a look-up key in an associated database to find the associated program commands, parameters, objects, actions, etc. as well as the defining characteristics of the Quant.

An example of a Quant that could be used to define command in a CAD or drawing system to create a rectangle might be proceeded as follows:

A. Hit the Q key on the keyboard to start recording a Quant.
B. Sweep the target to the right punctuated with a short stationary pause. During the pause analyze the vector direction for the start of the path segment initiated with the Q key and ending with the pause. The first and last point of this segment define a vector direction that is mainly to the right with no significant up/down or in/out component. Identify this a direction 1.
C. Sweep the target upward punctuated with a short stationary pause. During the pause analyze the vector direction for the start of the path segment initiated with the last pause and ending with the next pause. The first and last point—of this segment define a vector direction that is mainly upward with no significant left/right or in/out component. Identify this a direction 2.
D. Sweep the target to the left punctuated with a short stationary pause. During the pause analyze the vector direction for the start of the path segment initiated with the last pause and ending with the next pause. The first a last point of this segment define a vector direction that is mainly to the left with no significant up/down or in/out component. Identify this a direction 3.
E. Sweep the target down punctuated with a short stationary pause. During the pause analyze the vector direction for the start of the path segment initiated with the last pause and ending with the next pause. The first and last point of this segment define a vector direction that is mainly down with no significant left/right or in/out component. Identify this a direction 4.
F. End the Quant acquisition with a key press "a" that gives additional information to identify how the Quant is to be used.
G. In this example the Quant might be stored as a compact set of 7 numbers and letters (4, 1, 2, 3, 4, a, 27) where 4 is the number of path segments, 1-4 are number that identify path segment directions (i.e. right, up, left, down), "a" is the member interrupt (the key press a), and 27 is the target ID. FIG. 7a illustrates a flow chart as to how target paths and Quants can be defined.
H. In another example, the continuous circular sweep rather than punctuated segments might define a circle command in a CAD system. Some Quants might immediately initiate the recording of another Quant that provides the information needed to complete the prior Quant instruction.
I. Specific Quants can identify a bolt and its specific size, and thread parameters together with information as to command a computer controlled screwing device or drilling a hole for this size bolt. Another Quant could identify a hinge and;
J. Define a CAD model with the specific size, and manufacture characteristics defined by Quant.
K. Or assign joint characteristics to a CAD model.
L. Or command a computer controlled device to bend an object at a given location and orientation by a given location and orientation amount.
M. This method can be applied to sculpture where the depth of a planar cut or the whittling of an object can be determined by the characteristics of the targeted object's path (in other words by it's Quant).

FIG. 8

FIG. 8 illustrates the use of this invention for medical applications. A user can apply this invention for teaching medical and dental students, or controlling robotic equipment used for example in medical and dental applications. In addition, it can be used to give physically controlled lookup of databases and help systems.

Figure 8A:
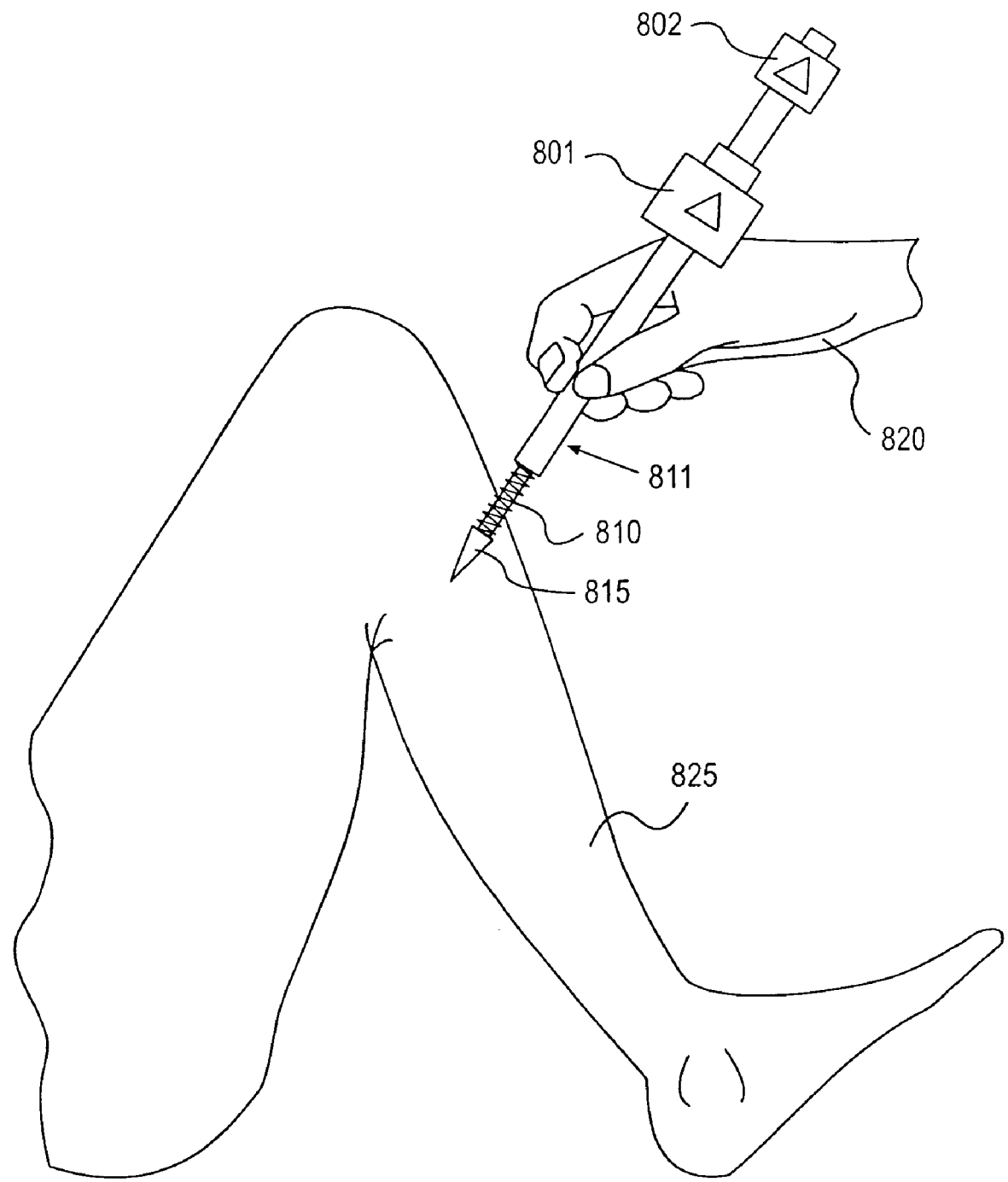
FIG. 8a illustrates a targeted scalpel used by a medical student for simulated surgery, further including a compressible member for calculating out of sight tip locations.

In FIG. 8a, somewhat similar to FIG. 1 above, a scalpel has two targets 801, and 802 (in this case triangular targets) allowing a 6 degree of freedom solution of the position and orientation of a scalpel 811 to which it is attached, having a tip 815. Other surgical instruments can also be used, each with their own unique targets and target ID's, if desired, to allow their automatic recognition by the electro-optical sensing system of the invention.

The figure shows a medical student's hand 820 holding a model of a surgical instrument, a scalpel. A model of a body can be used to call up surgical database information in the computer attached to the camera system about the body parts in the vicinity of the body model 825 being touched. If the targeted tool is pressed down compressing the spring 810 and moving the targets 801 and 802 apart, the information displayed can refer to internal body parts. As the user presses down harder on the spring, the greater the targets move apart the lower in the body and this can be used to instruct the database to display the computer that we reach for information. If the user wants to look up information on drugs that are useful for organs in a given region in the body he might use a similar model syringe with a different target having a different ID. In a similar way a medical (or dental) student could be tested on his knowledge of medicine by using the same method to identify and record in the computer location on the body that is the answer to a test question. Similarly the location and orientation of the targeted tool can be used to control the path of a robotic surgery tool.

Notice that the tool with a spring gives the user tactile feedback. Another way the user can get tactile feedback is to use this pointer tool on a pre-calibrated material that has the same degree of compression or cutting characteristics as the real body part.

In a preferred embodiment, each surgical device has its own unique target and its own unique target ID. One of the unique features of this invention is that the user can use the fact surgical tool that he uses normally in the application of his art. Thus, a dental student can pick up a standard dental drill and the target can be attached to a dental drill that has the same feel as an ordinary drill.

Figure 8B:
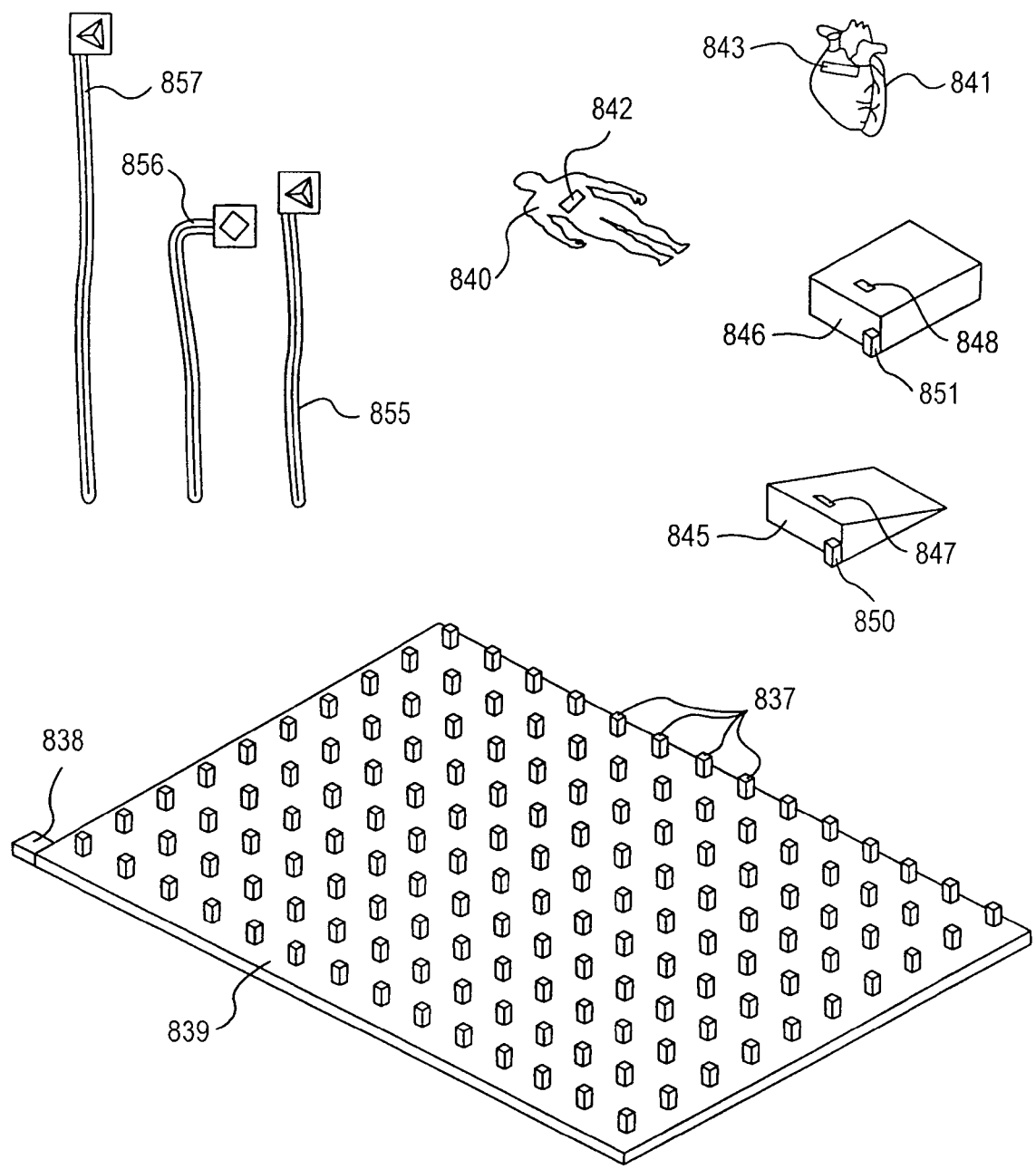
FIG. 8b depicts how several objects can be attached to specialized holders that are then attached to a baseboard to create a single rigid collection mechanism.

FIG. 8b show how several objects can be attached to specialized holders that are then attached to a baseboard to create a single rigid collection whose location and orientation can be pre-registered and stored in a computer database such that only a single targeted pointer or tool need be tracked. The baseboard has one or more specialized target attachment locations. We consider two types of baseboard/holder attachments, fixed (such as pegboard/hole) or freeform (using for example magnets or Velcro). Charts 8*d* and 8*e* describe how these might be calibrated.

Attachable targets can be used to pre-register the location and orientation of 1 or more objects relative to a camera system and to each other using a baseboard 839 shown here with square pegs 837 and an attachment fixture 838 that will hold a specialized target such as those shown as 855, 856, 857. A set of objects here shown as a model of a body 840 and a model of a heart 841 with attachment points 842 and 843 that are attached to object holders 845 and 846 at attachment points 847 and 848. The object holders can be of different shapes allowing the user to hold the object at different orientations and positions as desired. Each object holder has an attachment fixture 850 and 851 that will hold a specialized target. The user then picks the appropriate target together with the appropriate fixture on the object holder so that the target is best positioned in front of the camera to capture the location and orientation of the target. Chart 8*d* and 8*e* describe the calibration process for a fixed and freeform attachment implementation respectively. Once the baseboard and targets have been calibrated, a computer program can identify which object is being operated on and determine how this information will be used. The steps for utilizing this system is described in Chart 8*f*.

Figure 8C:
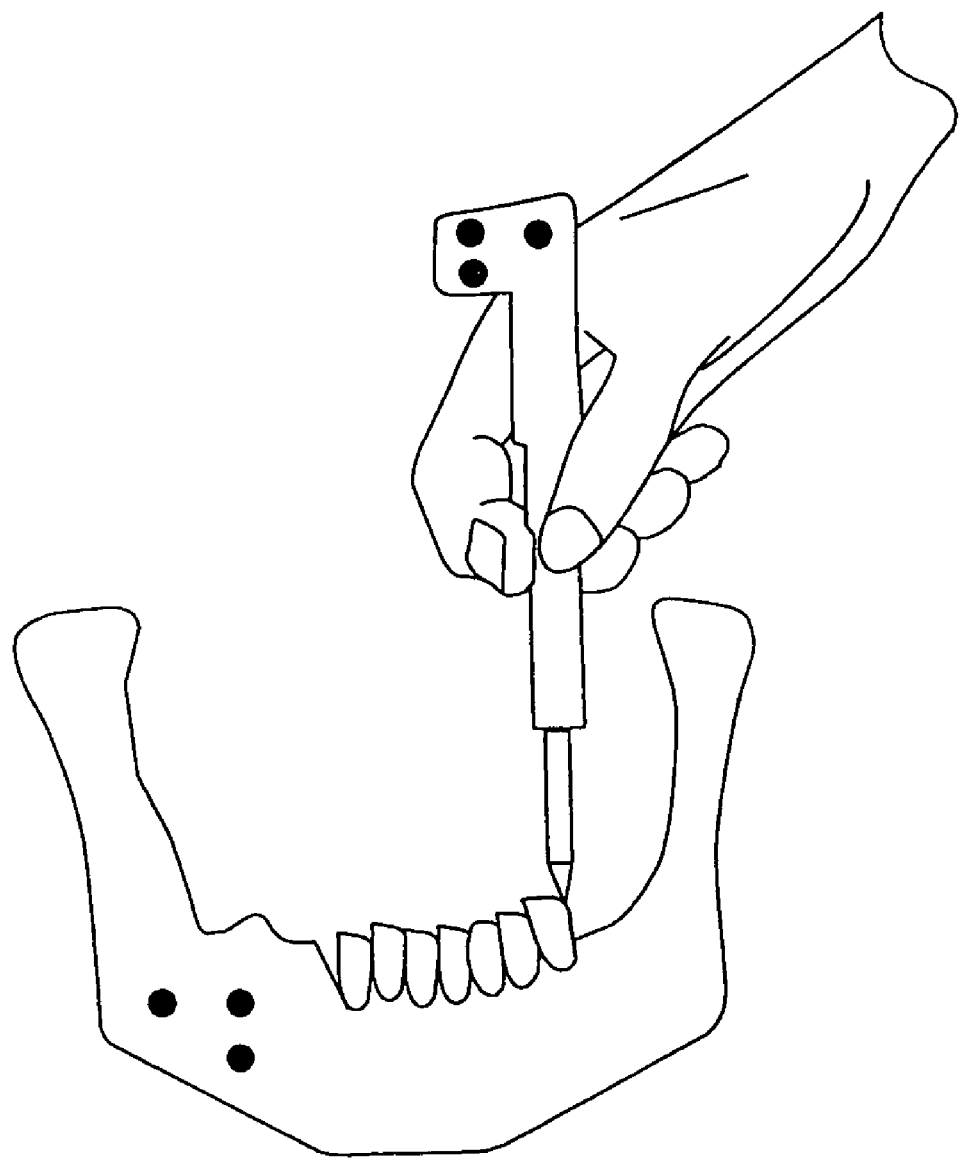
FIG. 8c illustrates targeted instruments and targeted body model.
Figure 8D:
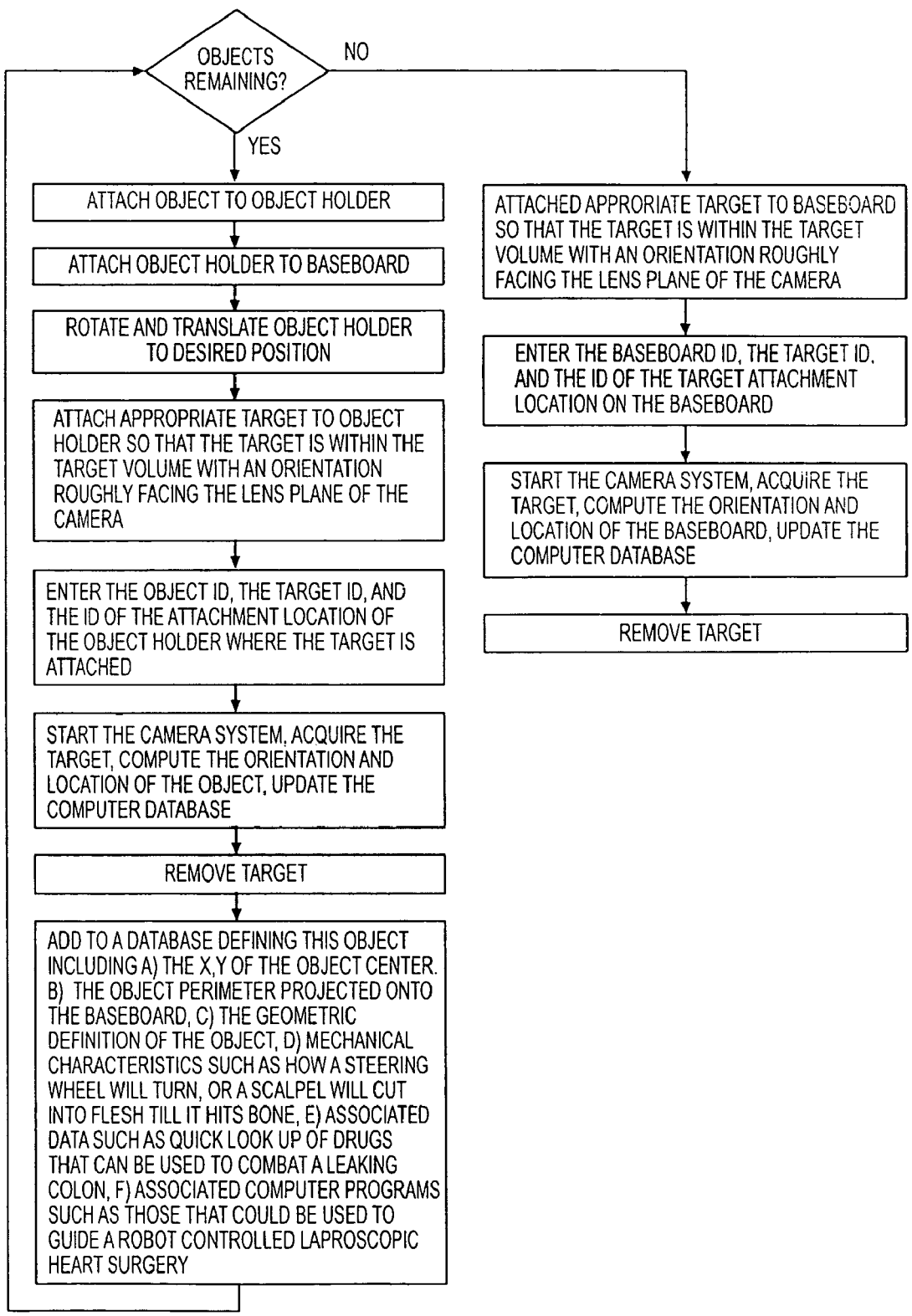
FIG. 8d illustrates a body model on a flexible support.
Figure 8E:
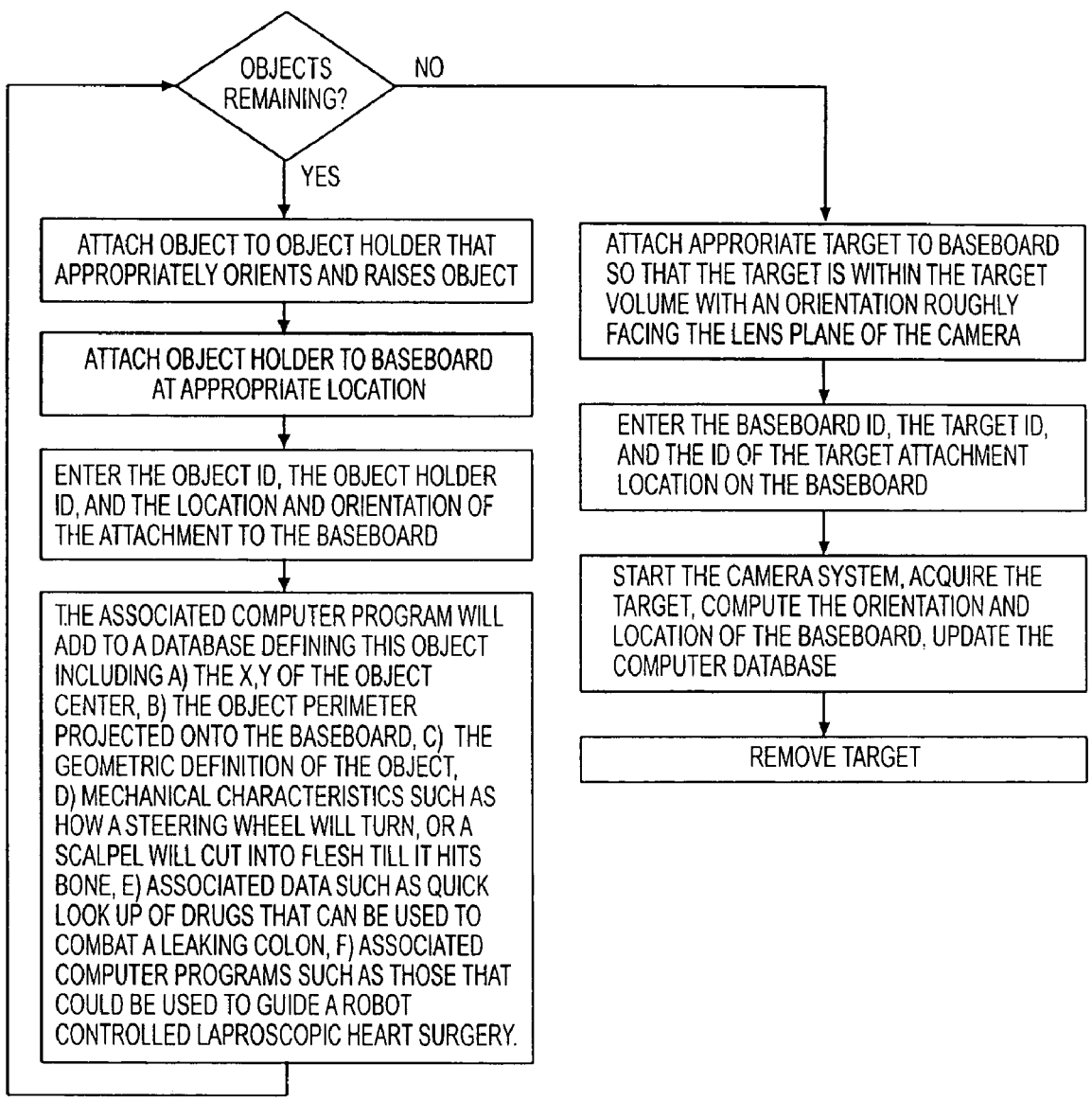
FIG. 8e illustrates a dentist doing real work with a targeted drill.
Figure 8F:
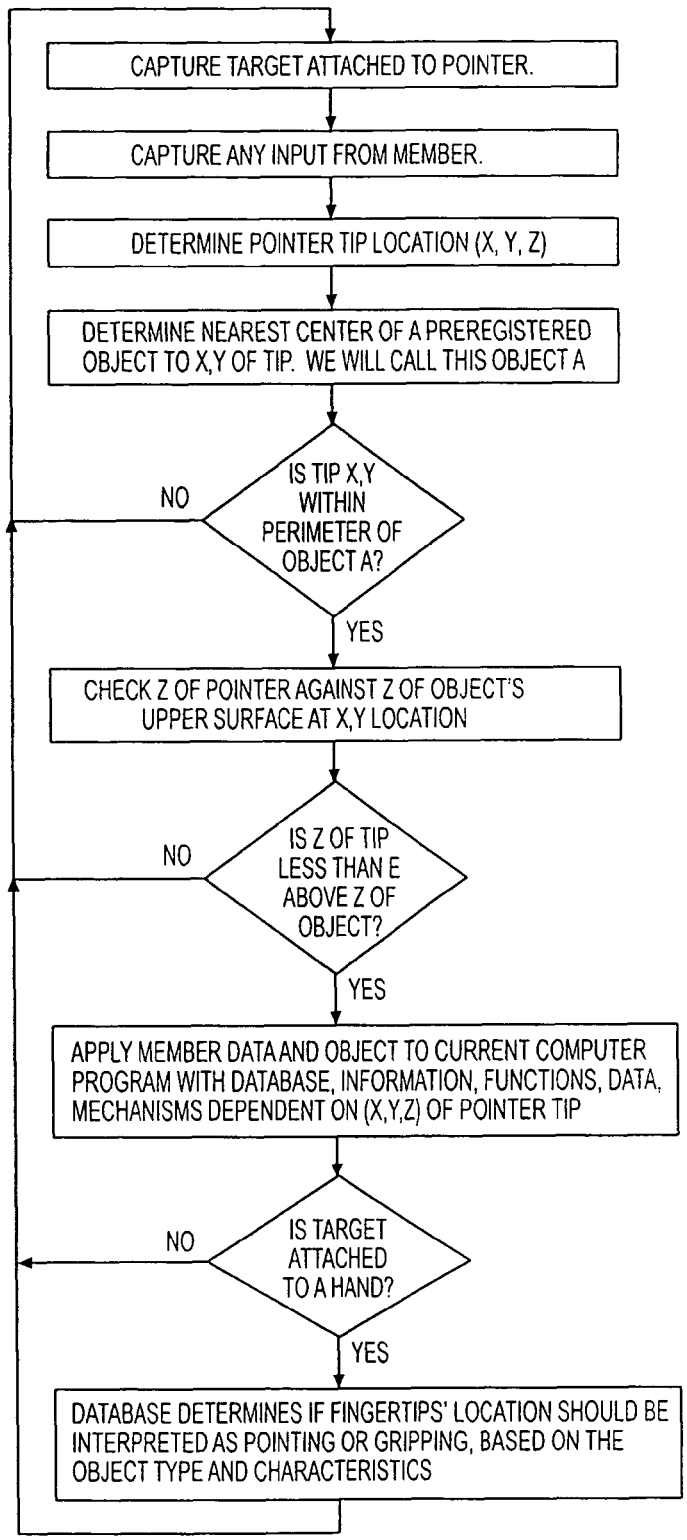
FIG. 8f shows how a surgeon can control the manipulation of a laparoscopic tool or a robot tool through the complex 3D environment of a body with the help of a targeted model of a body as an assembly of body parts.

FIG. 8*c* illustrates a dentist with a targeted drill and a target attached to a patients teeth can have the computer linked to the camera system perform an emergency pull back of the drill if a patient sneezes.

Many other medically related uses may be made of the invention. For example, movement or position of person a person may be sensed, and used to activate music or 3D stimulus. This has suspected therapeutic value when combined with music therapy in the treatment of stroke victims and psychiatric disorders.

Similarly, the output of the sensed condition such as hand or feet position, can be used to control actuators linked to therapeutic computer programs, or simply for use in health club exercise machines. Aids to the disabled are also possible.

FIG. 9

FIG. 9 illustrates a means for aiding the movement of persons hands while using the invention in multiple degree of freedom movement.

Figure 9A:
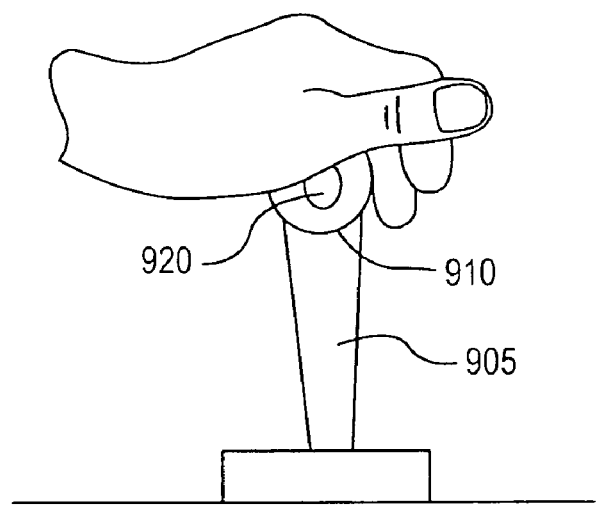
FIG. 9 illustrates a means for aiding the movement of persons hands while using the invention in multiple degree of freedom movement.

A joy stick is often used for game control. Shown in FIG. 9*a* is a joystick 905 of the invention having and end including a ball, 910, in which the data from datums on the ball position at the end of the stick is taken optically by the video camera 915 in up to 6 axes using a square retroreflective target 920 on the ball. The stick of this embodiment itself, unlike other joysticks is provided not as a transduction device, but to support the user. Alternatively some axes can be transduced, e.g. with LVDTS or resolvers, while data in other axes is optically sensed using the invention.

When one wishes to assemble objects, one object may be is held in each hand or one can use two joysticks as above, or one stick aide as shown here, one hand free, for example.

Figure 9B:
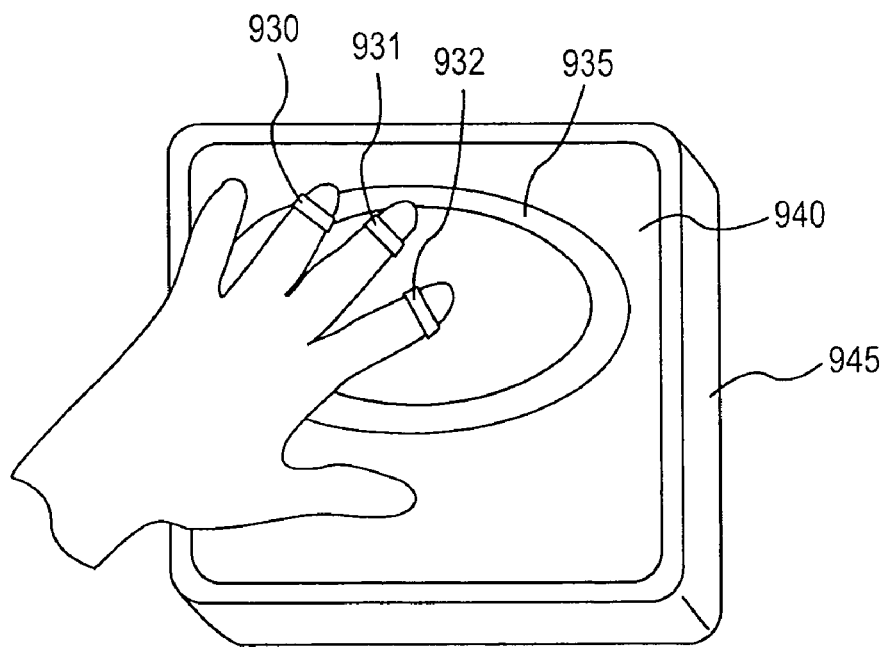

FIG. 9*b* shows an alternate to a joystick, using retroreflective material targets attached to fingers 930,931 and 932 resting on a floating pad 935 resting on a liquid 940 in a container 945. The floating pad gives comfortable support to the hand while freely allowing the targeted hand to move and rotate. We believe that this invention will help reduce the incidence of Carpal Tunnel syndrome.

Figure 9C:
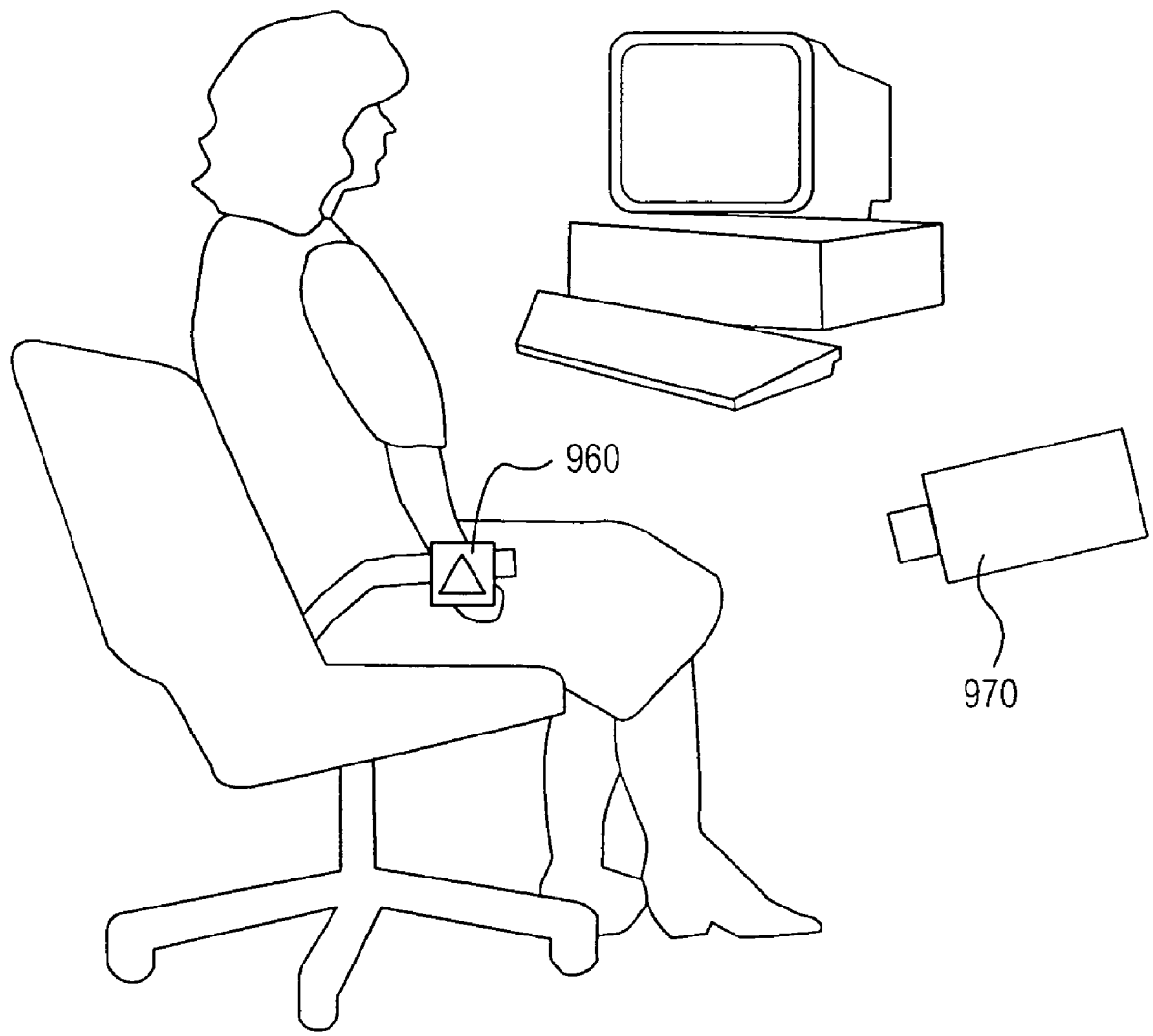

FIG. 9*c* shows another more natural way to use this invention in a way that would eliminate Carpal Tunnel syndrome.

Figure 10:
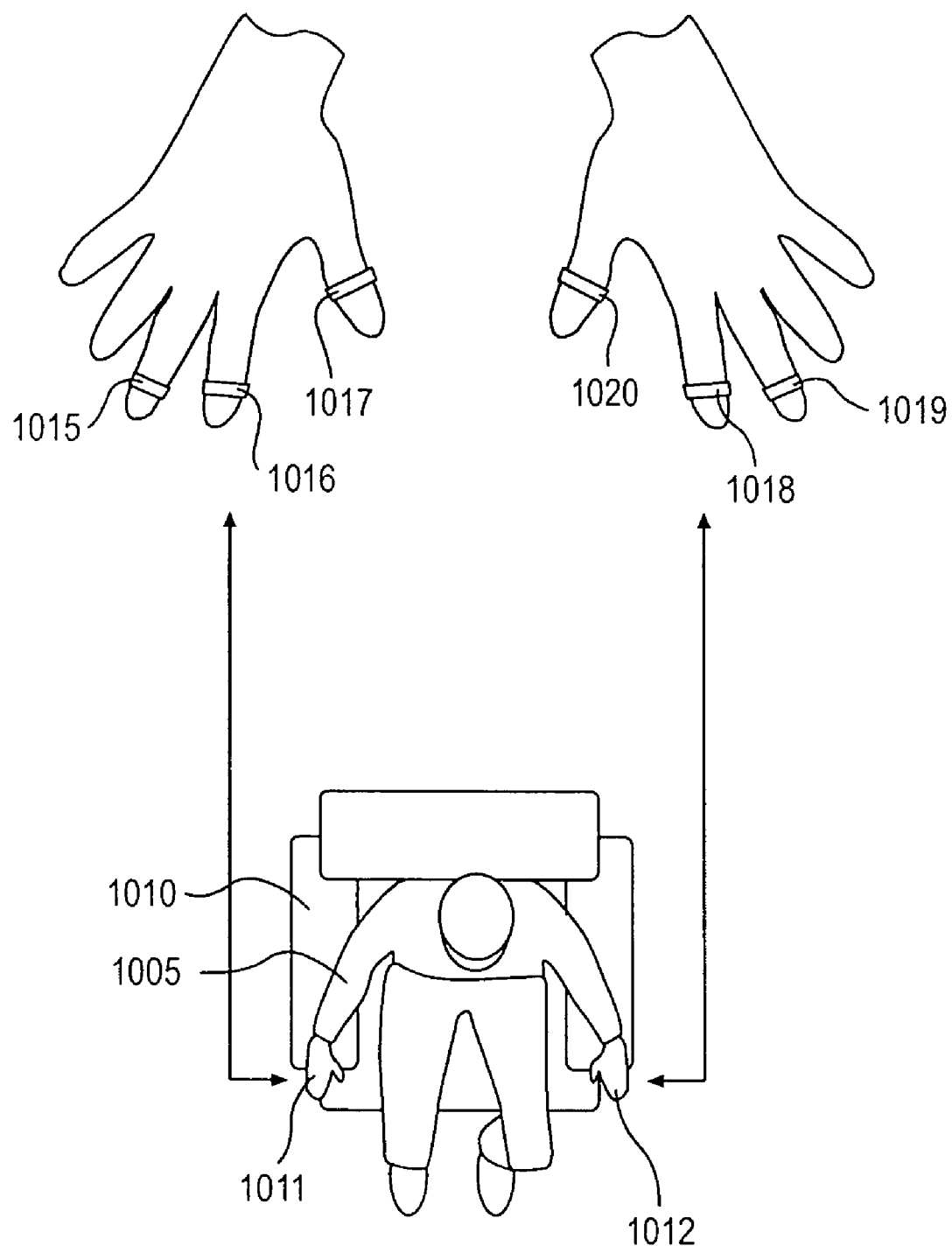
Figure 11:
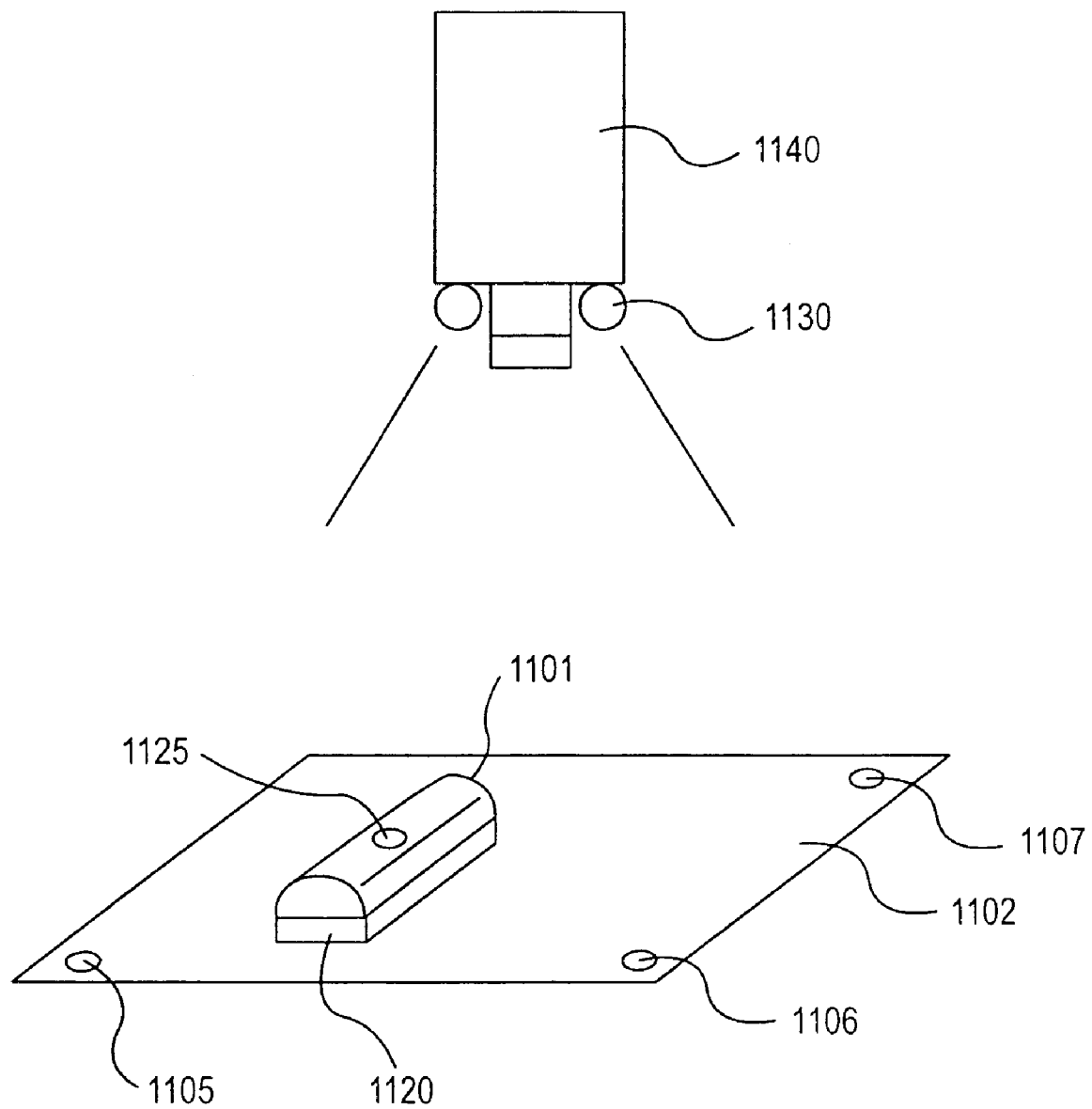
FIG. 11 illustrates coexisting optical sensors for other variable functions in addition to image data of scene or targets. A particular illustration of a Level vial in a camera field of view illustrates as well the establishment of a coordinate system reference for the overall 3-6 degree of freedom coordinate system of the camera(s).

One merely lets the targeted hand 960 hang down in front of a camera system 970, also illustrated in the context of an armrest in FIG. 10.

FIG. 10

FIG. 10 illustrates a natural manner of computer interaction for aiding the movement of persons hands while using the invention in multiple degree of freedom movement with ones arms resting on a armrest of a chair, car, or the like.

As shown, user 1005 sitting in chair 1010 has his thumb and two fingers on both hands 1011 and 1012 targeted with ring shaped retroreflector bands 1015-1020 as shown. All of the datums are seen with stereo TV camera pair 1030 and 1031 on top of display 1035 driven by computer 1040 which also processes the TV camera images. Alternatively, one hand can hold an object, and the user can switch objects as desired, in one or both of his hands, to suit the use desired, as has been pointed out elsewhere in this application.

We have found that this position is useful for ease of working with computers. In particular when combined with microphone 1050 to provide voice inputs as well which can be used for word processing and general command augmentation.

This type of seated position is highly useful for inputs to computers associated with
CAD stations
Cars
Games
Business applications
to name a few. Its noted that the armrest itself may contain other transducers to further be used in conjunction with the invention, such as force sensors and the like.

FIG. 11

This figure illustrates an embodiment wherein other variable functions in addition to image data of scene or targets are utilized. As disclosed, such added variables can be via separate transducers interfaced to the computer or desirably provided by the invention in a manner to coexist with the existing TV camera pickups used for position and orientation input.

A particular illustration of a level vial in a camera field of view illustrates as well the establishment of a coordinate system reference for the overall 3-6 degree of freedom coordinate system of camera(s). As shown level vial 1101 located on the object 1102 is imaged by single camera 1140 along with the object, in this case having a set of 3 retro-reflective targets 1105-1107, and a retro-reflector 1120 behind the level vial to aid in return in light from near co-axial light source 1130 therefrom (and particularly the meniscus 1125) to camera 1140, used both for single camera photogrammetry to determine object position and orientation, but as well to determine the level in one or two planes of the object with respect to earth.

It is noted that the level measuring device such as a vial, inclinometer, or other device can also be attached to the camera and with suitable close-up optics incorporated therewith to allow it to be viewed in addition to the scene. In this case the camera pointing direction is known with respect to earth or whatever is used to zero the level information which can be very desirable.

Clearly other variables such as identification, pressure, load, temperature, etc. can also be so acquired by the cameras of the invention along with the image data relating to the scene or position of objects. For example the camera can see a target on a bimorph responsive to temperature, or it could see the natural image of mercury in a manometer.

FIG. 12

This figure illustrates a touch screen constructed according to the invention employing target inputs from fingers or other objects in contact with the screen, either of the conventional CRT variety, or an LCD screen, or a projection screen—or virtual contact of an aerial projection in space.

As shown, a user 1201 with targeted finger 1203, whose position in 3D space relative to TV screen 1205 (or alternatively absolute position in room space) is observed by camera system 1210 comprising a stereo pair of cameras (and if required light sources) as shown above. When the user places the target 1202 on his finger 1203 in the field of view of the cameras, the finger target is sensed, and as range detected by the system decreases indicating a touch is likely, the sensor system begins reading continuously (alternatively, it could read all the time, but this uses more computer time when not in use). When the sensed finger point reaches a position, such as "P" on the screen, or in a plane or other surface spaced ahead a distance Z from the screen defined as the trigger plane, the system reads the x-y location, in the x-y plane of the screen, for example.

Alternatively a transformation can be done to create artificial planes, curved surfaces or the like used for such triggering as well.

Target datum's on the screen, either retro-reflectors or LED's say at the extremities, or projected on to the screen by electron guns or other light projection devices of the TV system can be used to indicate to, or calibrate the stereo camera system of the invention to the datum points of interest on the screen.

For example calibration datum's 1221-1224 are shown projected on the screen either in a calibration mode or continuously for use by the stereo camera system which can for example search for their particular color and/or shape. These could be projected for a very short time (e.g. one 60 hz TV field), and synched to the camera, such that the update in calibration of the camera to the screen might seem invisible to the user.

A specially targeted or natural finger can be used with the invention, or an object both natural (e.g. a pencil point) or targeted (a pencil with a retroreflector near its tip, for example,) can be used. In general, the natural case is not as able to specifically define a point however, due to machine vision problems in defining its position using limited numbers of pixels often available in low cost cameras. The retroreflector or LED target example is also much faster, due to light power available to the camera system, and the simplicity of solution of its centroid for example.

This is an important embodiment, as it allows one to draw, finger painting, or otherwise write on screens of any type, including large screen projection TV's—especially rear projection, where the drawing doesn't obscure the video projection.

Even when front projection onto a screen is used, one can still draw, using for example a video blanking to only project the screen image where not obscured if desired. The cameras incidentally for viewing the targeted finger or paintbrush, or whatever is used to make the indication can be located even behind the screen, viewing through the screen at the target (this assumes the screen is sufficiently transparent and non-distorting to allow this to occur).

It is noted that the screen may itself provide tactile feel. For example, one can remove material from a screen on which imagery is projected. This could for example be a clay screen, with a front projection source. The object removing the material could be a targeted finger or other object such as a sculpture tool. As discussed previously, the actual removal of material could be only simulated, given a deformable screen feel, or with no feel at all, if the screen were rigid.

It is also of interest that the object on which the projection is displayed, need not be flat like a screen, but could be curved to better represent o conform to the object shape represented or for other purposes.

The embodiment of the invention of FIG. 12 can be further used for computer aided design particularly with large screens which can give life size images, and for use with life size tools and finger motion. The use of inputs herein described, as with respect to the figure above, is expected to revolutionize computer aided design and related fields in the sense of making computer use far more intuitive and able to be used effectively by populace as a whole.

It is extremely interesting to consider a CAD display in life size or at least large size form. In this case, the user experience is much improved over that today and is quicker to the desired result due to the much more realistic experience. Illustrated this are applications to cars and clothes design.

For example, consider the view from the bottom of an underbody of a car with all its equipment such as cables pipes and other components on a life size projection TV image 1260, obtainable today at high definition with digital video projectors, especially if one only worked with half the length of the car at once. Using the invention, a designer 1200 can walk up to the screen image (2 dimensionally displayed, or if desired in stereoscopic 3D), and trace, with his finger 1203, the path where the complex contoured exhaust pipe should go, a notorious problem to design.

The computer 1240 taking the data from stereo pair of TV cameras 1210, can cause the TV screen to display the car undercarriage life size, or if desired to some other scale. The designer can look for interferences and other problems as if it were real, and can even take a real physical part if desired, such as a pipe or a muffler, and lay it life size against the screen where it might go, and move the other components around "physically" with his hand, using his hand or finger tracked by the TV camera or cameras of the system as input to the corresponding modification to the computer generated image projected.

Multiple screens having different images can be displayed as well by the projector, with the other screens for example showing section cuts of different sections of the vehicle which can further indicate to the designer the situation, viewed from different directions, or at different magnifications, for example. With the same finger, or his other hand the designer can literally "cut" the section himself, with the computer following suit with the projected drawing image, changing the view accordingly.

The invention has the ability to focus ones thoughts to a set of motions—fast, intuitive and able to quickly and physically relate to the object at hand. It is felt by the inventors that this will materially increase productivity of computer use, and dramatically increase the ability of the computer to be used by the very young and old.

As noted above in the car design example, individual engineers using targeted hands and fingers (or natural features such as finger tips) or by use of targeted aides or tools as described, they can move literally the exhaust pipe by grabbing it using the invention on the screen and bending it, i.e. causing a suitable computer software program in real time to modify the exhaust pipe data base to the new positions and display same on the projected display (likely wall size).

If no database existed, a drawing tool can be grabbed, and the engineer can "draw" using his targeted and sensed by the TV camera or other sensor of the invention finger or tool on the screen where he wants the exhaust pipe to go. The computer then creates a logical routing and the necessary dimensions of the pipe, using manufacturing data as need be to insure it could be reliably made in economically manner (if not, an indication could be provided to the engineer, with hints as to what is needed).

One of the very beauties of this is that it is near real, and it is something that a group of more than one person can interact with. This gives a whole new meaning to design functions that have historically been solo in front of a "tube".

For best function the screen should be a high definition TV (HDTV) such that a user looking on side sees good detail and can walk over to another side and also see good detail.

Figure 13:
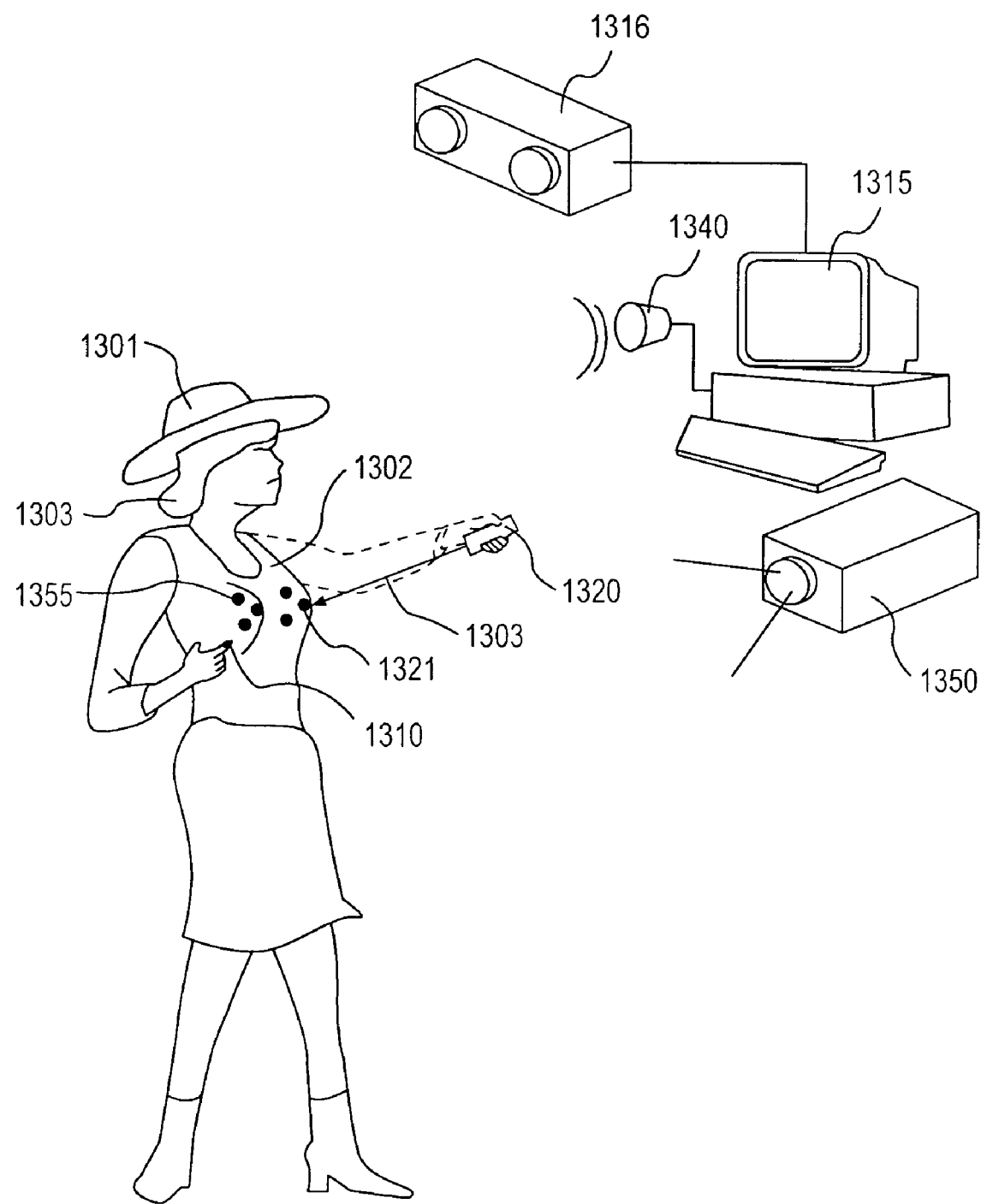
FIG. 13 illustrates clothes design using preferred embodiments incorporating finger touch, laser pointing and targeted material.

Following FIG. 13, another useful big screen design application in full size is to design a dress on a model. The use of the big screen, allows multiple people to interact easily with the task, and allows a person to grip portion of the prototype dress on the screen, and move it elsewhere (in this case finger tips as targets would be useful). It also allows normal dress tools to be used such as targeted knife or scissors.

FIG. 13

Illustrated is clothing design using finger touch and targeted material. The invention is useful in this application both as a multi-degree of freedom input aide to CAD as disclosed elsewhere herein, and for the very real requirement to establish the parameters of a particular subject (a customer, or representative "average" customer, typically) or to finalize a particular style prototype.

A particular example is herein shown with respect to design of women's dresses, lingerie and the like, where the fit around the breasts is particularly difficult to achieve. As shown, the invention can be employed in several ways.

First, the object, in this case a human or manikin, with or without clothes, can be digitized, for the purpose of planning initial cutting or sewing of the material. This is accomplished using the invention using a simple laser pointer. It is believed that some similar ideas have been developed elsewhere, using projection grids, light stripes or the like. However, the digitization of the object can be accomplished at very low cost as described below using the multicamera stereo vision embodiment of the invention.

Secondly, the cloth itself can be targeted, and the multicamera stereo acquired target data before tryout and/or the distorted data (such as position, location or shape) after tryout determined, and modifications made, using this data to assist in modifying the instant material or subsequent material desired.

Third, one can use the ability of the invention to contour and designate action on objects in real time to advantage. For example, consider fashion model 1301 wearing dress 1302 that let us say doesn't fit quite right in the breast area 1303. To help fix this problem, she (or someone else, alternatively) can, using her targeted finger 1310, rub her finger on the material where she wishes to instruct the computer 1315, connected to stereo camera 1316 (including light sources as required), either of her own shape (which could also have been done without clothes on) relative to the shape of the material on her, or, the shape—or lack of shape—she thinks it should be (the lack of shape, illustrated for example to be solved by eliminating a fold, or crease, or bunching up of the dress material). Data from multiple sequential points can be taken as she rubs her finger over herself, obtaining her finger coordinates via the invention and digitizing the shape in the area in question along the path traveled.

Such instruction to the computer can for example be by voice recording (for later analysis, for example) or even instant automatic voice recognition. In addition, or alternatively, it can be via some movement such as a hand movement indication she makes which can carry pre-stored and user programmable or teachable meaning to the computer (described also in FIG. 7 above and elsewhere herein). For example moving her finger 1310 up and down in the air, may be sensed by the camera and discerned as a signal of letting out material vertically. A horizontal wave, would be to do it horizontally. Alternatively she might hold an object with a target on her other hand, and use it provide a meaning. As further disclosed in FIG. 6, she can make other movements which can be of use as well. By pinching her fingers, which could be targeted for ease of viewing and recognition, she could indicate taking up material (note she can even pinch the material of a prototype dress just as she would in real life).

It is noted that the model could alternatively point a laser pointer such as 1320 with spot 1321 at the point on herself needed, the 3D coordinates of the laser designated being determined by the stereo cameras imaging the laser spot. This too can be with a scanning motion of the laser to obtain multiple points. Other zones than round spots can be projected as well, such as lines formed with a cylinder lens. This allows a sequence of data points to be obtained from a highly curved area without moving the laser, which can cause motion error. Alternatively, she could use a targeted object, such as a scissors or ruler to touch herself with, not just her finger, but this not as physically intuitive as ones own touch.

A microphone 1340 may be used to pick up the models voice instruction for the computer. Since instruction can be made by the actual model trying on the clothes, others need not be present. This saves labor to effect the design or modification input, and perhaps in some cases is less embarrassing. Such devices might then be used in clothing store dressing rooms, to instruct minor modifications to other wise ready to wear clothes desired for purchase.

In many applications, a laser pointer can have other uses as well in conjunction with the invention. In another clothes related example, a designer can point at a portion of a model, or clothes on the model and the system can determine where the point falls in space, or relative to other points on the model or clothes on the model (within the ability of the model to hold still). Additionally, or alternatively, the pointer can also be used to indicate to the computer system what area is in need of work, say by voice, or by the simple act of pointing, with the camera system picking up the pointing indication.

It is also noted that the pointer can project a small grid pattern (crossed lines, dot grid, etc.) or a line or a grille (parallel lines) on the object to allow multiple points in a local area of the object o be digitized by the camera system. Such local data, say in a portion of the breast area, is often all that is needed for the designer. This is illustrated by pointer projector 1350 projecting a dot grid pattern of 5×5 or 25 equally spaced spots 1355 (before distortion in the camera image caused by curvature of the object) on a portion of bra 1360, with the spot images picked up by the stereo cameras over not too curved areas is not too difficult. If the points cannot be machine matched in the two stereo camera images by the computer program, such matching can be done manually from a TV image of the zone. Note that different views can also be taken for example with the model turning slightly which can aid matching of points observed. Or alternatively, added cameras from different directions can be used to acquire points.

Note too the unique ability of the system to record in the computer or on a magnetic or other storage medium for example, a normal grayscale photographic image, as well as the triangulated spot image. This of considerable use, both in storing images of the fashion design (or lack thereof) as well as matching of stereo pairs and understanding of the fitting problem.

FIG. 14

Figure 14:
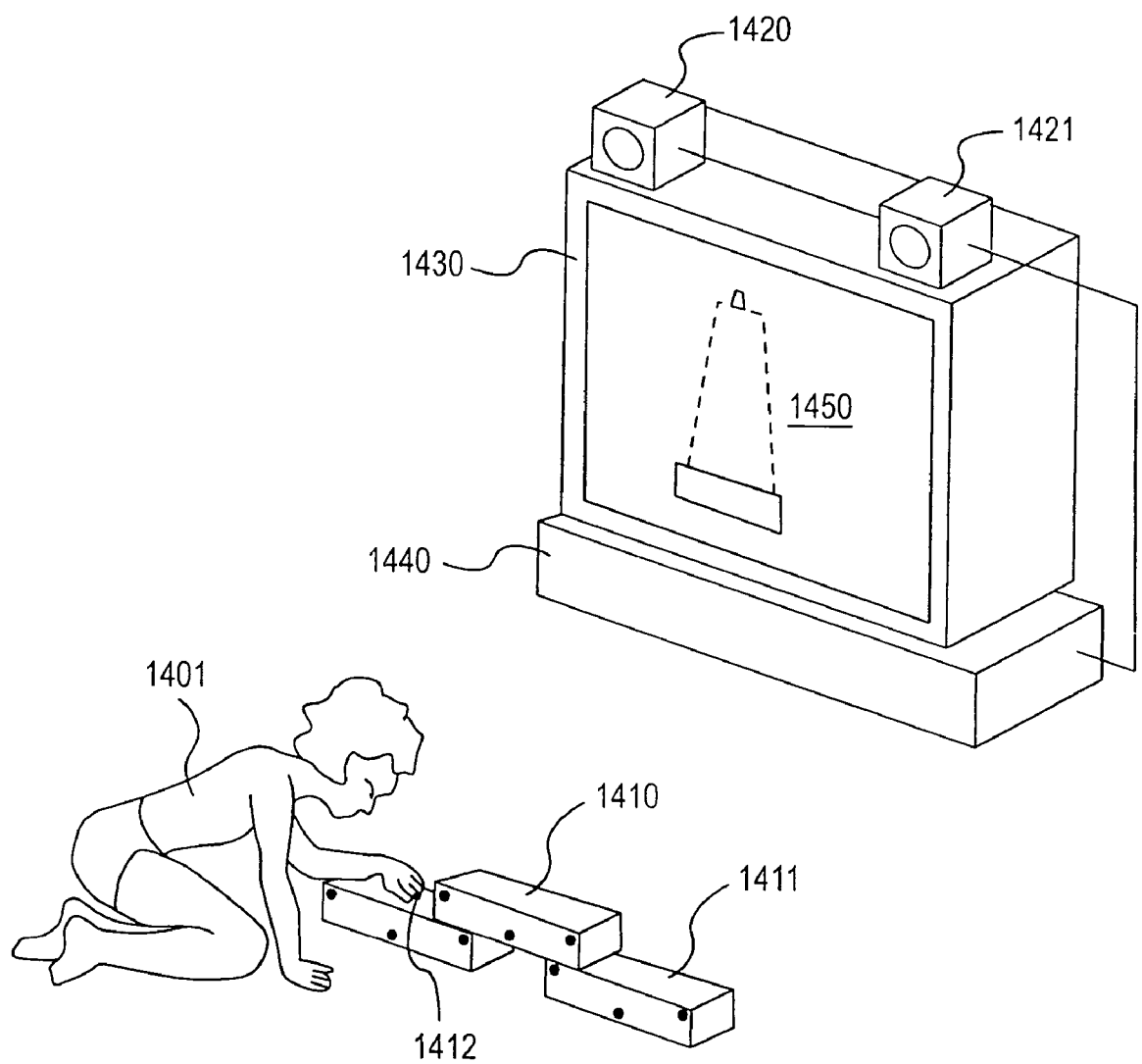
FIG. 14 illustrates additional applications of alias objects such as those of FIG. 3, for purposes of planning visualization, building toys, and inputs in general.

FIG. 14 illustrates additional applications of alias objects such as those of FIG. 3, for purpose of planning visualization, building toys, and inputs in general. As shown, a user, in this case a child, 1401, desires to build a building with his blocks, such as 1410-1412 (only a few of his set illustrated for clarity). He begins to place his blocks in front of camera or cameras of the invention such as cameras 1420 and 1421 which obtain stereo pair of images of points on his blocks which may be easily identified such as corners, dot markings, such as those shown, (which might be on all sides of the blocks) etc, and desirably are retro-reflective or otherwise of high contrast. Rectangular colored targets on rectangular blocks is a pleasing combination.

As he sequentially places his blocks to build his building, images of a building can be made to appear via software running in computer 1440, based on inputs from cameras 1420 and 1421 shown here located on either side of TV screen 1430. These images such as 1450, can be in any state of construction, and can be any building, e.g. the Empire State building, or a computer generated model of a building. Or by changing software concerning the relevant images to be called up or generated, he could be building a ship, a rocket, or whatever.

Similarly, such an arrangement of plurality of objects can be used for other purposes, such as for physical planning models in 3D as opposed to today's computer generated PERT charts, Gant charts, and organization charts in 2D. Each physical object, such as the blocks above, can be coded with its function, which itself can be programmable or selectable by the user. For example, some blocks can be bigger or of different shape or other characteristic in the computer representation, even if in actuality they are the same or only slightly different for ease of use, or cost reasons, say. The target on the block can optically indicate to the computer what kind of block it is.

Another application would be plant layout, where each individual block object could be a different machine, and could even be changed in software as to which machine was which is. In addition, some blocks could for example, in the computer represent machine tools, others robots, and so on.

FIG. 15

FIG. 15 illustrates a sword play video game of the invention using one or more life-size projection screens. While large screens aren't needed to use the invention, the physical nature of the invention's input ability lends itself to same.

As shown, player 1501 holds sword 1502 having 3 targets 1503-1505 whose position in space is imaged by stereo camera photogrammetry system (single or dual camera) 1510, and retro-reflective IR illumination source 1511, so that the position and orientation of the sword can be computed by computer 1520 as discussed above. The display, produced by overhead projector 1525 connected to computer 1520 is a life size or near life size HDTV projection TV image 1500 directly in front of the player 1501 and immersing him in the game, more so than in conventional video games, as the image size is what one would expect in real life.

Let us now consider further how this invention can be used for gaming. In many games it desired both to change the view of the player with aspect to the room or other location to look for aliens or what have you. This is typical of "kick and punch" type games but many other games are possible as well. Regardless, the viewpoint is easily adapted here by tuning the head and targeting the head has been shown and described above, and in copending applications by Tim Pryor.

This however begs an interesting question as to whether in turning the head, one is actually looking away from the game, if the game is on a small screen. This explains why a larger screen is perhaps desirable. But if one sits in front of a large screen, say 40" diagonal or more, one may feel that a little joystick or mouse is much too small as the means to engage computer representations of the opponents. However, using this invention one can simply have a targeted finger or an object in one's hand that could be pointed for example. It is far more natural, especially with larger screens—which themselves give more lifelike representations.

The whole game indeed may actually be on a human scale. With very large projection TV displays, the enemies or other interacting forces depicted on the screen can in fact be human size and can move around by virtue of the computer program control of the projection screen just the same as they would have in life. This however makes it important, and is indeed part of the fun of using the invention, to employ human size weapons that one might use including but not limited to one's own personally owned weapons—targeted according to the invention if desired for ease of determining their location. The opponents actions can be modeled in the computer to respond to those of the player detected with the invention.

A two or more player game can also be created where each player is represented by a computer modeled image on the screen, and the two screen representations fight or otherwise interact based on data generated concerning each players positions or objects positions controlled or maneuvered by the players the same stereo camera system can if desired, be used to see both players if in the same room.

For example in the same, or alternatively in another game, the player 1549 may use a toy pistol 1550 which is also viewed by Stereo camera system, 1510 in a similar manner to effect a "shootout at the OK corral" game of the invention. In this case the players hand 1575 or holster 1520 and pistol 1585 may be targeted with one or more targets as described in other embodiments and viewed by stereo camera (single or dual) system of the invention, as in the sword game above. On the screen in front of the player is a video display of the OK corral, (and/or other imagery related to the game) with "bad guys" such as represented by computer graphics generated image 1535, who may be caused by the computer game software to come in to view or leave the scene, or whatever.

To play the game in one embodiment, the player draws his gun when a bad guy draws his and shoots. His pointing (i.e. shooting)accuracy and timing may be monitored by the target-based system of the invention that can determine the time at which his gun was aimed, and where it was aimed(desirably using at least one or more targets or other features of his gun to determine pointing direction). This is compared in the computer 1520 with the time taken by the bad guy drawing, to determine who was the winner—if desired, both in terms of time, and accuracy of aiming of the player.

An added feature is the ability of a TV camera of the invention to take (using one of the cameras used for datum detection, or a separate camera such as 1580, a normal 2D color photograph or TV image 1588 of a player or other person 1586, and via computer software, superpose it on or other wise use it to create via computer techniques, the image of one of the bad (or good) guys in the game! This adds a personal touch to the action.

Transmission of gaming data, thanks to the transmission properties of fiber cable, ISDN, the Internet or whatever, game opponents, objects and such an be in diverse physical places. On their screen they can see you, on your screen you would see them, with the computer then upon any sort of a hit changing their likeness to be injured or whatever.

Figure 15B:
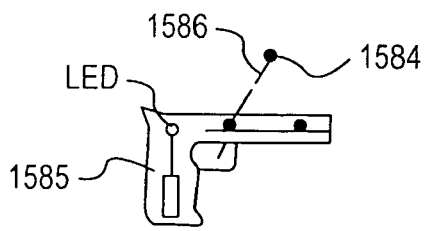

FIG. 15B illustrates on pistol 1585 a target indicator flag 1584 which is activated to signal the TV camera or cameras 1510 observing the pistol orientation and position. When the trigger is pulled, the flag with the target pops up indicating this event. Alternatively, a LED can be energized to light (run by a battery in the toy) instead of the flag raising. Alternatively, a noise such as a "pop" can be made by the gun, which noise is picked up by a microphone 1521 whose signal is processed using taught sounds and/or signature processing methods known in the art to recognize the sound and used to signal the computer 1520 to cause the projected TV image 1500 to depict desired action imagery.

In one embodiment of the Shooting Game, just described, a bad guy, or enemy depicted on the screen can shoot back at the player, and if so, the player needs to duck the bullet. If the player doesn't duck (as sensed by the TV camera computer input device of the invention,) then he is considered hit. The ducking reflex of the player to the gun being visibly and audibly fired on the screen is monitored by the camera that can look at datums on, or the natural features of, the player, in the latter case for example, the center of mass of the head or the whole upper torso moving from side to side to duck the bullet or downward. Alternatively, the computer TV camera combination can simply look at the position, or changes in the position of the target datum's on the player. The center of mass in one embodiment can be determined by simply determining the centroid of pixels representing the head in the gray level TV image of the player.

Its noted that both the sword and the pistol are typically pointed at the screen, and since both objects are extensive in the direction of pointing, the logical camera location is preferably to the side or overhead—rather than on top or side of the screen, say. In addition, line targets aligned with the object axis, such as 1586 on pistol 1585 are useful for accurately determining with a stereo camera pair the pointing direction of the object.

Where required, features or other data of the sword and pistol described, or the user, or other objects used in the game, may be viewed with different cameras 1590 and 1591 (also processed by computer 1520) in order that at any instant in the game, sufficient data on the sword (or pistol, or whatever) position and/or orientation can be determined regardless of any obscuration of the targets or other effects which would render targets invisible in a particular camera view. Preferably, the computer program controlling the sensors of the game or other activity, chooses the best views, using the targets available.

In this case illustrated, it is assumed that target location with respect to the data base of the sword is known, such that a single camera photogrammetry solution as illustrated in FIG. 1b can be used if desired. Each camera acquires at least 3 point targets( or other targets such as triangles allowing a 3D solution) in its field, and solves for the position and orientation using those three, combined with the object data base. In one control scheme, Camera 1590 is chosen as the master, and only if it cant get an answer is camera 1591 data utilized. If neither can see at least 3 targets, then data from each camera as to target locations is combined to jointly determine the solution (e.g. 2 targets from each camera).

The primary mode of operation of the system could alternatively be to combine data from two cameras at all times. Often the location of choice is to the side or overhead, since most games are played more or less facing the screen with objects that extend in the direction to the screen (and often as result are pointed at the screen). For many sports however, camera location looking outward from the screen is desired due to the fact that datums maybe on the person or an object. In some cases cameras may be required in all 3 locations to assure an adequate feed of position or orientation data to computer 1520.

The invention benefits from having more than 3 targets on an object in a field, to provide a degree of redundancy. In this case, the targets should desirably be individually identifiable either due to their color, shape or other characteristic, or because of their location with respect to easily identifiable features of the sword object.

Alternatively, one can use single targets of known shape and size such as triangles which allow one to use all the pixel points along an edge to calculate the line—thus providing redundancy if some of the line is obscured.

Note that one can use the simple tracking capability of the invention to obtain the coordinates of a target on a user in a room with respect to the audio system and, if desired also with respect to other room objects influencing sound reverberation and attenuation. This coordinate can then be used by a control computer not shown for the purpose of controlling a audio system to direct sound from speakers to the user. Control of phase and amplitude of emission of sound energy. While a single target on a hat can be simply detected ad determined in its 3D location by the two or more camera stereo imaging and analysis system of the invention, natural features of the use could alternatively, or in addition be used, such as determining from the gray level image detected by the TV camera of FIG. 1 say, the users head location. As pointed out elsewhere, the target can be on the body, and the head can be found knowing the target location—to simplify identification of the head in an overall image of a complex room scene, say.

Besides control of audio sound projection, such coordinate data can also be used to control the screen display, to allow stored images to be directed in such a way as to best suit a use in a given part of a room, for example using directional 3D projection techniques. If user head angle as well is determined, then the viewpoint of the display can be further controlled therefrom.

Data Transmission

Programs used with the invention can be downloaded from a variety of sources. For example:

Disc or other storage media packed with a object such as a toy, preferably one with easily discernable target features, sold for use by the invention.

From remote sources, say over the internet, for example the web site of a sponsor of a certain activity. For example daily downloads of new car driving games could come from a car company's web site.

A partner in an activity, typically connected by phone modem or internet, could not only exchange game software for example, but the requisite drivers to allow ones local game to be commanded by data from the partners activity over the communication link.

One of the interesting aspects of the invention is to obtain instructions for the computer controlling the game (or other activity being engaged in) using the input of the invention, from remote sources such as over the Internet. For example, let us say that General Motors wanted to sponsor the car game of the day played with a toy car that one might purchase at the local Toys-R-Us store and with its basic dashboard and steering wheel brake panel accelerator, gear lever, etc. All devices that can easily be targeted inputted via the video camera of the invention of FIG. 4.

Today such a game would be simply purchased perhaps along with the dashboard kit and the first initial software on DVD or CD ROM. In fact those mediums could typically hold perhaps ten games and DVD of different types.

For example, in the GM case, one day it could be a Buick and the next day a Corvette and so on with the TV view part of this screen changing accordingly.

Remote transmission methods of the Internet, ISDN, fiber links dedicated or shared or otherwise are all possible and very appealing using the invention. This is true in many things, but in this case particularly since the actual data gathered could be reduced to small amounts of transmitted data.

The stereo photogrammetric activity at the point of actual determination can be used directly to feed data to the communications media. Orientation and position of objects or multiple points on objects or the like can be transmitted with very little bandwidth, much less difficult than having to transmit the complete image. In fact, one can transmit the image using the same cameras and hen use the computer at the other end to change the image in response to the data transferred, at least over some degree of change. This is particularly true if one transmits a prior set of images that corresponds to different positions. These images can be used at any time in the future to play the game by simply calling them up form the transmitted datum's.

Similar to the playing function of FIGS. 5, 15 etc, there is also a teaching function, as was discussed relative to medical simulations in FIG. 8. The invention is for example, also useful in the teaching of ballet, karate, dance and the like. The positions and orientation of portions of the ballerina or her clothes can be determined busing the invention, and compared to computer modeled activity of famous ballerinas for example. Or in a more simple case, a motion of the student, can be used to call TV images from memory bank which were taken of famous ballerinas doing the same move—r of her instructor. And, given the remote transmission capability, her instructor may be in another country. This allows at least reconstructed motion at the other end using a very small amount of transmitted data, much the same as we would reconstruct the motion of a player in the game.

While this doesn't answer the question of how the instructor in the ballet studio actually holds the student on occasion but it does help the student to get some of the movement correct. It also allows one to overlay visually or mathematically, the movements of the student generated, which have now been digitized in three dimensions, on the digitized three dimensional representation of famous ballerinas making the same basic moves, such as pas-de-chat. This allows a degree of self-teach capability, since clearly one might wish to look at the moves of perhaps three or four noted ballerinas and compare.

The invention thus can use to advantage 3D motion done at very low cost in the home or in a small time ballet studio but nonetheless linked through CD ROM, the Internet or other media to the world's greatest teachers or performers. What holds true for ballet generally would also hold true for any of the sports, artistic or otherwise that are taught in such a manner. These can particularly include figure skating, golf or other sports that have to do with the moves of the person themselves.

One can use the invention to go beyond that, to the moves of the person themselves relative to other persons. This is particularly discussed in the aforementioned co-pending application relative to soccer and hockey, particularly relative to hose sports that have goaltenders against whom one is trying to score a goal. Or conversely, if you're the goaltender, learning defense moves against other teams that are trying to score on you. In each one could have a world famous goalie instructing, just as in the ballet above, or one could have world famous forwards acting against you.

This is a very exciting thing in that you get to play the "best", using the invention. These can even be using excerpts from famous games like the Stanley Cup, World Cup and so on. Like the other examples above, the use of 3D stereo displays for games, for sports, for ballet or other instruction, is very useful, even if it requires wearing well known stereo visualization aids such as TV frame controlled LCD based or polarized glasses. However a lot of these displays are dramatic even in two dimensions on a large screen.

Let us now consider how the game would work with two players in the same room with play either would be with respect to themselves or with respect to others.

Where there are cases of coordinated movements for the same purpose as in figure skating, ballet and the like, most of such games are one person relative to the other, sensing sword play, pistol duels, karate, and so on. In what mode does this particularly connect with the invention?

In FIG. 5 above we've illustrated the idea of two children playing an airplane game. In this case, they are playing with respect to themselves. But not necessarily directly, but rather indirectly by viewing the results of their actions on the screen, and it is on the screen that the actual event of their interaction takes place. In addition it should be noted that a single player can hold an airplane in each hand and stage the dogfight himself.

In the case shown it was an airplane dogfight, one with respect to the other. Although as discussed, one can using the invention, by simply changing ones command cues, by movements, gestures or another mode desired, change it from an airplane to a ship, or even change it from airplanes to lions and tigers. It is determined in the software and the support structure around the software.

The actual movements of the person or objects are still determined and still come into play. There are differences though of course because in the case of lions and tigers, one might wish to definitely target the mouth so that you could open your jaws and eat the other person or whatever one does.

The targeting of a beak outline was illustrated in the Big Bird Internet puppet example of FIG. 5. Curvilinear or Line targets are particularly useful for some of these as opposed to point targets. Such targets are readily available using retro-reflective beading as is commonly found today on some athletic shoes, shirts, or jackets, for the purpose reflecting at night.

The use of co-located two players, one versus the other, but through the medium of the screen, is somewhat different. But if the screen is large enough it gives the ability to be real. In other words, the player on the screen is so large and so proportional, that it takes over the fact that the player in the room with you is not a real one(s), but rather his representation on the screen. Any sort of game can be done this way where the sensed instruments are pistols, swords and the like.

In many cases the object locations and orientations sensed are simply the objects relative to the camera system. But often times, what is desired is the relative position of either the people or the object as has been discussed in referenced US Patent applications by Tim Pryor.

Now described is a teaching embodiment of the invention also for use remotely over the Internet or otherwise in which ballet instruction is given, or architecture is taught or accomplished. The teaching session can be stored locally or transmitted over a computer link such as the Internet. Karate or dance for example can be taught over the Internet. Targets if required, can be attached to arms, hands, legs, or other parts of the body. The user's body part paths can be tracked in space in time by one or more camera systems. The video can be analyzed in real-time or can be recorded and later analyzed.

The TV image data can ultimately even be converted to "Quant" data representing sequences of motion detected by the camera system for compact data transmission and storage. In this case, the specific path data could be recognized as a specific karate thrust, say. This motion together with its beginning and end locations and orientation may be adequate for an automatic system. On the other hand, a two-way Internet connection would allow the instructors move to be compared with that of the student. By reducing the data to Quant data the instructors and students size differences could be factored out.

The invention can be used to determine position and orientation of everyday objects for training and other purposes. Consider that position and orientation of a knife and fork in ones hands can be detected and displayed or recorded, if target datum's are visible to the camera system, either natural (e.g. a fork tip end) or artificial, such a retro-reflective dot stuck on. This allows one to teach proper use of these tools, and for that matter any tools, such as wrenches, hammers, etc. indeed any apparatus that can be held in the hands (or otherwise). The position too of the apparatus held with respect to the hands or other portions of the body for other bodies maybe determined as well.

This comes into clear focus relative to the teaching of dentists and physicians, especially surgeons. Scalpels, drills, and the like may all be targeted or other wise provided with natural features such as holes, slots, and edges which can work with the invention.

In the military such training aids are of considerable use, and become as well an aid to inspiring young recruits, for whom the TV display and video game aspect can render perhaps a dull task, fun. The proper ergonomic way to dig a foxhole, hold a rifle, could be taught this way, just as one could instruct an autoworker on an assembly line installing a battery in a car.

FIG. 16

Figure 16:
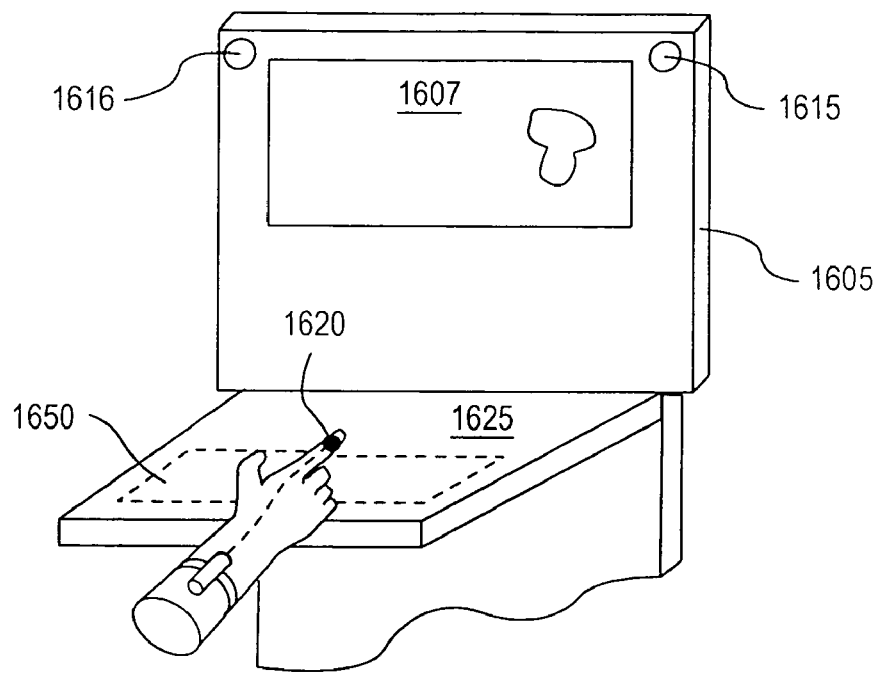
FIG. 16 illustrates an embodiment of the invention having a mouse and/or keyboard of the conventional variety combined with a targets of the invention on the user to give an enhanced capability even to a conventional word processing or spreadsheet, or other program. A unique portable computer for use on airplanes and elsewhere is disclosed.

FIG. 16 illustrates an embodiment of the invention suitable for use on airplanes and other tight quarters. A computer having an LCD screen 1610, which can attached if desired to the back of seat ahead 1605 (or to any other convenient member), has on either side of the screen, near the top, two video cameras 1615 and 1616 of the invention, which view workspace on and above the tray table folding down from the seat ahead. The user communicates with the computer using a microphone (for best reception a headset type not shown, connected to the computer) which converts voice to letters and words using known voice recognition techniques. For movement of words, paragraphs, and portions of documents, including spread sheet cells and the like, the user may use the invention.

In the form shown, he can use a variety of objects as has been discussed above. For simplicity, consider battery powered LED 1620 on his finger, 1625, which emits at a narrow wavelength region which is passed by band pass filters (not shown for clarity )on the front of cameras 1616 and 1615, respectively. Since a full 3 degree of freedom location of the finger LED is possible, movement off the table of the finger (which other wise becomes a sort of mouse pad, or touch pad in 2 Axes) can be used to optionally signal the program to perform other functions. Or if there are 3D graphics to interact with, it can be of great utility for them. Indeed, other fingers, or of the other hand can also contain LED targets which allow many functions described herein to be performed in up to 6 axes.

One can also place a normal keyboard such as 1650 interfaced to the computer (built into the back of the led display for example) on the tray table (or other surface), and use the led equipped finger(s) to type normally. But a wide variety of added functions can again be performed, by signaling the computer with the LED targets picked up by the video cameras. There can be movement gestures to signal certain windows to open for example. Other functions are:

1. Pointing with finger with target and 3 pints on wrist at icon or other detail depicted on screen.
2. Extend values out of chart in $3^{rd}$ dimension by pulling with targeted fingers in the manner described in FIG. 6.
3. Solid icons can be placed on the tray table and detected, in this case each having a small led or leds and battery. These can be moved on the table to connote meaning to the computer, such as the position of spread sheet cells or work blocks in pert chart, and the like.
4. Use cameras to detect position of laser spot on an object on the tray illuminated by a laser pointer held in the hand of the user (preferably the laser wavelength and led wavelength would be similar to allow both to pass the bandpass filters).
5. Its noted the screen could be larger than otherwise used for laptop computers, since it is all out of the way on the back of the seat (or at a regular desk, can stand up with folding legs for example). The whole computer can be built into the back of the device (and is thus not shown here for clarity).
6. A storage space for targeted objects used with the invention can be build into the screen/computer combination or carried in a carrying case. Attachments such as targets for attachment to fingers can also be carried.
7. Its noted that for desk use the invention allows human interaction with much larger screens than would normally be practical. For example if the screen is built into the desktop itself (say tilted at 45% like a drafting board), the user can grab/grip/pinch objects on the screen using the invention, and move them rotate them or other wise modify their shape, location or size for example using natural learned skills. Indeed a file folder can be represented literally as a file folder of normal size, and documents pulled out by grabbing them. This sort of thing works best with high resolution displays capable of the detail required.

FIG. 16 has illustrated an embodiment of the invention having a mouse and/or keyboard of the conventional variety combined with a target of the invention on the user to give an enhanced capability even to a conventional word processing or spreadsheet, or other program.

For example consider someone whose interest is developing a spreadsheet prediction for company profit and loss. Today this is done exclusively using a keyboard to type in data, and a mouse (typically) to direct the computer to different cells, pull down window choices and the like. This job is generally satisfactory, but leads to carpal tunnel syndrome and other health problems and is somewhat slow—requiring typing or mouse movements that can overshoot, stick and the like.

Voice recognition can clearly be used to replace the typing, and gesture sensing according to the invention including specialized gestures or movements such as shown in FIG. 5 can be used to improve recognition of voice inputs by the computer system.

But what else is possible? Clearly one can use the touch screen indicator aspect to point directly at objects on the screen. For example, consider a user such as in FIG. 12 may seated in front of a large high definition display screen on a wall or tilted 45 degrees as at a writing desk. The user can either touch (or near touch) the screen as in FIG. 12 or he can point at the screen with his finger targeted with retro-reflective scotch-lite glass bead target and the pointing direction calculated using the 3 target set on top of his wrist as in FIG.

1b. The screens' datum's are known, for example four retro-reflective plastic reflector points at the corners 1270-1273 as shown. As elsewhere discussed, projected targets on the screen can also be used to establish screen locations—even individually with respect to certain information blocks if desired. A Stereo camera pair senses the positions of wrist and finger, and directs the computer and TV projector (not shown) to follow the wishes of the user at the point in question. The user may use his other hand or head if suitably targeted or having suitable natural features, to indicate commands to the camera computer system as well.

Of interest is that the display can be in 3D using suitable LCD or other glasses to provide the stereo effect. This allows one to pull the values out of the excel chart and make them extendable in another dimension. One can pull them out, so to speak by using for example as shown in FIG. 6, using two targeted fingers (e.g. targeted thumb and targeted finger and grab or pinch and pull the object in the cell. In a word processor the word on the page can be so grabbed.

On can use this effect to work backward form a 3D bar graph created by the spread sheet program i.e. to press on the individual bars until the form of the data shown meets ones goals, by pressing as in a repeated finger motion downward, the program changes the data in certain cell scenarios (e.g. sales, expenses, profits, etc.).

In another example, transparent targeted blocks may be moved over the top of transparent rear projection screen. The blocks can also extend in height above the screen by a variable amount. Data can be inputted by the computer screen, but also by varying the block height. The height is then encoded into the screen projection to change the color or another parameter.

In the factory layout example of FIG. 14 above, if blocks are translucent and placed on a screen, the colors, written description, or pictorial description (e.g. a lathe, or a mill) of screen, with the target data on the block tracked and fed to the TV projection source. Such an arrangement might be useful for other complex tasks, also in real time, as in Air traffic control.

Other target arrangements sufficient to determine pointing direction can also be used. This pointing method can also be used to point at anything not just screens. It is especially useful with voice commands to tell the pointed item to do something. It is also of use to cue the projection system of the TV image to light up the pointed area or otherwise indicate where pointing is taking place.

For giving presentations to a group, the invention can operate in reverse from a normal presentation computer—that is the person standing giving the presentation can point at the screen where the information is displayed, and what he pointed at, grasped, or what ever recorded by the cameras of the invention into the computer.

It is further noted that a laser pointer can be targeted and used for the purpose.

FIG. 17

Figure 17:
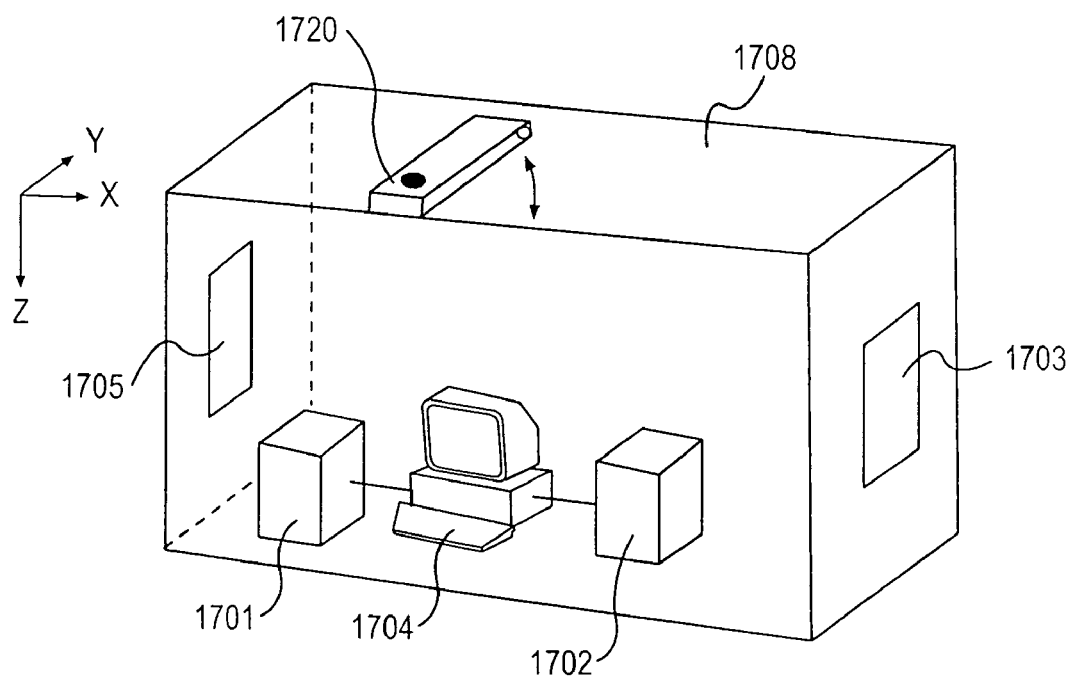
FIG. 17 illustrates a optically sensed keyboard embodiment of the invention, in this case for a piano.

This embodiment illustrates the versatility of the invention, for both computer input, and music. As shown in FIG. 17A, a two camera stereo pair 1701 and 1702 connected to computer 1704 such as mentioned above for use in games, toys and the like can also be used to actually read key locations on keyboards, such as those of a piano or typewriter. As shown, letters or in the piano case, musical note keys such as 1708 with retro target 1720 on their rear, beneath the keyboard, are observed with the camera set 1701. A Z axis movement gives the key hit (and how much, if desired—assuming elastic or other deformation in response to input function by player finger 1710), while the x (and y if a black key, whose target is displaced for example) location of the key tells which letter or note it is. Speakers 1703 and 1705 provide the music from a MIDI computer digital to speaker audio translation.

For highest speed and resolution, useful with long keyboards, and where the objects to be observed are in a row (in this case the keys), the two cameras are in this instance composed of 2048 element Reticon line arrays operating at 10,000 readings per second. Specialized DSP processors to determine the stereo match and coordinates may be required at these speeds, since many keys can be pressed at once.

Alternatively, the piano players finger tips as disclosed in previous embodiments can be imaged from above the keyboard (preferably with retroreflective targets for highest speed and resolution) to create knowledge of his finger positions. This when coupled with knowledge of the keyboard data base allows one to determine what key is being struck due to the z axis motion of the finger.

FIG. 18

Figure 18:
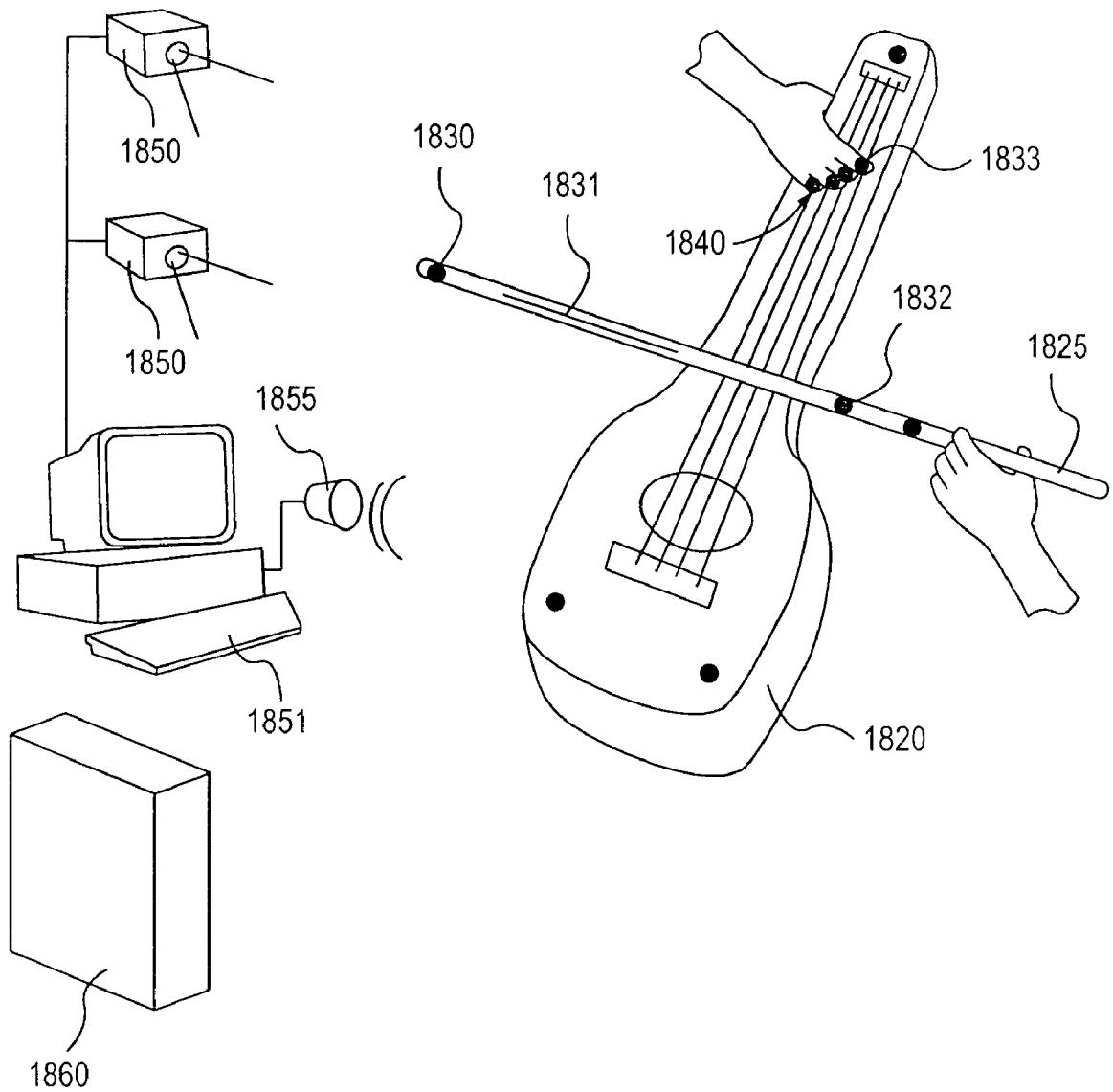
FIG. 18 illustrates gesture based musical instruments such as violins and virtual object musical instruments according to the invention, having synthesized tones and, if desired, display sequences.

Virtual musical instruments are another music creation embodiment of the invention. A dummy violin surrogate such as 1820 in FIG. 18 can be provided which is played on bowstrings real or dummies by a bow 1825 also real or dummies The position of the bow, vis a vis the dummy violin body 1830 proper, and the position of the fingers 1840 (which may be targeted) gives the answer as to what music to synthesize from the computer. It is envisioned that the easiest way to operate is to use retro-reflecting datums such as dot or line targets 1830, 1831, 1832, and 1833, on all of the bow, violin, and fingers, viewed with stereo camera system 1850 connected to computer 1851 and one or more loudspeakers 1855.

Frequency response is generally enough at 30 frames per second typical of standard television cameras to register the information desired, and interpolation can be used if necessary between registered positions (of say the bow). This may not be enough to provide full timber of the instrument however. One can use faster cameras such as the line arrays mentioned above (if usable), PSD cameras as in FIG. 22 and/or techniques below to provide a more desirable output.

The input from the targeted human, or musical instrument part (e.g. key or bow or drumstick) may cause via the computer the output be more than a note, for example a synthesized sequence of notes or chords—in this manner one would play the instrument only in a simulated sense—with the computer synthesized music filling in the blanks so to speak.

Similarly a display such as 1860 may be provided of the player playing the simulated instrument surrogate, may use the data of positions of his hands in a few positions, and interpret between them, or call from memory more elaborate moves either taught or from a library of moves, so that the display looks realistic for the music played (which may be also synthesized) as noted above.

The display fill in is especially easy if a computer model of the player is used, which can be varied with the position data determined with the invention.

FIG. 19

Figure 19:
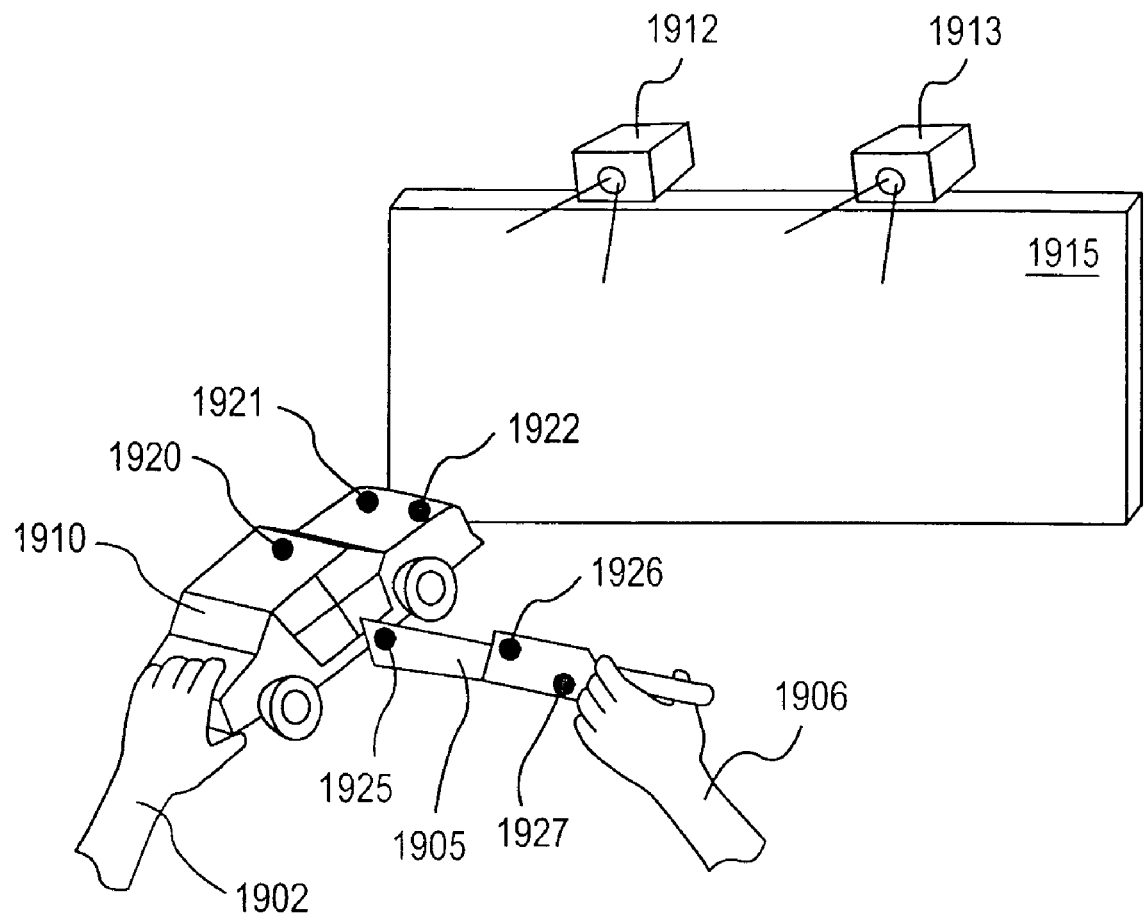
FIG. 19 illustrates a method for entering data into a CAD system used to sculpt a car body surface.
Figure 19:
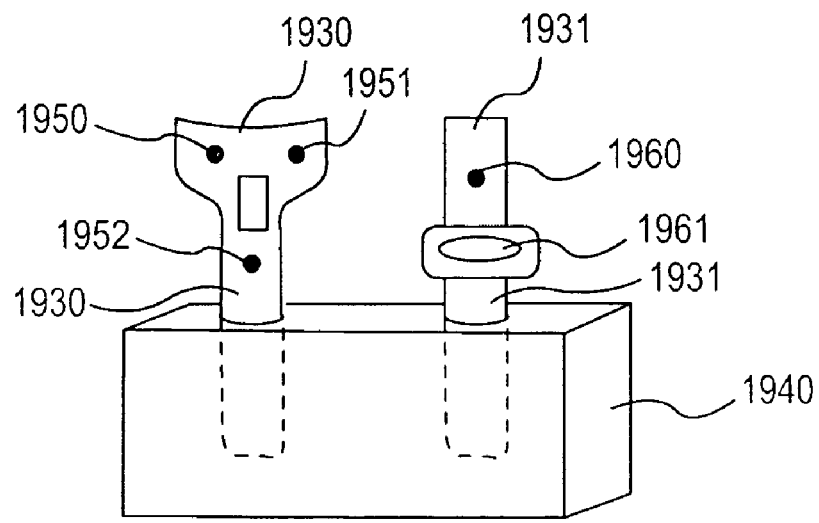

FIG. 19 illustrates a method for entering data into a CAD system used to sculpt a car body surface, in which a physical toy car surrogate for a real car model, 1910, representing for example the car to be designed or sculpted, is held in a designers left hand 1902, and sculpting tool 1905 in his right hand 1906. Both car and tool are sensed in up to 6 degrees of freedom each by the stereo camera system of the invention, represented by 1912 and 1913,(connected to a computer not shown used to process the camera data, enter data into the design program, and drive the display 1915). The objects are equipped with special target datums in this example, such ass 1920-1922 on car 1910, and 1925-1927 on sculpting tool

1905. A display of a car to be designed on the screen is modified by the action of the computer program responding to positions detected by the camera system of the sculpting tool 1905 with respect to the toy car, as the tool is rubbed over the surface of the toy car surrogate.

One can work the virtual model in the computer with tools of different shapes. Illustrated are two tools 1930 and 1931, in holder 1940 of a likely plurality, either of which can be picked up by the designer to use. Each has a distinctive shape by which to work the object, and the shape is known to the design system. The location of the shaped portion is also known with respect to the target datum's on the tools such as 1950-1952. As the tool is moved in space, the shape that it would remove (or alternatively add, if a build up mode is desired) is removed from the car design in the computer. The depth of cut can be adjusted by signaling the computer the amount desired on each pass. The tool can be used in a mode to take nothing off the toy, or if the toy was of clay or coated in some way, it could actually remove material to give an even more lifelike feel.

3 targets are shown, representatively on tool 1930, with three more optionally on the other side for use if the tool becomes rotated with respect to the cameras. Each tool has a code such as 1960 and 1961 that also indicates what tool it is, and allows the computer to call up from memory, the material modification effected by the tool. This code can be in addition to the target datum's, or one or more of the datum's can include the code.

FIG. 20

Figure 20:
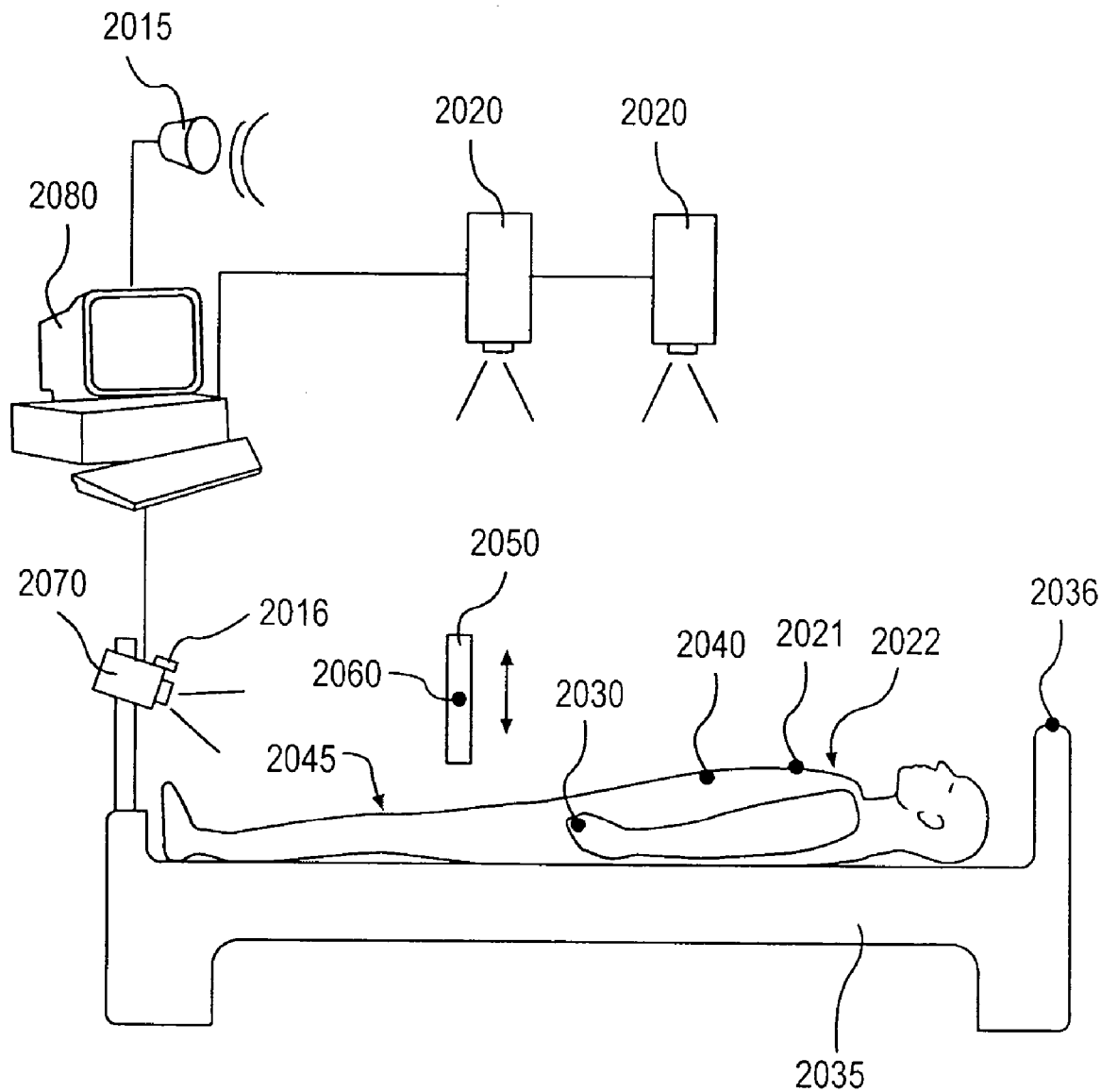
FIG. 20 illustrates an embodiment of the invention used for patient or baby monitoring.

FIG. 20 illustrates an embodiment of the invention used for patient monitoring in the home, or hospital. A group of retro-reflective targets such as 2021, 2030, and 2040 are placed on the body of the person 2045 and are located in space relative to the camera system, (and if desired relative to the bed 2035 which also may include target 2036 to aid its location), and dynamically monitored and tracked by stereo camera system 2020 composed of a pair of VLSI Vision 1000×1000 CMOS detector arrays and suitable lenses.

For example, target 2021 on chest cavity 2022 indicates whether the patient is breathing, as it goes up and down. This can be seen by comparison of target location in sequential images, or even just target blur (in the direction of chest expansion) if the camera is set to integrate over a few seconds of patient activity.

Target 2030 on the arm, as one example of what might be many, is monitored to indicate whether the patient is outside a perimeter desired, such as the bed 2035. If so, computer, 2080 is programmed to sound an alarm 2015 or provide another function, for example alerting a remote caregiver who can come in to assist. Microphone, such as 2016 may also be interfaced to the computer to provide a listening function, and to signal when help his needed.

Also illustrated is an additional target or targets another portions of the chest or body, such as 2040, so that if the patient while asleep or otherwise covers one with his arm, the other can be sensed to determine the same information.

Also disclosed, is like figure above, the conversion of a variable of the patient, in this case blood pressure, into a target position that can be monitored as well. Pressure in manometer 2050 causes a targeted indicator 2060 (monitored by an additional camera 2070 shown mounted to the end of the bed and achieving higher resolution if desired) to rise and fall, which indicates pulse as well.

While described here for patients, the same holds true for babies in cribs, and the prevention of sudden infant death syndrome(SIDS), by monitoring rise and fall of their chest during sleep, and to assure they are not climbing out of the crib or the like.

FIG. 21

Following from the above, a simple embodiment of the invention may be used to monitor and amuse toddlers and preschool age children. For example in the FIG. 1 embodiment a Compaq 166 MHz Pentium computer 8, with Compaq 2D color TV camera 10, was used, together with an Intel frame grabber and processor card to grab and store the images for processing in the Pentium computer. This could see small retro targets on a doll or toddlers hands, with suitable LED lighting near the camera axis. The toddler is seated in a high chair or walking around at a distance for example of several feet from the camera mounted on top of the TV monitor. As the toddler moves his hands, or moves the dolls hands, alternatively ) an object such as a doll image or a the modeled computer graphics image of clown, let us say could move up and down or side to side on the screen. (in the simple version of FIG. 1, only x and y motions of the toddler body parts or doll features are obtainable.) For comfort and effect, the image of the clown can also be taken or imported from other sources, for example a picture of the child's father.

As the child gets older, single or dual camera stereo of the invention can be used to increase the complexity with which the child can interact to 3, 4, 5, or 6 degrees of freedom with increasing sophistication in the game or learning experience.

Other applications of the invention are also possible. For example the toddler can be "watched" by the same TV camera periodically on alternate TV frames, with the image transmitted elsewhere so his mother knows what he is doing.

His movements indicate as well what he is doing and can be used as another monitoring means. For example, if he is running or moving at too great a velocity, the computer can determine this by a rate of change of position of coordinates, or by observing certain sequences of motion indicative of the motion desired to monitor. Similarly, and like the patient example above, if the coordinates monitored exceed a preset allowable area (e.g. a play space), a signal can be indicated by the computer.

The device also useful for amusement and learning purposes. The toddler's wrists or other features can be targeted, and when he claps, a clapping sound generated by the computer in proportion, or by different characteristics or the like. The computers can be programmed using known algorithms and hardware talk to him, and tell him to do things, and monitor what he did, making a game out of it if desired. It also can aid learning, giving him visual feedback and audio and verbal appreciation of a good answer, score and the like.

Similarly, we believe the invention can be used to aid learning and mental development in very young children and infants by relating gestures of hands and other bodily portions or objects such as rattles held by the child, to music and/or visual experiences.

Figure 21:
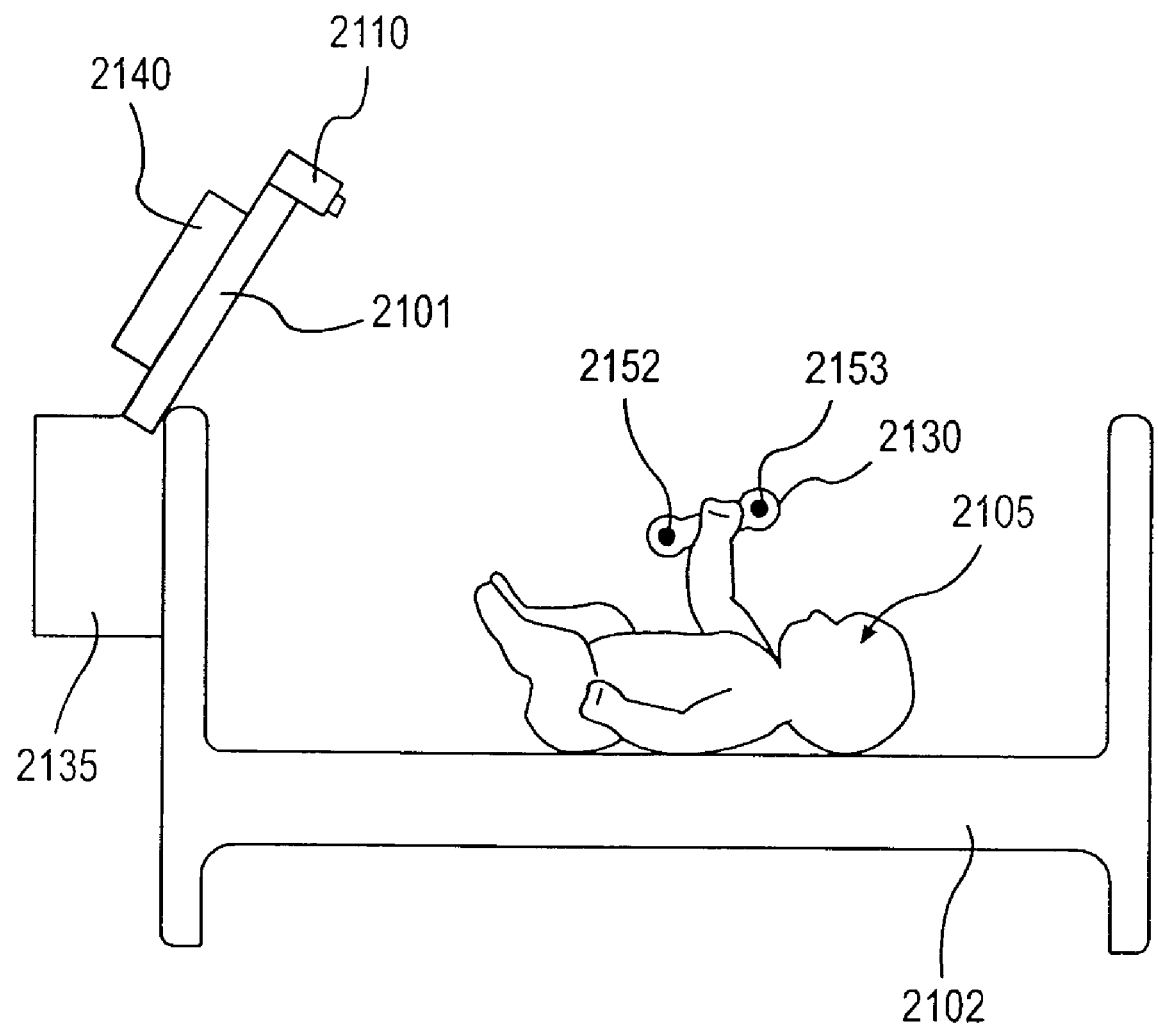
FIG. 21 illustrates a simple embodiment of the invention for toddlers and preschool age children, which is also useful to aid learning in very young children and infants by relating gestures of hands and other bodily portions or objects such as rattles held by the child, to music and/or visual experiences.

Let us consider the apparatus and method of FIG. 21 where we seek to achieve the advantageous play and viewing activity, but also to improve the learning of young children through the use of games, musical training and visual training provided by the invention—in the case shown here starting with children in their crib where they move from the rattle to mobile to busy box (e standing in crib) stage, the invention providing enhanced versions thereof and new toys made possible through LCD display attached to the crib and the like. The second issue is what sorts of new types of learning experiences can be generated that combine music, graphics and other things.

Consider FIG. 21, wherein an LCD TV display 2101 is attached to the end of crib 2102, in which baby 2105 is laying, placed so baby can see it. This display could be used to display for example a picture of the child's parents or pets in the home, or other desired imagery which can respond both visually and audibly to inputs from the baby sensed with the apparatus of FIG. 1, or other apparatus of the invention. These are then used to help illustrate the learning functions. The camera system, such as stereo pair, 2110 and 2115 are located as shown on the edges of the LCD screen or elsewhere as desired, and both are operated by the computer 2135. Notice that the design with the cameras integrated can be that of the lap top FIG. 22 application as well.

The baby's hands, fingers, head, feet or any other desired portion can be targeted, on his clothes or directly attached. Or natural features can be used if only simple actions such as moving a hand or head are needed (all possible today with low cost computer equipment suitable for the home). And importantly, the baby can easily hold a targeted rattle such as 2130 having target datums 2152 and 2153 at the ends(whose sound may be generated from the computer speaker 2140 instead, and be programmably changed from time to time, or react to his input) and he may easily touch as today a targeted mobile in the crib as well, or any other object such as a stuffed animal, block or what ever.

In essence, the invention has allowed the baby to interact with the computer for the first time in a meaningful way that will improve his learning ability, and IQ in future years. It is felt by the inventors that this is a major advance.

Some learning enhancements made possible are:

A computer recorded voice (with associated TV image if desired) of the child's parents or siblings for example, calling the child's name, or saying their names. Is responded to by the baby, and voice recognition picks up the child's response and uses it to cue some sort of activity. This may not even be voice as we know it but the sounds made by a child even in the early stages before it learns to talk. And it may stimulate him to talk, given the right software.

The child can also move his hands or head and similar things can take place. For example, he can create music, or react to classical music (a known learning improvement medium today) perhaps by keeping time, or to cue various visual cues such as artistic scenes or family and home scenes that he can relate to certain musical scores and the like.

The child can also use the computer to create art, by moving his hand, or the rattle or other object, and with some simple program, may be able to call up stored images as well.

Another embodiment could have the child responding to stored images or sounds, for example from a DVD Disc read by the computer 2135, and sort of vote on the ones he liked, by responding with movement over a certain threshold level, say a wiggle of his rattle. These images could later be played back in more detail if desired. And his inputs could be monitored and used by professional diagnosis to determine further programs to help the child, or to diagnose if certain normal patterns were missing—thus perhaps identifying problems in children at a very early age to allow treatment to begin sooner, or before it was too late.

The degree of baby excitement (amplitude and rate, etc. of rattle, wiggle, head arm movement).

Note that in an ultimate version, data directly taken from the child, as in FIG. 16 example, can be transmitted to a central learning center for assistance, diagnosis, or directly for interactivity of any desired type.

Therapy and Geriatrics

It is noted that an added benefit of the invention is that it can be used to aid mute and deaf persons who must speak with their hands the interpretation of sign language can be done by analyzing dynamic hand and finger position and converting via a learning sequence or other wise into computer verbiage or speech.

It is also noted that the invention aids therapy in general, by relating motion of a portion of the body to a desired stimulus. (visual auditory or physical touch) Indeed the same holds for exercise regimes of healthy persons.

And such activity made possible by the invention is useful for the elderly who may be confined to wheelchairs, unable to move certain parts of the body or the like. It allows them to use their brain to its fullest, by communicating with the computer in a different way.

Alternatively, stroke victims and other patients may need the action of the computer imagery and audio in order to trigger responses in their activity to re train them—much like the child example above.

An interesting example too are elderly people who have played musical instruments but can no longer play due to physical limitations. The invention allows them to create music, by using some other part of their body, and by using if needed, a computer generated synthesis of chords, added notes or what ever, to make up for their inability to quickly make the movements required.

Other Applications of the Invention

One of the advantages of this invention is that all sorts of objects can be registered in their function on the same camera system, operating both in single, dual or other stereo capabilities and all at low cost. This particular issue that the people, the objects, the whole stationary platform such as desk, floors, walls, al can be registered with the same generic principles, is a huge benefit of the application.

This means that the cost of writing the operating control software suitable for a large number and variety of applications only has to be done once. And similarly the way in which it operates, the way in which the people interact with it, only has to be learned once. Once one is familiar with one, one is almost familiar with all, and none need cost more than a few dollars or tens of dollars by itself in added cost.

The standard application aspect of the invention is important too from the point of view of sharing cost of development of hardware, software, target, material etc over the largest possible base of applications, such that production economies are maximized.

This is relatively the same as the situation today, where one uses a mouse all the time, for every conceivable purpose. But the mouse itself is not a natural object. One has to learn its function, and particular to each program, one may have to learn a different function. Whereas in the invention herein described, it is felt by the inventors that all functions are more or less intuitive and natural; the teaching, the games, the positioning of objects on a CAD screen. All these are just the way one would do it in normal life. It is possible to see this when one talks and how one uses one's hands to illustrate points or to hold objects in position or whatever. Whatever you do with your hands, you can do with this invention.

Speech Recognition.

One application of this actually to aid in speech recognition. For example, in Italy in particular, people speak with their hands. They don't speak only with their hands, but they certainly use hand signals and other gestures to illustrate their points. This is not of course just true in Italian language, but the latter is certainly famous for it.

This invention allows one to directly sense these positions and movements at low cost. What this may allow one to do then is utilize the knowledge of such gestures to act as an aid to speech recognition. This is particularly useful since many idiomatic forms of speech are not able to be easily recognized but the gestures around them may yield clues to their vocal solution.

For example, it is comprehended by the invention to encode the movements of a gesture and compare that with either a well known library of hand and other gestures taken from the populace as a whole or taught using the gestures of the person in question. The person would make the gesture in front of the camera, the movements and/or positions would be recorded, and he would record in memory, using voice or keyboard or both, what the gesture meant—which could be used in future gesture recognition, or voice recognition with accompanied gesture. A look up table can be provided in the computer software, where one can look up in a matrix of gestures, including the confidence level therein, including the meaning, and then compare that to add to any sort of spoken word meaning that needs to be addressed.

Artifacts

One of the advantages of the invention is that there is a vast number of artifacts that can be used to aid the invention to reliably and rapidly acquire and determine the coordinates of the object datums at little or no additional cost relative to the camera/computer system. For example we discussed retro-reflective targets on fingers, belt buckles, and many forms of jewelry, clothing and accessories (e.g. buttons) and the like. Many of these are decorative and objects such as this can easily be designed and constructed so that the target points represented are easily visible by a TV camera, while at the same time being interpreted by human as being a normal part of the object and therefore unobtrusive. (see for example referenced Tim Pryor copending applications) Some targets indeed can be invisible and viewed with lighting that is specially provided such as ultraviolet or infrared.

Surrogates

An object, via the medium of software plus display screen and/or sound may also take on a life as a surrogate for something else. For example, a simple toy car can be held in the hand to represent a car being designed on the screen. Or the toy car could have been a rectangular block of wood. Either would feel more or less like the car on the screen would have felt, had it been the same size at least, but neither is the object being designed in the computer and displayed on the screen.

Surrogates do not necessarily have to "feel right" to be useful, but it is an advantage of the invention for natural application by humans, that the object feel or touch can seem much like the object depicted on the screen display even if it isn't the same.

Anticipatory Moves

The invention can sense dynamically, and the computer connected to the sensor can act on the data intelligently. Thus the sensing of datum's on objects, targeted or not, can be done in a manner that optimizes function of the system.

For example if one senses that an object is rotating, and targets on one side may likely recede from view, then one can access a data base of the object, that indicates what targets are present on another side that can be used instead.

Additional Points

It is noted that in this case, the word target or datum essentially means a feature on the object or person for the purpose of the invention. As has been pointed out in previous applications by Tim Pryor, these can either natural features of the object such as fingernails or fingertips, hands or so on or can be what is often preferable, specialized datums put on especially to assist the function of the invention. These can include typically contrasting type datum's due to high brightness retro-reflection or color variation with respect to its surroundings, and often further distinguished or alternatively distinguished by some sort of pattern or shape.

Examples of patterns can include the patterns on cloth such as stripes, checks, and so on. For example the pointing direction of a person's arm or sleeve having a striped cloth pointing along the length of the sleeve would be indicated by determining the 3D pointing direction of the stripes. This can easily be done using the edge detection algorithms with a binocular stereo cameras here disclosed.

A useful shape can be a square, a triangle, or something not typically seen in the room, desktop, or other area that one would normally operate such that they stand out. Or even if a common shape, the combination of the shape with a specific color or brightness or both, often allows recognition.

It is appreciated that beyond the simple 2 dimensional versions as described such as in figure one, many applications benefit from or either depend on 3D operation. This is disclosed widely within the application as being desirably provided either from a single camera or two or more cameras operating to produce stereo imagery that can be combined to solve for the range distance Z. However, z dimension data can also be generated, generally less preferably, by other means, such as ultrasonics or radar, or laser triangulation if desired to effect the desirable features of many of the applications described.

Another point to stress concerning the invention is the fact of the performance of multiple functions. This allows it to be shared amongst a large number of different users and different uses for the same user and with a commonality as mentioned above of the teaching of it's function, the familiarity with it's use, and so forth.

One example of this is the use of a targeted hand which one moment is for a game, the next moment it's for a CAD input, and the next it's for music and whatever.

A key is the natural aspect of the invention, that it enables, at low cost and high reliability the use of learned natural movements of persons—for work, for play, for therapy, for exercise—and a variety of other work and safety uses here disclosed, and similar to those disclosed.

FIGS. 1 to 3 have illustrated several basic principles of optically aided computer inputs using single or dual/multi-camera (stereo) photogrammetry. Illustrated are new forms of inputs to effect both the design and assembly of objects.

When one pick ups polygon object—TV image of object itself can be processed, or more likely special ID data on the object or incorporated with the target datum's can be accessed by the computer to recognize the object, and call up the desired image—of the object, or of something it represents. Then as you move it, it moves—but you elaborate on computer rendition of it in due course given the users input and work, it gradually morphs to a car! (It could be a standard car instantly if the polygon were told to the computer to be a car).

One can draw on the computer screen, on a pad of paper or easel, or in the air with the invention. Computer instructions can come form all conventional sources, such as keyboards mice and voice recognition systems, but also from gestures and movement sequences for example using the TV camera sensing aspect of the invention.

Note that for example a targeted paint brush can instantly provide a real feeling way to use painting type programs. While painting itself is a 2D activity on the paper, the 3D sensing aspect of the invention is used to determine when the brush is applied to the paper, or lifted off, and in the case of pressing the brush down to spread the rush, the z axis movement into the plane of the paper determines how much spreading takes place (paper plane defined as x-y).

The 3D aspect is also used to allow the coordinate system to be transformed between the xyz as so defined, and the angulation of the easel with respect to the camera system wherever it is placed typically overhead, in front or to the side somewhere This freedom of placement is a major advantage of the invention, as is the freedom of choice of where targets are located on objects, thanks to the two camera stereo system in particulars ability to solve all necessary photogrammetric equations.

Note too that the angle of the brush or a pen held in hand with respect to the z axis can also be used to instruct the computer, as can any motion pattern of the brush either o the paper or waved in the air.

In CAD activities, the computer can be so instructed as to Parametric shape parameters such as % of circle and square. As with the brush, the height in z may be used to control an object width for example.

Illustrated too are a computer aided design system (CAD) embodiment according to the invention which illustrates particularly the application of specialized sculpture tools with both single and two alias object inputs, useful for design of automobiles, clothes and other applications.

Physical feel of object in each hand is unique, and combines feel with sight on screen—it feels like what it is shown to be, even if it isn't really. Feel can be rigid, semi rigid, or indeed one can actually remove (or add) material from alias object.

Where two or more alias or surrogate objects according to the invention, for example for use in sculpture, whittling and other solid design purposes with one, two, or more coordinated objects.

Illustrated were additional alias objects according to the invention, for example for use in sculpture, whittling and other solid design purposes with one, two, or more coordinated objects.

The unique ability of the invention to easily create usable and physically real alias objects results from the ease in creating targeted objects which can be easily seen at high speed by low cost TV and computer equipment (high speed is here defined as greater than 3 frames per second say, and low cost is under $5000 for the complete system including camera, light source(s), computer and display (multiple camera version somewhat higher).

The objects can be anything on which 3M Scotch light 7615 type retro-reflective material can be placed, or other reflective or high contrast material incorporated in to the surface of an object. You can stick them on fingers, toys or whatever, and can be easily removed if desired. With two (or more) camera stereo systems, no particular way of putting them on is needed, one can solve photogrammetrically for any non co-linear set of three to determine object position and orientation, and any one target can be found in x y and z.

The physical nature of the alias object, is a very important aspect of the invention. It feels like a real object, even though it's a simple targeted block, one feels that it is a car, when you view the car representation on the screen that the block position commands. Feel object, look at screen, this is totally different than controlling an object on a screen with a mouse.

Even more exciting and useful is the relative juxtaposition of two objects, with both on the screen.

For example, a child can affix special targets (using Velcro, tape, pins, or other means) on his favorite stuffed toys and then he can have them play with each other, or even a third. Or two children can play, each with their own doll or stuffed animal. But on screen, they convert the play into any kind of animal, including scenery (e.g. a barnyard). The animals can have voice added in some way, either by the computer, or by prerecorded sounds, or in real time via microphones. Via the internet, new voice inputs or other game inputs can be downloaded at will from assisting sites. And programs, and voice, and TV imagery can be exchanged between users.

Computer imagery of the actual animal can be taken using the same TV camera, recorded, and the 3D position determined during play, and the image transformed into a 3D image, rotated or whatever.

The same argument of attaching targets to toys, applies to objects which are the physical manifestations of learned skills:

A pencil to a draftsman;
A scissors, chalk, and rule to a dressmaker;
A brush to an artist;
An instrument or portion(e.g. a drumstick, a bow) to a musician;
A axe to a lumberjack;
A drill, hammer, or saw to a carpenter;
A pistol to a policeman or soldier;
A scalpel to a surgeon;
A drill to a dentist;
And so on.

Each person can use a real, or alias object (e.g. a broomstick piece for a hammer) targeted as he chooses, in order to use the audio and visual capabilities of computer generated activity of the invention. All are more natural to him or her, than a mouse! In each case too, the object to be worked on can also be sensed with the invention:

The cloth of the dress;
The paper(or easel/table) of the artist or draftsman;
The violin of the musician (along with the bow);
The log of the lumberjack;
The teeth or head of the dental patient;
And so on.

The computer program, using the sensor input, can faithfully utilize the input, or it can extrapolate from it. For example rather than play middle C, it can play a whole chord, or knowing the intended piece, play several of the notes in that piece that follow. Similarly, one can start a simulated incision with a scalpel, and actually continue it a distance along the same path the student doctor started.

Sounds, Noise and Visual Cues

The cocking of a hammer on a toy pistol can act as a cue in many cases. A microphone connected to the computer can pick this up and analyze the signature and determine that a gun may be fired. This can cause the vision analysis program looking at the TV image to look for the pistol, and to anticipate the shot. The sound of the gun, rather than a visual indicator, can alternatively be used to cue the displayed image data as well. Two microphones if used, can be used to triangulate on the sound source, and even tell the TV camera where to look.

In many cases sound and physical action are related. Sounds for example can be used to pick up a filing noise, to indicate that a alias object was actually being worked by a tool. The TV camera(s) can monitor the position and orientation of each, but the actual contact registered by sound. Or contact could be just the physical proximity of one image to another—however the sound is created by the actual physical contact which is more accurate, and more real to the user.

Signature Recognition

The invention can look for many signatures of object position and movement—including complex sequences. This has been described in another context relative to FIG. 7 for recognizing human gestures.

The recognition algorithm can be taught before hand using the position or movement in question as an input, or it may be preprogrammed, to recognize data presented to it from a library, often specific to game/activity of interest.

Such recognition can also be used to Anticipate an action, For example, if a bow string or hand is moved directly back from a bow, recognition is that one is Drawing a bow, and that an arrow may be ready to be shot. The computer can then command the screen display or sound generation speakers to react (eyes, head move, person on screen runs away, etc.).

Similarly, the actual action of releasing the bow can be sensed, and the program react to the move.

It is of use to consider some of what even the simplest version of the invention, illustrated in FIG. 1a, could accomplish? In the lowest cost case, This uses retroreflective glass bead tape, or jewelry on an object to allow determination in x and y (plane perpendicular to camera axis) of, for example:
1. position of one or more points on or portions of, or things to do with, babies, game players, old persons, disabled, workers, homemakers, etc.
2. Determine position of object such as something representing position or value of something else.
3. Determine location of a plurality of parts of the body, a body and an object, two objects simultaneously, etc.
4. With additional software and datums, expand to FIG. 1b version, and Determine up to six dimensional degrees of freedom of object or of one object or more with respect to each other). Use Single camera but with target set having known relationships. (Single camera photogrammetry).

Today, costs involved to do the foregoing would appear to be a USB camera and in the simplest case, no frame board; just right into the computer. This today could result in images being processed at maybe 10 hertz or less. Simple thresh holding, probably color detection would all that would be needed. More sophisticated shape, recognition and finding of complex things in the scene are not required in simple cases with limited background noise, and are aided by use of the retroreflector or LED sources.

The only other equipment that would be needed in this scenario is the lighting unit that would surround the camera. Clearly this would be somewhat camera specific in terms of its attachment and so on. Many cameras, as it would appear that have been designed for internet.

Cameras and lighting as needed could be built right into the TV display units.

In the simplest case, there would be simply one target and one only. This would allow a simple TV camera to give 2D point position—essentially be a 2D mouse in space (except that absolute position of the point relative to the camera can be determined—the mouse of today is incremental from its starting point).

Some applications:
1. Direct mouse replacement. The mouse today is in 2D and so is this. Generally speaking, depending on where the camera is, this is either the same two dimensions, that is looking down at the work space, or the two dimensions are in another plane.
2. Indeed one could apply a single target capable of being sensed by the TV camera of the invention on the ordinary mouse (or joystick or other input) of today. This could give more degrees of freedom of information, such as angles or movement off the mouse table surface (z direction). For example, a 3D input device can be produced since the camera would provide X-Z (z perpendicular to plane of surface) and the mouse would provide X-Y (in plane of surface_so therefore you would have all three dimensions.
3. Carrying the mouse elaboration one step further, a mouse point could be movable.

That is, the target could be wiggled by the finger holding the mouse, to signal a move or other action to the computer. This would then allow you to put inputs to the computer into the device without adding any electrical wires or anything.
4. Transducers can also be used as single point inputs, for example of pressures or temperatures or anything that would make a target move, for example in the later case the target being on the end of a bimetal strip which changes position with temperature.

Application to Multiple Points and Objects

Another application is to register the relative position of one object to another.

For example, today the mouse is basically an odometer. It can't really give any positional data relative to something but can only give the distance moved in two directions which is then converted from some home location onto the screen.

The invention however is absolute, as the camera is as well. It can provide data on any point to any other point or even to groups of points—on objects, humans, or both.

Even using the simplest form of the invention, one can put a target on a human and track it or find it's position in space. Here again, in the beginning in for example in two dimensions, X and Y only (FIG. 1a).

For example, with a single point one can make mouse adjunct where moving one's head with a target on it provides an input into the computer while still holding the mouse and everything in normal juxtaposition.

One step beyond this is to have more than one point on the human. Clearly a finger relative to another finger or a hand relative to another hand, either or both to the head and so on.

As has been noted, a method of achieving high contrast and therefore high reliability is to utilize an LED source as the target. This is possible with the invention, but requires wiring on the object, and thus every object that is to be used has to have a power cable or a battery, or a solar cell or other means to actuate the light—a disadvantage if widespread applicability is desired.

The LED in its simplest form can be powered by something that itself is powered. This means an LED on top of the mouse for example. On the other hand, typically the LED would be on an object where you would not like a power cable and this would then mean battery operated.

The idea of remote power transmission to the target LED or other self luminous target however should be noted. It is possible to transmit electromagnetic radiation (radio, IR, etc) to a device on an object, which in turn would generate power to an LED which then converts that to DC or modulated light capable of detection optically. Or the device itself can directly make the conversion.

The basic technical embodiment of the invention illustrated in FIG. 1 uses a single TV camera for viewing a group of 3 or more targets(or special targets able to give up to a 6 degree of freedom solution), or a set of at least two TV cameras for determining 3D location of a number of targets individually, and in combination to provide object orientation. These cameras are today adapted to the computer by use of the USB port or better still, fire wire (IEE 1394). The cameras may be employed to sense natural features of objects as targets, but today for cost and speed reasons, are best used with high contrast targets such as LED sources on the object, or more generally with retro-reflective targets. In the latter case lighting as with IR LED's is provided near the optical axis of each camera used. For scene illumination, which can be done best on alternate camera frames form target image acquisition, broad light sources can be used. Laser pointers are also very useful for creating one or more high contrast indications, simultaneously, or in sequence on object surfaces that can be sensed by the stereo cameras (typically two or more).

Using laser (or other triangulation source projection), or the contacting of an object with a targeted finger or stylus member, an object can be digitized using the same camera system used for target related inputs. This is an important cost justification of total system capability.

Coincidence of action—i.e. sensed gesture using the invention can be used to judge a voice operated signal legitimate in a noisy background. Similarly other inputs can be judged effectively if combined with the position and movement sensing of the invention.

Invention combined with voice input makes user much more portable. For example can walk around room and indicate to the computer both action and words.

The target if a plain piece of glass bead retroreflector, cannot be seen typically beyond angles plus or minus 45 degrees from the normal of the reflector aligned with the camera viewing axis. (indeed some material drops out at 30 degrees) When a performer spins around, this condition is easily exceeded, and the data drops out. For this reason, targets pointing in different directions may be desirable. Rather than using several planar targets with the above characteristics, each pointed in a different direction say rotationally about the head to toe axis of a dancer say, one can use in some cases multi-directional targets, typically large balls, beads and faceted objects such as diamonds.

In some case only 3D locations are needed. The orientation at times is a secondary consideration. In these cases the target 1650 could be attached to gyroscope 1655 that in turn is attached to a base 1660 by a ball joint 1665 or other free floating mechanical link. The target could be initially tilted directly toward the cameras allowing the cameras to view the target more precisely. The base plate is then attached to the object to be tracked. The position of the attachment can be calculated once the target location and orientation are established. Since the gyroscope would hold the target orientation toward the cameras as the dance turns, this method extends the range of motion allowed by the dancer or other users.

It should be noted that many of the embodiments of the invention described do not depend on TV cameras, Stereo imaging, special targets, or the like, but rather can be used with any sort of non contact means by which to determine position of a point, multiple points, or complete position and orientation of the object, or portion of a human used in the embodiment. While optical, and particularly TV camera based systems are preferred for their low cost and wide functionality, ultra sonic and microwaves can also be used as transduction means in many instances.

Specialized Definitions Used in the Application
Target Volume

A "target Volume" is the volume of space (usually a rectangular solid volume) visible to a video camera or a set of video cameras within which a target will be acquired and its position and/or orientation computed.

Interrupt Member

An "Interrupt member" is a device that senses a signal to the systems computer allowing a computer program to identify the beginning of one path of a target and the end of the preceding path. It can also identify a function, object, or parameter value. Examples of an Interrupt member are:
1. A given key on the system's keyboard.
2. A voice recognition system capable of acting on a sound or spoken word.
3. A button attached to a game port, serial port, parallel port, special input card, or other input port.
4. A trigger, switch, dial, etc. that can turn on a light or mechanically make visible a new target or sub-target with unique properties of color, shape, and size.

Quant

A "Quant" is a unique discretized or quantized target path (defined by location, orientation, and time information) together with the target's unique identification number (ID). A Quant has an associated ID (identification number). A Quant is composed of a sequence of simple path segments. An example of a Quant that could be used to define command in a CAD drawing system to create a rectangle might be a target sweep to the right punctuated with a short stationary pause followed by an up sweep and pause, a left sweep and pause, a down sweep and pause, and finally ended with a key press on the keyboard. In this example the Quant is stored as a set (4, 1, 2, 3, 4, a, 27) where 4 is the number of path segments, 1-4 are number that identify path segment directions (i.e. right, up, left, down), "a" is the member interrupt (the key press a), and 27 is the target ID. Note that the punctuation that identifies a new path direction could have been a radical change in path direction or target orientation or speed.

Light as used herein includes all electromagnetic wavelengths from ultraviolet to near infrared.

We claim:
1. A game comprising:
a game member adapted to be freely held in a hand of a player of said game and moved in three dimensions by the player in order to play the game, the game member adapted to provide an output indicating a player command;
a single TV camera adapted to obtain images of said game member as the game member is moved in three dimensions and adapted to obtain images of a body part separate from the hand as the body part is moved in three dimensions;
a means to analyze said images obtained by the TV camera to provide three dimensional movement information of at least one of said game member and the body part as the game member and the body part are moved in three dimensions, wherein the three dimensional movement information includes a change in distance relative to said camera;
a display providing a video representation of an object; and
a computer means to control and to move the video representation of the object on said display using said three dimensional movement information.

2. Apparatus according to claim 1 wherein said video representation is of a same type of object as said game member.

3. Apparatus according to claim 1 wherein said video representation is of an enhanced object which is of the same type as the game member.

4. Apparatus according to claim 1 wherein said three dimensional position information also concerns an orientation or change in orientation of said game member.

5. Apparatus according to claim 1 wherein one or more natural features of said game member are utilized to provide said information.

6. Apparatus according to claim 1 wherein one or more artificial features of said game member are utilized to provide said information.

7. Apparatus according to claim 1 wherein said computer provides sounds relating to the position of said game member.

8. Apparatus according to claim 1 wherein said game member is a toy airplane or doll.

9. A method for playing a video game comprising the steps of:
- providing a game member adapted to provide an output indicating a player command;
- moving in three dimensions the game member freely held in a hand of a game player and moving in three dimensions a body part separate from the hand to play the video game;
- displaying on a computer controlled display a video representation of a game object whose movement in the display is controlled by the three dimensional movement of the game member or the body part;
- using a single TV camera, obtaining an image of said game member as the game member moves in three dimensions and obtaining an image of the body part as the body part moves in three dimensions;
- analyzing said images of said game member and the body part obtained by the single TV camera to provide three dimensional movement information of said game member and the body part as the game member and the body part are moved in three dimensions, wherein the three dimensional movement information includes a change in distance relative to the camera; and
- controlling and moving the game object in said display using said three dimensional movement information.

10. A method according to claim 9 wherein said game member is a toy.

11. A method according to claim 10 wherein said game member is a doll or airplane.

12. A method according to claim 9 wherein said game member is a simplified representation of the game object.

13. A method according to claim 9 wherein said game member is a weapon.

14. A method according to claim 12 wherein said weapon is a sword or gun.

15. A method according to claim 9 wherein said game member is a member used in playing a sport.

16. A method by which a player may play a video game, comprising the steps of:
- providing a computer controlled display;
- displaying a representation of a game related object on said display;
- simulating, with at least one of a game member and a body part of said player, at least a portion of said game related object depicted on said display;
- imaging said at least one of a game member and a body part of said player with a single TV camera as the game member or body part moves in three dimensions from a first position to a second position to play the video game;
- using the images obtained by said single TV camera, determining three dimensional movement information concerning said game member if said game member is imaged and said body part if said body part is imaged as the game member or body part is moved in three dimensions from the first position and to the second position, wherein the three dimensional movement information includes a change in distance relative to the camera; and
- from said determined information, controlling said display to move said game related object in the display which game related object movement minors the three dimensional movement of the game member or body part from the first position to the second position thereof.

17. A method according to claim 16 wherein said three dimensional position information further includes orientation of said body part.

18. A method according to claim 16 wherein said game related object is an airplane and said body parts are the players arms representing the wings of said airplane.

19. A method according to claim 16 wherein said game related object depicted on said display is a portion of a person.

20. A method according to claim 16 wherein the camera includes a CMOS image sensor or a CCD image sensor.

21. A method according to claim 9 wherein the camera includes a CMOS image sensor or a CCD image sensor.

22. A method according to claim 9 further including determining the orientation of the game member.

* * * * *

UNITED STATES PATENT AND TRADEMARK OFFICE
CERTIFICATE OF CORRECTION

| | | |
|---|---|---|
| PATENT NO. | : 8,111,239 B2 | Page 1 of 1 |
| APPLICATION NO. | : 11/429305 | |
| DATED | : February 7, 2012 | |
| INVENTOR(S) | : Pryor et al. | |

It is certified that error appears in the above-identified patent and that said Letters Patent is hereby corrected as shown below:

Column 60, Claim 16, Line 21:
"minors" should be --mirrors--

Signed and Sealed this
Third Day of April, 2012

David J. Kappos
*Director of the United States Patent and Trademark Office*